United States Patent
Passno et al.

(10) Patent No.: US 12,398,176 B2
(45) Date of Patent: Aug. 26, 2025

(54) USE OF RAMAN SPECTROSCOPY IN DOWNSTREAM PURIFICATION

(71) Applicant: Regeneron Pharmaceuticals, Inc., Tarrytown, NY (US)

(72) Inventors: Christina Passno, Tarrytown, NY (US); Christopher Cowan, Tarrytown, NY (US); Andrew Tustian, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 765 days.

(21) Appl. No.: 17/742,243

(22) Filed: May 11, 2022

(65) Prior Publication Data

US 2022/0340617 A1    Oct. 27, 2022

Related U.S. Application Data

(63) Continuation of application No. 16/550,989, filed on Aug. 26, 2019, now Pat. No. 11,358,984.

(Continued)

(51) Int. Cl.
*C07K 1/36*    (2006.01)
*C07K 1/14*    (2006.01)
(Continued)

(52) U.S. Cl.
CPC ............ *C07K 1/36* (2013.01); *C07K 1/145* (2013.01); *C07K 1/34* (2013.01); *G01N 1/4044* (2013.01);
(Continued)

(58) Field of Classification Search
CPC . C07K 1/145; C07K 1/34; C07K 1/36; C07K 16/00; G01N 1/4044; G01N 1/4077;
(Continued)

(56) References Cited

U.S. PATENT DOCUMENTS 109,819 A    12/1870    Hornbeck et al.
5,675,931 A    10/1997    Wasserman
(Continued)

FOREIGN PATENT DOCUMENTS

AR          113449 A1    5/2020
AU     2004201496 A1    5/2004
(Continued)

OTHER PUBLICATIONS

Abu-Absi et al., Real time monitoring of multiple parameters in mammalian cell culture bioreactors using an in-line Raman spectroscopy probe. Biotechnol Bioeng. May 2011;108(5):1215-21.

(Continued)

*Primary Examiner* — Jennifer Wecker
(74) *Attorney, Agent, or Firm* — McCarter & English, LLP

(57) ABSTRACT

In situ Raman spectroscopy methods and systems for characterizing or quantifying a protein purification intermediate and/or final concentrated pool during production or manufacture are provided. In one embodiment, in situ Raman spectroscopy is used to characterize or quantify protein purification intermediates critical quality attributes during downstream processing (i.e., after harvest of the protein purification intermediate). For example, the disclosed in situ Raman spectroscopy methods and systems can be used to characterize and quantify protein purification intermediates as the protein purification intermediates are purified, condensed, or otherwise formulated into the final drug product to be sold or administered.

29 Claims, 20 Drawing Sheets

Related U.S. Application Data

(60) Provisional application No. 62/723,188, filed on Aug. 27, 2018.

(51) Int. Cl.
*C07K 1/34* (2006.01)
*G01N 1/40* (2006.01)
*G01N 21/65* (2006.01)

(52) U.S. Cl.
CPC ............ *G01N 1/4077* (2013.01); *G01N 21/65* (2013.01); *G01N 2001/4088* (2013.01)

(58) Field of Classification Search
CPC ... G01N 2001/4088; G01N 2021/8416; G01N 21/65
See application file for complete search history.

(56) References Cited

U.S. PATENT DOCUMENTS

| | | | |
|---|---|---|---|
| 5,912,113 A | 6/1999 | Nakamura et al. |
| 6,156,570 A | 12/2000 | Hu et al. |
| 6,455,260 B1 | 9/2002 | Muller et al. |
| 6,660,836 B1 | 12/2003 | Anderson et al. |
| 6,780,978 B2 | 8/2004 | Jibu |
| 6,939,686 B2 | 9/2005 | Ling et al. |
| 6,942,968 B1 | 9/2005 | Dickinson et al. |
| 6,979,540 B2 | 12/2005 | Benneteau et al. |
| 6,979,733 B2 | 12/2005 | Zhao et al. |
| 7,101,671 B2 | 9/2006 | Gao |
| 7,129,048 B2 | 10/2006 | Bruchez et al. |
| 7,144,979 B2 | 12/2006 | Maeji et al. |
| 7,169,556 B2 | 1/2007 | Park et al. |
| 7,183,050 B2 | 2/2007 | Krull |
| 7,195,873 B2 | 3/2007 | Filigheddu et al. |
| 7,198,900 B2 | 4/2007 | Woudenberg et al. |
| 7,199,217 B2 | 4/2007 | DiMarchi et al. |
| 7,221,457 B2 | 5/2007 | Jorgenson et al. |
| 7,229,960 B2 | 6/2007 | Pero et al. |
| 7,238,476 B2 | 7/2007 | McKeown et al. |
| 7,258,861 B2 | 8/2007 | Lucas et al. |
| 7,270,951 B1 | 9/2007 | Stemple et al. |
| 7,291,461 B2 | 11/2007 | Welch et al. |
| 7,294,697 B2 | 11/2007 | Xu et al. |
| 7,303,869 B2 | 12/2007 | Stevens et al. |
| 7,309,409 B2 | 12/2007 | Amirkhanian et al. |
| 7,323,319 B2 | 1/2008 | Huang |
| 7,332,586 B2 | 2/2008 | Franzen et al. |
| 7,348,404 B2 | 3/2008 | Holm et al. |
| 7,351,526 B2 | 4/2008 | Soto et al. |
| 7,371,524 B2 | 5/2008 | Dandliker et al. |
| 7,371,834 B2 | 5/2008 | Penninger et al. |
| 7,393,924 B2 | 7/2008 | Vitaliano et al. |
| 7,396,824 B2 | 7/2008 | Sasisekharan et al. |
| 7,402,422 B2 | 7/2008 | Fuchs et al. |
| 7,429,491 B2 | 9/2008 | Luan et al. |
| 7,431,685 B2 | 10/2008 | Frey et al. |
| 7,465,578 B2 | 12/2008 | Berlin et al. |
| 7,482,425 B2 | 1/2009 | Kochendoerfer et al. |
| 7,524,941 B2 | 4/2009 | Olejnik et al. |
| 7,556,815 B2 | 7/2009 | Coleman et al. |
| 7,563,586 B2 | 7/2009 | Okuse et al. |
| 7,572,409 B2 | 8/2009 | Bryning et al. |
| 7,572,603 B2 | 8/2009 | Small et al. |
| 7,572,640 B2 | 8/2009 | Goix et al. |
| 7,585,624 B2 | 9/2009 | Fraser et al. |
| 7,589,079 B2 | 9/2009 | Jonaitis et al. |
| 7,592,434 B2 | 9/2009 | Kerovuo et al. |
| 7,595,198 B2 | 9/2009 | Olejnik et al. |
| 7,642,079 B2 | 1/2010 | Cayouette et al. |
| 7,642,344 B2 | 1/2010 | Van Ness et al. |
| 7,662,566 B2 | 2/2010 | Timms et al. |
| 7,662,644 B2 | 2/2010 | Hahn et al. |
| 7,671,178 B1 | 3/2010 | Phillips et al. |
| 7,692,002 B2 | 4/2010 | Alberto et al. |
| 7,700,277 B2 | 4/2010 | Ambrose et al. |
| 7,727,722 B2 | 6/2010 | Nelson et al. |
| 7,763,649 B2 | 7/2010 | Lockwood et al. |
| 7,771,938 B2 | 8/2010 | Zanni et al. |
| 7,776,528 B2 | 8/2010 | Lakowicz |
| 7,777,011 B2 | 8/2010 | Fishleigh et al. |
| 7,781,572 B2 | 8/2010 | Bartlett et al. |
| 7,803,786 B2 | 9/2010 | McMahon et al. |
| 7,812,137 B2 | 10/2010 | Friedman et al. |
| 7,816,079 B2 | 10/2010 | Fischer |
| 7,824,890 B2 | 11/2010 | Hoser et al. |
| 7,824,895 B2 | 11/2010 | Short et al. |
| 7,824,908 B2 | 11/2010 | Maine et al. |
| 7,838,218 B2 | 11/2010 | Aojula et al. |
| 7,838,237 B2 | 11/2010 | Sampson et al. |
| 7,843,562 B2 | 11/2010 | Chan et al. |
| 7,851,152 B2 | 12/2010 | Chen |
| 7,875,462 B2 | 1/2011 | Gjerde et al. |
| 7,875,465 B2 | 1/2011 | Shiotsuka et al. |
| 7,888,073 B2 | 2/2011 | Densham |
| 7,893,007 B2 | 2/2011 | Ladner et al. |
| 7,893,253 B2 | 2/2011 | Lohse et al. |
| 7,919,249 B2 | 4/2011 | Gelfand et al. |
| 7,927,791 B2 | 4/2011 | Welch et al. |
| 7,939,256 B2 | 5/2011 | Williams |
| 7,939,257 B2 | 5/2011 | Kwitek et al. |
| 7,943,301 B2 | 5/2011 | Sen et al. |
| 7,951,572 B2 | 5/2011 | Kim et al. |
| 7,951,776 B2 | 5/2011 | Gelber |
| 7,960,124 B2 | 6/2011 | Popovic et al. |
| 7,960,516 B2 | 6/2011 | Matheus et al. |
| 7,989,219 B2 | 8/2011 | Shiotsuka et al. |
| 8,003,126 B2 | 8/2011 | Jungles et al. |
| 8,025,883 B2 | 9/2011 | Brooks et al. |
| 8,058,410 B2 | 11/2011 | Jungbauer et al. |
| 8,062,841 B2 | 11/2011 | Su et al. |
| 8,062,883 B2 | 11/2011 | Woudenberg et al. |
| 8,063,184 B2 | 11/2011 | Allawi et al. |
| 8,084,202 B2 | 12/2011 | Castro |
| 8,093,005 B2 | 1/2012 | Jarhede et al. |
| 8,097,421 B2 | 1/2012 | Koo |
| 8,097,442 B2 | 1/2012 | Hitchman et al. |
| 8,110,673 B2 | 2/2012 | Bazan et al. |
| 8,114,587 B2 | 2/2012 | Gite et al. |
| 8,114,596 B2 | 2/2012 | Kaufman |
| 8,133,471 B2 | 3/2012 | Brooks et al. |
| 8,133,984 B2 | 3/2012 | Christensen |
| 8,148,324 B2 | 4/2012 | Greenberg et al. |
| 8,148,516 B2 | 4/2012 | Williams et al. |
| 8,163,566 B2 | 4/2012 | Smith et al. |
| 8,168,399 B2 | 5/2012 | Frutos et al. |
| 8,168,433 B2 | 5/2012 | Gehman et al. |
| 8,173,445 B1 | 5/2012 | Williams et al. |
| 8,173,793 B2 | 5/2012 | Friedman et al. |
| 8,193,430 B2 | 6/2012 | Papadimitrakopoulos et al. |
| 8,198,403 B2 | 6/2012 | Dieckmann et al. |
| 8,212,132 B2 | 7/2012 | Swager et al. |
| 8,216,855 B2 | 7/2012 | Pipper et al. |
| 8,221,719 B2 | 7/2012 | Peuralahti et al. |
| 8,227,428 B2 | 7/2012 | Day et al. |
| 8,227,590 B2 | 7/2012 | Ranga et al. |
| 8,243,267 B2 | 8/2012 | Siegel et al. |
| 8,252,559 B2 | 8/2012 | Fasan et al. |
| 8,263,350 B2 | 9/2012 | Koide et al. |
| 8,263,412 B2 | 9/2012 | Wachter et al. |
| 8,268,981 B2 | 9/2012 | Birkenmeyer et al. |
| 8,273,403 B2 | 9/2012 | Barden et al. |
| 8,273,532 B2 | 9/2012 | Gershow et al. |
| 8,278,085 B2 | 10/2012 | Trotta et al. |
| 8,298,765 B2 | 10/2012 | Luo et al. |
| 8,318,416 B2 | 11/2012 | Tsang et al. |
| 8,318,897 B2 | 11/2012 | Birkenmeyer et al. |
| 8,323,694 B2 | 12/2012 | Hainfeld |
| 8,325,339 B2 | 12/2012 | Ebstein |
| 8,329,647 B2 | 12/2012 | Pfuetzner et al. |
| 8,338,606 B2 | 12/2012 | Perrone et al. |
| 8,350,007 B2 | 1/2013 | Jennings et al. |
| 8,357,505 B2 | 1/2013 | Frommer et al. |
| 8,361,803 B2 | 1/2013 | Fan et al. |

(56) References Cited

U.S. PATENT DOCUMENTS

| | | |
|---|---|---|
| 8,361,806 B2 | 1/2013 | Gjerde et al. |
| 8,377,657 B1 | 2/2013 | Shuber |
| 8,383,114 B2 | 2/2013 | Sloey et al. |
| 8,383,585 B2 | 2/2013 | Pfuetzner et al. |
| 8,414,861 B2 | 4/2013 | Jeong et al. |
| 8,426,184 B2 | 4/2013 | Blum et al. |
| 8,426,572 B2 | 4/2013 | Santner et al. |
| 8,436,141 B2 | 5/2013 | Becker |
| 8,445,288 B2 | 5/2013 | Sorensen et al. |
| 8,460,471 B2 | 6/2013 | Takeshima et al. |
| 8,460,472 B2 | 6/2013 | Takeshima et al. |
| 8,476,020 B1 | 7/2013 | Scholl et al. |
| 8,476,033 B2 | 7/2013 | Cheek et al. |
| 8,477,307 B1 | 7/2013 | Yufa et al. |
| 8,481,263 B2 | 7/2013 | Lim et al. |
| 8,486,634 B2 | 7/2013 | Lim et al. |
| 8,486,680 B2 | 7/2013 | Gray et al. |
| 8,501,172 B2 | 8/2013 | Kaplan et al. |
| 8,501,923 B2 | 8/2013 | Rothemund |
| 8,519,031 B2 | 8/2013 | Parker et al. |
| 8,524,450 B2 | 9/2013 | Moon et al. |
| 8,530,626 B1 | 9/2013 | Cardamone |
| 8,536,324 B2 | 9/2013 | Mohapatra et al. |
| 8,547,550 B2 | 10/2013 | Carpenter |
| 8,557,956 B2 | 10/2013 | Cheng et al. |
| 8,563,476 B2 | 10/2013 | Lillard, Jr. |
| 8,569,008 B2 | 10/2013 | Choi et al. |
| 8,569,468 B2 | 10/2013 | Chen et al. |
| 8,574,892 B2 | 11/2013 | Su |
| 8,586,530 B2 | 11/2013 | Ferreira et al. |
| 8,609,337 B2 | 12/2013 | Pregibon et al. |
| 8,614,057 B2 | 12/2013 | Allen et al. |
| 8,614,086 B2 | 12/2013 | Holt et al. |
| 8,628,952 B2 | 1/2014 | Stuelpnagel et al. |
| 8,647,821 B2 | 2/2014 | Castro et al. |
| 8,658,381 B2 | 2/2014 | Mansson et al. |
| 8,658,613 B2 | 2/2014 | Bruno |
| 8,669,055 B2 | 3/2014 | Bazan et al. |
| 8,673,556 B2 | 3/2014 | Akeson et al. |
| 8,673,570 B2 | 3/2014 | Shafer |
| 8,679,859 B2 | 3/2014 | Yan et al. |
| 8,697,390 B2 | 4/2014 | Skinderso et al. |
| 8,697,434 B2 | 4/2014 | Voorhees |
| 8,697,645 B2 | 4/2014 | Acharya et al. |
| 8,697,656 B2 | 4/2014 | Fournial et al. |
| 8,734,793 B2 | 5/2014 | Tu et al. |
| 8,747,484 B2 | 6/2014 | Benayahu et al. |
| 8,748,696 B2 | 6/2014 | Rathinasabapathi et al. |
| 8,753,870 B2 | 6/2014 | Lee et al. |
| 8,754,055 B2 | 6/2014 | Allen et al. |
| 8,765,367 B2 | 7/2014 | Breidenthal et al. |
| 8,765,369 B2 | 7/2014 | Dubus et al. |
| 8,765,373 B2 | 7/2014 | Majda |
| 8,765,684 B2 | 7/2014 | Jonczyk et al. |
| 8,765,938 B2 | 7/2014 | Hara et al. |
| 8,771,938 B2 | 7/2014 | Chang et al. |
| 8,779,097 B2 | 7/2014 | Nagarkar et al. |
| 8,785,162 B2 | 7/2014 | De Souza et al. |
| 8,785,608 B2 | 7/2014 | Rigal et al. |
| 8,796,206 B2 | 8/2014 | Sloey et al. |
| 8,815,611 B2 | 8/2014 | Bunch et al. |
| 8,858,770 B2 | 10/2014 | Tan et al. |
| 8,877,478 B2 | 11/2014 | Steer et al. |
| 8,883,424 B2 | 11/2014 | Chee et al. |
| 8,889,623 B2 | 11/2014 | Hoeprich et al. |
| 8,896,829 B2 | 11/2014 | Furusho |
| 8,916,154 B2 | 12/2014 | Das et al. |
| 8,916,606 B2 | 12/2014 | Tour et al. |
| 8,932,558 B2 | 1/2015 | Madasamy |
| 8,933,197 B2 | 1/2015 | Stemmer et al. |
| 8,937,156 B2 | 1/2015 | Qi |
| 8,945,932 B2 | 2/2015 | Patton et al. |
| 8,975,390 B2 | 3/2015 | Bruno |
| 9,006,458 B2 | 4/2015 | Chang et al. |
| 9,051,605 B2 | 6/2015 | Son et al. |
| 9,067,962 B2 | 6/2015 | De Paul et al. |
| 9,068,969 B2 | 6/2015 | Pelligrini |
| 9,069,700 B2 | 6/2015 | Ishiguro |
| 9,073,970 B2 | 7/2015 | Muller-Spath et al. |
| 9,085,598 B2 | 7/2015 | Alaoui-Jamali et al. |
| 9,085,607 B2 | 7/2015 | Phadke et al. |
| 9,085,618 B2 | 7/2015 | Ramasubramanyan et al. |
| 9,085,766 B2 | 7/2015 | Crane et al. |
| 9,102,520 B2 | 8/2015 | Han et al. |
| 9,102,920 B2 | 8/2015 | Feng et al. |
| 9,115,178 B2 | 8/2015 | Gilar et al. |
| 9,115,189 B2 | 8/2015 | Lou et al. |
| RE45,660 E | 9/2015 | Weiner et al. |
| 9,120,862 B2 | 9/2015 | Yoshimura et al. |
| 9,121,066 B2 | 9/2015 | Hamamah et al. |
| 9,127,035 B2 | 9/2015 | Auclair et al. |
| 9,133,343 B2 | 9/2015 | Patton et al. |
| 9,139,860 B2 | 9/2015 | Chun |
| 9,145,575 B2 | 9/2015 | Liu et al. |
| RE45,763 E | 10/2015 | Brophy et al. |
| 9,163,283 B2 | 10/2015 | Chee et al. |
| 9,169,478 B2 | 10/2015 | Weiner et al. |
| 9,170,197 B2 | 10/2015 | Geddes et al. |
| 9,175,275 B2 | 11/2015 | Gray et al. |
| 9,175,348 B2 | 11/2015 | Korlach et al. |
| 9,186,643 B2 | 11/2015 | Griffiths et al. |
| 9,206,482 B2 | 12/2015 | Davicioni et al. |
| 9,212,379 B2 | 12/2015 | Tsang et al. |
| 9,213,027 B2 | 12/2015 | Doranz et al. |
| 9,243,017 B2 | 1/2016 | Aslan |
| 9,243,275 B1 | 1/2016 | Levon et al. |
| 9,249,400 B2 | 2/2016 | Gray et al. |
| 9,260,494 B2 | 2/2016 | Skerra et al. |
| 9,260,505 B2 | 2/2016 | Weir et al. |
| 9,265,815 B2 | 2/2016 | Fraser et al. |
| 9,265,844 B2 | 2/2016 | Tung et al. |
| 9,273,089 B2 | 3/2016 | Knutson et al. |
| 9,279,148 B2 | 3/2016 | Gunderson et al. |
| 9,279,770 B2 | 3/2016 | Mossoba et al. |
| 9,290,568 B2 | 3/2016 | Rives et al. |
| 9,296,797 B2 | 3/2016 | Ulijasz et al. |
| 9,309,545 B2 | 4/2016 | Medoff |
| 9,315,538 B2 | 4/2016 | Carter et al. |
| 9,315,868 B2 | 4/2016 | Vogelstein et al. |
| 9,340,568 B2 | 5/2016 | Casteel et al. |
| 9,347,092 B2 | 5/2016 | Roesler et al. |
| 9,347,863 B2 | 5/2016 | Mehrpouyan et al. |
| 9,365,623 B2 | 6/2016 | Ulijasz et al. |
| 9,365,883 B2 | 6/2016 | Gannot et al. |
| 9,371,357 B2 | 6/2016 | Sandrock et al. |
| 9,388,047 B2 | 7/2016 | Busnaina et al. |
| 9,388,373 B2 | 7/2016 | Rao et al. |
| 9,399,059 B2 | 7/2016 | Morrison |
| 9,399,763 B2 | 7/2016 | Weiner et al. |
| 9,399,795 B2 | 7/2016 | Chee et al. |
| 9,410,950 B2 | 8/2016 | Cui et al. |
| 9,439,976 B2 | 9/2016 | Tung et al. |
| 9,458,225 B2 | 10/2016 | Hassan Abdalla |
| 9,458,510 B2 | 10/2016 | DePinho et al. |
| 9,464,109 B2 | 10/2016 | Li et al. |
| 9,481,908 B2 | 11/2016 | Olasagasti et al. |
| 9,488,660 B2 | 11/2016 | Miao et al. |
| 9,493,513 B2 | 11/2016 | Mehmet et al. |
| 9,493,845 B2 | 11/2016 | Cao et al. |
| 9,506,867 B2 | 11/2016 | Moretto et al. |
| 9,512,469 B2 | 12/2016 | Seligmann et al. |
| 9,517,275 B2 | 12/2016 | Kibbe et al. |
| 9,518,077 B2 | 12/2016 | Halada et al. |
| 9,518,280 B2 | 12/2016 | Burke et al. |
| 9,518,986 B2 | 12/2016 | Blackburn et al. |
| 9,539,763 B2 | 1/2017 | Houbertz-Krauss et al. |
| 9,540,657 B2 | 1/2017 | Yu et al. |
| 9,551,025 B2 | 1/2017 | Kim et al. |
| 9,551,667 B2 | 1/2017 | Schmidt et al. |
| 9,556,429 B2 | 1/2017 | Mir |
| 9,579,346 B2 | 2/2017 | McGrath et al. |
| 9,598,479 B2 | 3/2017 | Rademacher et al. |
| 9,598,690 B2 | 3/2017 | Sun et al. |
| 9,603,775 B2 | 3/2017 | Weeks et al. |

(56) References Cited

U.S. PATENT DOCUMENTS

| | | |
|---|---|---|
| 9,620,727 B2 | 4/2017 | Laaksonen et al. |
| 9,624,271 B2 | 4/2017 | Hanko et al. |
| 9,624,307 B2 | 4/2017 | Nahrendorf et al. |
| 9,624,520 B2 | 4/2017 | Geierstanger et al. |
| 9,624,547 B2 | 4/2017 | Wong et al. |
| 9,637,441 B2 | 5/2017 | Miao et al. |
| 9,649,383 B2 | 5/2017 | Kashi et al. |
| 9,657,333 B2 | 5/2017 | Takoh |
| 9,657,360 B2 | 5/2017 | Stewart et al. |
| 9,677,107 B2 | 6/2017 | Reitmeir et al. |
| 9,689,039 B2 | 6/2017 | Wong et al. |
| 9,689,801 B2 | 6/2017 | Kho et al. |
| 9,700,485 B2 | 7/2017 | Weeks et al. |
| 9,700,486 B2 | 7/2017 | Weeks et al. |
| 9,701,709 B2 | 7/2017 | Anderson et al. |
| 9,707,154 B2 | 7/2017 | Weeks et al. |
| 9,707,155 B2 | 7/2017 | Weeks et al. |
| 9,708,667 B2 | 7/2017 | Yanai et al. |
| 9,713,572 B2 | 7/2017 | Weeks et al. |
| 9,717,648 B2 | 8/2017 | Weeks et al. |
| 9,717,649 B2 | 8/2017 | Weeks et al. |
| 9,718,894 B2 | 8/2017 | Choi et al. |
| 9,719,079 B2 | 8/2017 | Weiner et al. |
| 9,764,953 B2 | 9/2017 | Zuckermann et al. |
| 9,765,319 B2 | 9/2017 | Steer et al. |
| 9,782,443 B2 | 10/2017 | Pei et al. |
| 9,808,526 B2 | 11/2017 | Chen |
| 9,809,846 B2 | 11/2017 | Willner et al. |
| 9,823,253 B2 | 11/2017 | Weidemaier et al. |
| 9,829,437 B2 | 11/2017 | Chau et al. |
| 9,844,594 B2 | 12/2017 | Antochshuk et al. |
| 9,849,172 B2 | 12/2017 | Garcia-Sastre et al. |
| 9,856,505 B2 | 1/2018 | Bartko |
| 9,862,974 B2 | 1/2018 | Wang et al. |
| 9,868,937 B2 | 1/2018 | Regnier et al. |
| 9,873,866 B2 | 1/2018 | Darzins et al. |
| 9,879,299 B2 | 1/2018 | Yamakawa et al. |
| 9,885,716 B2 | 2/2018 | Lee et al. |
| 9,889,098 B2 | 2/2018 | Birbara |
| 9,890,208 B2 | 2/2018 | Brooks et al. |
| 9,896,733 B2 | 2/2018 | Kok et al. |
| 9,908,929 B2 | 3/2018 | Smith et al. |
| 9,913,899 B2 | 3/2018 | Kauvar et al. |
| 9,914,959 B2 | 3/2018 | Hildebrandt et al. |
| 9,932,365 B2 | 4/2018 | Kelts et al. |
| 9,937,152 B2 | 4/2018 | Maeda et al. |
| 9,938,525 B2 | 4/2018 | Carmona Orozco et al. |
| 9,944,918 B2 | 4/2018 | Venditti et al. |
| 9,951,125 B2 | 4/2018 | Barghorn et al. |
| 9,968,627 B2 | 5/2018 | Stahly et al. |
| 9,980,911 B2 | 5/2018 | Barnett et al. |
| 9,993,590 B2 | 6/2018 | Courtney et al. |
| 10,000,788 B2 | 6/2018 | Straus |
| 10,040,862 B2 | 8/2018 | Liu et al. |
| 10,040,868 B2 | 8/2018 | Sagi et al. |
| 10,052,393 B2 | 8/2018 | Park et al. |
| 10,059,994 B2 | 8/2018 | Hamamah et al. |
| 10,067,051 B2 | 9/2018 | Diem et al. |
| 10,071,163 B2 | 9/2018 | Montefeltro et al. |
| 10,088,481 B2 | 10/2018 | Scholl et al. |
| 10,100,299 B2 | 10/2018 | Slupska et al. |
| 10,101,209 B2 | 10/2018 | Selker et al. |
| 10,125,195 B2 | 11/2018 | Depaz et al. |
| 10,156,546 B2 | 12/2018 | Trau et al. |
| 10,174,069 B2 | 1/2019 | Field et al. |
| 10,174,329 B2 | 1/2019 | Deng et al. |
| 10,179,806 B2 | 1/2019 | Garcia-Sastre et al. |
| 10,183,969 B2 | 1/2019 | Kyhse-Andersen et al. |
| 10,202,428 B2 | 2/2019 | Cary et al. |
| 10,209,260 B2 | 2/2019 | Oved et al. |
| 10,220,098 B2 | 3/2019 | Kim et al. |
| 10,220,378 B2 | 3/2019 | Rozhkova et al. |
| 10,246,493 B2 | 4/2019 | Demirel et al. |
| 10,246,744 B2 | 4/2019 | Vijayan et al. |
| 10,253,144 B2 | 4/2019 | Demirel et al. |
| 10,261,020 B2 | 4/2019 | Tedesco et al. |
| 10,273,530 B2 | 4/2019 | Rimseliene et al. |
| 10,287,601 B2 | 5/2019 | Anterola |
| 10,294,133 B2 | 5/2019 | Hashim et al. |
| 10,294,515 B2 | 5/2019 | Seligmann et al. |
| 10,308,920 B2 | 6/2019 | Bornscheuer et al. |
| 10,328,100 B2 | 6/2019 | Bentov et al. |
| 10,338,078 B2 | 7/2019 | Sodeoka et al. |
| 10,344,336 B2 | 7/2019 | Bramlett et al. |
| 10,352,945 B2 | 7/2019 | Cohen et al. |
| 10,358,680 B2 | 7/2019 | Vo-Dinh et al. |
| 10,370,698 B2 | 8/2019 | Nolan et al. |
| 10,385,085 B2 | 8/2019 | Klopp et al. |
| 10,393,631 B2 | 8/2019 | Hsieh |
| 10,393,741 B2 | 8/2019 | Rikihisa |
| 10,413,482 B2 | 9/2019 | Weeks et al. |
| 10,416,155 B2 | 9/2019 | Dryga et al. |
| 10,441,667 B2 | 10/2019 | Perfect et al. |
| 10,538,581 B2 | 1/2020 | Barghorn et al. |
| 10,548,517 B2 | 2/2020 | Cho et al. |
| 10,548,953 B2 | 2/2020 | Liu et al. |
| 10,555,930 B2 | 2/2020 | Tang et al. |
| 10,563,163 B2 | 2/2020 | Berry et al. |
| 10,591,479 B2 | 3/2020 | Gao et al. |
| 10,604,745 B2 | 3/2020 | Darzins et al. |
| 10,625,250 B2 | 4/2020 | Hau |
| 10,640,772 B2 | 5/2020 | Furusho |
| 10,669,307 B2 | 6/2020 | Villain et al. |
| 10,677,805 B1 | 6/2020 | Chen et al. |
| 10,689,411 B2 | 6/2020 | Migaud et al. |
| 10,689,412 B2 | 6/2020 | Ju et al. |
| 10,711,319 B2 | 7/2020 | Einen et al. |
| 10,712,310 B2 | 7/2020 | Pleshko et al. |
| 10,716,789 B2 | 7/2020 | Nti-Addae et al. |
| 10,731,141 B2 | 8/2020 | Iyidogan |
| 10,736,956 B2 | 8/2020 | Palese et al. |
| 10,745,750 B2 | 8/2020 | Korlach et al. |
| 10,751,423 B2 | 8/2020 | Ghoroghchian et al. |
| 10,774,304 B2 | 9/2020 | Rao et al. |
| 10,781,256 B2 | 9/2020 | Weiskopf et al. |
| 10,786,545 B2 | 9/2020 | Kang et al. |
| 10,787,494 B2 | 9/2020 | Struthers et al. |
| 10,800,856 B2 | 10/2020 | Barnett et al. |
| 10,813,980 B2 | 10/2020 | Carelli et al. |
| 10,844,094 B2 | 11/2020 | Skerra et al. |
| 10,844,118 B2 | 11/2020 | Winau et al. |
| 10,870,875 B2 | 12/2020 | Sutherland et al. |
| 10,894,121 B2 | 1/2021 | Cheng et al. |
| 10,899,803 B2 | 1/2021 | Guerette et al. |
| 10,913,779 B2 | 2/2021 | Hall et al. |
| 10,918,126 B2 | 2/2021 | Shchepinov |
| 10,918,319 B2 | 2/2021 | Lee et al. |
| 10,919,979 B2 | 2/2021 | Magliery et al. |
| 10,953,073 B2 | 3/2021 | Schellenberger et al. |
| 10,962,512 B2 | 3/2021 | Zografos et al. |
| 10,975,427 B2 | 4/2021 | Dambacher et al. |
| 10,981,980 B2 | 4/2021 | Hall et al. |
| 11,007,849 B2 | 5/2021 | Csordas et al. |
| 11,015,220 B2 | 5/2021 | Nikiforov et al. |
| 11,022,611 B2 | 6/2021 | Robinson et al. |
| 11,026,885 B2 | 6/2021 | Ashton et al. |
| 11,026,963 B2 | 6/2021 | Gallop et al. |
| 11,034,743 B1 | 6/2021 | Lanquar et al. |
| 11,040,107 B2 | 6/2021 | Grossi et al. |
| 11,058,639 B2 | 7/2021 | Dizerega et al. |
| 11,072,797 B1 | 7/2021 | Lanquar et al. |
| 11,073,509 B2 | 7/2021 | Laing et al. |
| 11,079,388 B2 | 8/2021 | Chen |
| 11,090,385 B2 | 8/2021 | Peyman |
| 11,091,534 B2 | 8/2021 | Chhabra et al. |
| 11,111,603 B2 | 9/2021 | Jackson et al. |
| 11,124,543 B2 | 9/2021 | Berger et al. |
| 11,130,787 B2 | 9/2021 | Keller et al. |
| 11,249,026 B2 | 2/2022 | Moretto et al. |
| 11,358,984 B2 | 6/2022 | Passno et al. |
| 2004/0057040 A1 | 3/2004 | Beckenkamp et al. |
| 2004/0249122 A1 | 12/2004 | Blazyk |
| 2006/0240489 A1 | 10/2006 | Wei et al. |
| 2006/0281068 A1 | 12/2006 | Maier et al. |

(56) References Cited

U.S. PATENT DOCUMENTS

| | | |
|---|---|---|
| 2007/0122803 A1 | 5/2007 | Moore et al. |
| 2009/0104594 A1 | 4/2009 | Webb |
| 2009/0275020 A1 | 11/2009 | Faure |
| 2010/0136609 A1 | 6/2010 | Clay et al. |
| 2010/0203050 A1 | 8/2010 | Weik et al. |
| 2010/0203651 A1 | 8/2010 | Lim et al. |
| 2010/0256336 A1 | 10/2010 | Yuk et al. |
| 2010/0291599 A1 | 11/2010 | Tague, Jr. et al. |
| 2011/0081672 A1 | 4/2011 | Andersen et al. |
| 2012/0122076 A1* | 5/2012 | Lau .................... C07K 1/14 530/416 |
| 2012/0123688 A1* | 5/2012 | Ramasubramanyan .................... G01N 33/6854 702/19 |
| 2012/0275681 A1 | 11/2012 | Honda et al. |
| 2013/0177919 A1 | 7/2013 | Kaufmann et al. |
| 2013/0177972 A1 | 7/2013 | Green et al. |
| 2014/0087423 A1 | 3/2014 | Koncilja et al. |
| 2014/0150855 A1 | 6/2014 | Inoue et al. |
| 2014/0335630 A1 | 11/2014 | Cameron et al. |
| 2015/0110799 A1 | 4/2015 | Ramasubramanyan et al. |
| 2015/0183862 A1 | 7/2015 | Edwards et al. |
| 2015/0247210 A1 | 9/2015 | Olesberg et al. |
| 2015/0328563 A1 | 11/2015 | Lacki et al. |
| 2016/0000891 A1 | 1/2016 | Barghorn et al. |
| 2016/0025633 A1 | 1/2016 | Moretto et al. |
| 2016/0069809 A1 | 3/2016 | Bonnier et al. |
| 2016/0103072 A1 | 4/2016 | Fukutake et al. |
| 2016/0159888 A1 | 6/2016 | Klingelhofer et al. |
| 2016/0215103 A1 | 7/2016 | Omenetto et al. |
| 2016/0251408 A1 | 9/2016 | Chhabra et al. |
| 2016/0341667 A1 | 11/2016 | Ramasubramanyan et al. |
| 2017/0073393 A1 | 3/2017 | Chhabra et al. |
| 2017/0130186 A1 | 5/2017 | Berry et al. |
| 2017/0189550 A1 | 7/2017 | Puebla et al. |
| 2017/0299594 A1 | 10/2017 | Depinho et al. |
| 2017/0333559 A1 | 11/2017 | Sloey et al. |
| 2017/0355947 A9 | 12/2017 | Berry et al. |
| 2018/0000146 A1 | 1/2018 | Geremia |
| 2018/0003712 A1 | 1/2018 | Haam et al. |
| 2018/0020956 A1 | 1/2018 | Lee et al. |
| 2018/0023111 A1 | 1/2018 | Schutze et al. |
| 2018/0034051 A1 | 2/2018 | Whelan et al. |
| 2018/0051063 A1 | 2/2018 | Cleland et al. |
| 2018/0071376 A1 | 3/2018 | Bornal et al. |
| 2018/0087041 A1 | 3/2018 | Venditti |
| 2018/0125988 A1 | 5/2018 | Yang et al. |
| 2018/0126001 A1 | 5/2018 | Malecki et al. |
| 2018/0127813 A1 | 5/2018 | Haushalter |
| 2018/0133319 A1 | 5/2018 | Vo-Dinh et al. |
| 2018/0135121 A1 | 5/2018 | Ju et al. |
| 2018/0149597 A1 | 5/2018 | Umezaki et al. |
| 2018/0155336 A1 | 6/2018 | Mais et al. |
| 2018/0177891 A1 | 6/2018 | McAteer et al. |
| 2018/0180549 A1 | 6/2018 | Lewis |
| 2018/0185518 A1 | 7/2018 | Vitaliano et al. |
| 2018/0217146 A1 | 8/2018 | Varadarajan et al. |
| 2018/0222938 A1 | 8/2018 | Herigstad et al. |
| 2018/0237501 A1 | 8/2018 | Sloey et al. |
| 2018/0256740 A1 | 9/2018 | Pasqualini et al. |
| 2018/0258484 A1 | 9/2018 | Gros |
| 2018/0284134 A1 | 10/2018 | Basadonna et al. |
| 2018/0291329 A1 | 10/2018 | Moretto et al. |
| 2018/0292324 A1 | 10/2018 | Verma et al. |
| 2018/0305417 A1 | 10/2018 | Spudich et al. |
| 2018/0327828 A1 | 11/2018 | Ju et al. |
| 2019/0000988 A1 | 1/2019 | Chen |
| 2019/0008965 A1 | 1/2019 | Messersmith et al. |
| 2019/0009241 A1 | 1/2019 | Prewer |
| 2019/0024261 A1 | 1/2019 | Griffiths et al. |
| 2019/0034597 A1 | 1/2019 | Tsumoto et al. |
| 2019/0062419 A1 | 2/2019 | Ramasubramanyan et al. |
| 2019/0077850 A1 | 3/2019 | Ingber et al. |
| 2019/0083402 A1 | 3/2019 | Talley |
| 2019/0106461 A1 | 4/2019 | Garcia-Sastre et al. |
| 2019/0112569 A1 | 4/2019 | Czeterko et al. |
| 2019/0120824 A1 | 4/2019 | Jaques et al. |
| 2019/0125859 A1 | 5/2019 | Palese et al. |
| 2019/0135878 A1 | 5/2019 | Silberg et al. |
| 2019/0137338 A1 | 5/2019 | Webster et al. |
| 2019/0142921 A1 | 5/2019 | Delisa et al. |
| 2019/0144284 A1 | 5/2019 | Blanford et al. |
| 2019/0153115 A1 | 5/2019 | Schellenberger et al. |
| 2019/0153381 A1 | 5/2019 | Angelini et al. |
| 2019/0153527 A1 | 5/2019 | Ju et al. |
| 2019/0162726 A1 | 5/2019 | Hawksworth et al. |
| 2019/0177435 A1 | 6/2019 | Wong et al. |
| 2019/0194460 A1 | 6/2019 | Ceres et al. |
| 2019/0201556 A1 | 7/2019 | McLeay |
| 2019/0209715 A1 | 7/2019 | Kelly et al. |
| 2019/0255106 A1 | 8/2019 | Lande et al. |
| 2019/0255173 A1 | 8/2019 | Francis et al. |
| 2019/0263914 A1 | 8/2019 | Brogdon et al. |
| 2019/0270769 A1 | 9/2019 | Milano et al. |
| 2019/0272894 A1 | 9/2019 | Wasalathanthri et al. |
| 2019/0275104 A1 | 9/2019 | Lande et al. |
| 2019/0276528 A1 | 9/2019 | Liu et al. |
| 2019/0298826 A1 | 10/2019 | Hoos et al. |
| 2019/0309045 A1 | 10/2019 | Yun |
| 2019/0315835 A1 | 10/2019 | Schellenberger et al. |
| 2019/0316208 A1 | 10/2019 | Hanks et al. |
| 2019/0338039 A1 | 11/2019 | Barnett et al. |
| 2019/0339272 A1 | 11/2019 | Campbell et al. |
| 2019/0352430 A1 | 11/2019 | Demirel et al. |
| 2019/0352598 A1 | 11/2019 | Sabatini et al. |
| 2019/0374617 A1 | 12/2019 | Hall et al. |
| 2019/0375822 A1 | 12/2019 | Seth Chhabra et al. |
| 2019/0376020 A1 | 12/2019 | Bickham et al. |
| 2019/0381129 A1 | 12/2019 | Grossi et al. |
| 2019/0381182 A1 | 12/2019 | Dutta et al. |
| 2020/0024363 A1 | 1/2020 | Teran et al. |
| 2020/0031863 A1 | 1/2020 | Muller-Spath et al. |
| 2020/0032248 A1 | 1/2020 | White |
| 2020/0038352 A1 | 2/2020 | Yoon et al. |
| 2020/0062832 A1 | 2/2020 | Sun et al. |
| 2020/0069717 A1 | 3/2020 | Ju et al. |
| 2020/0087379 A1 | 3/2020 | Schellenberger et al. |
| 2020/0087632 A1 | 3/2020 | Coffman et al. |
| 2020/0096448 A1 | 3/2020 | Gillner et al. |
| 2020/0108072 A1 | 4/2020 | Honigberg et al. |
| 2020/0116638 A1 | 4/2020 | Duraipandian et al. |
| 2020/0131265 A1 | 4/2020 | Koenig et al. |
| 2020/0147175 A1 | 5/2020 | Schillaci |
| 2020/0148999 A1 | 5/2020 | Beckers et al. |
| 2020/0150022 A1 | 5/2020 | Ugawa et al. |
| 2020/0157141 A1 | 5/2020 | Sharnez et al. |
| 2020/0200763 A1 | 6/2020 | Min et al. |
| 2020/0231944 A1 | 7/2020 | Budge et al. |
| 2020/0239852 A1 | 7/2020 | Hiller et al. |
| 2020/0241002 A1 | 7/2020 | Xu |
| 2020/0251186 A1 | 8/2020 | Love et al. |
| 2020/0254093 A1 | 8/2020 | Khandekar et al. |
| 2020/0254118 A1 | 8/2020 | Bachawal et al. |
| 2020/0255538 A1 | 8/2020 | Magliery et al. |
| 2020/0270354 A1 | 8/2020 | Khandekar et al. |
| 2020/0283506 A1 | 9/2020 | Watters et al. |
| 2020/0283713 A1 | 9/2020 | Ball et al. |
| 2020/0291075 A1 | 9/2020 | Toettcher et al. |
| 2020/0292538 A1 | 9/2020 | Olivo et al. |
| 2020/0297855 A1 | 9/2020 | Leach et al. |
| 2020/0316163 A1 | 10/2020 | Grossi et al. |
| 2020/0325460 A1 | 10/2020 | Skirgaila et al. |
| 2020/0347088 A1 | 11/2020 | Jiang et al. |
| 2020/0352857 A1 | 11/2020 | Gu et al. |
| 2020/0354414 A1 | 11/2020 | Zhang et al. |
| 2020/0354459 A1 | 11/2020 | Pearse et al. |
| 2020/0361996 A1 | 11/2020 | Pochan et al. |
| 2020/0362017 A1 | 11/2020 | Popel et al. |
| 2020/0363416 A1 | 11/2020 | Yang et al. |
| 2020/0369607 A1 | 11/2020 | Reuveni et al. |
| 2020/0370133 A1 | 11/2020 | Kim et al. |
| 2020/0385469 A1 | 12/2020 | Yang et al. |
| 2020/0385757 A1 | 12/2020 | Kahvejian et al. |
| 2020/0390908 A1 | 12/2020 | Singh et al. |

(56) References Cited

U.S. PATENT DOCUMENTS

| | | |
|---|---|---|
| 2020/0392195 A1 | 12/2020 | Schellenberger et al. |
| 2020/0392447 A1 | 12/2020 | Berry et al. |
| 2020/0399398 A1 | 12/2020 | Bangera et al. |
| 2021/0002335 A1 | 1/2021 | Omenetto et al. |
| 2021/0002387 A1 | 1/2021 | Geremia et al. |
| 2021/0002628 A1 | 1/2021 | Federowicz et al. |
| 2021/0009935 A1 | 1/2021 | Saito et al. |
| 2021/0015962 A1 | 1/2021 | Shaffer et al. |
| 2021/0017226 A1 | 1/2021 | Baek |
| 2021/0017553 A1 | 1/2021 | Hiller et al. |
| 2021/0024872 A1 | 1/2021 | Martin et al. |
| 2021/0025004 A1 | 1/2021 | Gleeson et al. |
| 2021/0025814 A1 | 1/2021 | Stacey et al. |
| 2021/0025887 A1 | 1/2021 | Broger |
| 2021/0032289 A1 | 2/2021 | Francois et al. |
| 2021/0032616 A1 | 2/2021 | Liu et al. |
| 2021/0040064 A1 | 2/2021 | Fernandez et al. |
| 2021/0040431 A1 | 2/2021 | Mogi |
| 2021/0047606 A1 | 2/2021 | Ray et al. |
| 2021/0054068 A1 | 2/2021 | Abou-Elkacem et al. |
| 2021/0054093 A1 | 2/2021 | Wang et al. |
| 2021/0061854 A1 | 3/2021 | Olmstead et al. |
| 2021/0062133 A1 | 3/2021 | Hassell et al. |
| 2021/0062143 A1 | 3/2021 | Hermiston et al. |
| 2021/0069334 A1 | 3/2021 | Li et al. |
| 2021/0070842 A1 | 3/2021 | Fraser et al. |
| 2021/0071016 A1 | 3/2021 | Zhong et al. |
| 2021/0071249 A1 | 3/2021 | Irani et al. |
| 2021/0077518 A1 | 3/2021 | Poe et al. |
| 2021/0087535 A1 | 3/2021 | Lawrence et al. |
| 2021/0094982 A1 | 4/2021 | Ludemann-Hombourger et al. |
| 2021/0095019 A1 | 4/2021 | Wang et al. |
| 2021/0100785 A1 | 4/2021 | Stahly et al. |
| 2021/0101974 A1 | 4/2021 | Zhang |
| 2021/0106681 A1 | 4/2021 | Duroux et al. |
| 2021/0107956 A1 | 4/2021 | Brozik et al. |
| 2021/0121504 A1 | 4/2021 | Whitfill |
| 2021/0128684 A1 | 5/2021 | Dianzani et al. |
| 2021/0130182 A1 | 5/2021 | Vertelova et al. |
| 2021/0130294 A1 | 5/2021 | Michael et al. |
| 2021/0139533 A1 | 5/2021 | Mearns Spragg |
| 2021/0139976 A1 | 5/2021 | Ju et al. |
| 2021/0145831 A1 | 5/2021 | Cui et al. |
| 2021/0154237 A1 | 5/2021 | Beard et al. |
| 2021/0155656 A1 | 5/2021 | Falkenstein et al. |
| 2021/0155677 A1 | 5/2021 | Ingber et al. |
| 2021/0164011 A1 | 6/2021 | Schellenberger et al. |
| 2021/0170012 A1 | 6/2021 | Nizet et al. |
| 2021/0188976 A1 | 6/2021 | Chalons-Cottavoz et al. |
| 2021/0208139 A1 | 7/2021 | Sasso |
| 2021/0220297 A1 | 7/2021 | Reuveni et al. |
| 2021/0220483 A1 | 7/2021 | Davis et al. |
| 2021/0228619 A1 | 7/2021 | Peyman |
| 2021/0230210 A1 | 7/2021 | Olhava |
| 2021/0230592 A1 | 7/2021 | Scheinberg et al. |
| 2021/0238045 A1 | 8/2021 | Favaro et al. |
| 2021/0238259 A1 | 8/2021 | Van Der Flier et al. |
| 2021/0246206 A1 | 8/2021 | Liu et al. |
| 2021/0246212 A1 | 8/2021 | Salas et al. |
| 2021/0260113 A1 | 8/2021 | Kholin et al. |
| 2021/0260201 A1 | 8/2021 | Chukly et al. |
| 2021/0261607 A1 | 8/2021 | Zhu et al. |
| 2021/0261655 A1 | 8/2021 | Bannister et al. |
| 2021/0269522 A1 | 9/2021 | Wang et al. |
| 2021/0277056 A1 | 9/2021 | Miao et al. |
| 2021/0277074 A1 | 9/2021 | Schellenberger et al. |
| 2021/0277079 A1 | 9/2021 | Watters et al. |
| 2021/0277377 A1 | 9/2021 | Jacky et al. |
| 2021/0283233 A1 | 9/2021 | Kurtis et al. |
| 2021/0283235 A1 | 9/2021 | Curtiss, III et al. |
| 2021/0284684 A1 | 9/2021 | Tustian et al. |
| 2021/0299154 A1 | 9/2021 | Gallop et al. |
| 2022/0259532 A1 | 8/2022 | Raberg et al. |
| 2022/0299370 A1 | 9/2022 | Hu et al. |

FOREIGN PATENT DOCUMENTS

| | | |
|---|---|---|
| AU | 2002363062 B2 | 3/2007 |
| AU | 2007202906 A1 | 7/2007 |
| AU | 2002355997 B2 | 1/2008 |
| AU | 2012200864 A1 | 3/2012 |
| AU | 2012201856 A1 | 4/2012 |
| AU | 2012244255 A1 | 11/2012 |
| AU | 2013201114 A1 | 3/2013 |
| AU | 2013201117 A1 | 3/2013 |
| AU | 2013201308 B2 | 5/2013 |
| AU | 2013202463 A1 | 5/2013 |
| AU | 2013203326 B2 | 5/2013 |
| AU | 2013204082 A1 | 5/2013 |
| AU | 2013204086 B2 | 5/2013 |
| AU | 2013221356 A1 | 8/2014 |
| AU | 2017200870 A1 | 3/2017 |
| AU | 2016334247 A1 | 4/2018 |
| AU | 2018350890 A1 | 3/2020 |
| BR | 102012033580 A2 | 6/2015 |
| BR | PI1004360 A2 | 8/2015 |
| BR | 102016017022 B1 | 2/2018 |
| BR | 132013030798 E2 | 7/2019 |
| CA | 2243943 A1 | 7/1997 |
| CA | 2843504 A1 | 2/2013 |
| CA | 2809872 A1 | 9/2013 |
| CA | 2882003 A1 | 2/2014 |
| CA | 2849447 A1 | 10/2014 |
| CA | 2915653 A1 | 10/2014 |
| CA | 2884907 A1 | 5/2015 |
| CA | 2953020 A1 | 12/2015 |
| CA | 2943103 A1 | 3/2018 |
| CA | 3078956 A1 | 4/2019 |
| CA | 2811493 C | 6/2020 |
| CN | 1218960 A | 6/1999 |
| CN | 101285069 A | 10/2008 |
| CN | 101469333 A | 7/2009 |
| CN | 101482509 A | 7/2009 |
| CN | 101482554 A | 7/2009 |
| CN | 101605457 A | 12/2009 |
| CN | 101208353 B | 12/2011 |
| CN | 102875623 A | 1/2013 |
| CN | 103097411 A | 5/2013 |
| CN | 103124738 A | 5/2013 |
| CN | 103145777 A | 6/2013 |
| CN | 103923169 A | 7/2014 |
| CN | 103958491 A | 7/2014 |
| CN | 104152519 A | 11/2014 |
| CN | 104297225 A | 1/2015 |
| CN | 104774756 A | 7/2015 |
| CN | 105273079 A | 1/2016 |
| CN | 105738343 A | 7/2016 |
| CN | 105899658 A | 8/2016 |
| CN | 105934522 A | 9/2016 |
| CN | 106295251 A | 1/2017 |
| CN | 106460069 A | 2/2017 |
| CN | 106645079 A | 5/2017 |
| CN | 106674294 A | 5/2017 |
| CN | 106749523 A | 5/2017 |
| CN | 106769693 A | 5/2017 |
| CN | 107226840 A | 10/2017 |
| CN | 107266569 A | 10/2017 |
| CN | 107383193 A | 11/2017 |
| CN | 107541533 A | 1/2018 |
| CN | 107722109 A | 2/2018 |
| CN | 107778336 A | 3/2018 |
| CN | 107824800 A | 3/2018 |
| CN | 108037107 A | 5/2018 |
| CN | 108169203 A | 6/2018 |
| CN | 108239123 A | 7/2018 |
| CN | 108267437 A | 7/2018 |
| CN | 108459001 A | 8/2018 |
| CN | 108659118 A | 10/2018 |
| CN | 108660185 A | 10/2018 |
| CN | 108699568 A | 10/2018 |
| CN | 108727486 A | 11/2018 |
| CN | 108732145 A | 11/2018 |
| CN | 109266717 A | 1/2019 |
| CN | 109342393 A | 2/2019 |

(56) References Cited

FOREIGN PATENT DOCUMENTS

| | | |
|---|---|---|
| CN | 109342403 A | 2/2019 |
| CN | 109354597 A | 2/2019 |
| CN | 109536474 A | 3/2019 |
| CN | 109553662 A | 4/2019 |
| CN | 109627328 A | 4/2019 |
| CN | 110078734 A | 8/2019 |
| CN | 110117575 A | 8/2019 |
| CN | 110144330 A | 8/2019 |
| CN | 110208238 A | 9/2019 |
| CN | 110248951 A | 9/2019 |
| CN | 110286240 A | 9/2019 |
| CN | 110358739 A | 10/2019 |
| CN | 209460143 U | 10/2019 |
| CN | 110441287 A | 11/2019 |
| CN | 110501319 A | 11/2019 |
| CN | 110646401 A | 1/2020 |
| CN | 110669147 A | 1/2020 |
| CN | 110804089 A | 2/2020 |
| CN | 111153990 A | 5/2020 |
| CN | 111194221 A | 5/2020 |
| CN | 111201434 A | 5/2020 |
| CN | 111215141 A | 6/2020 |
| CN | 111220589 A | 6/2020 |
| CN | 111220590 A | 6/2020 |
| CN | 111289489 A | 6/2020 |
| CN | 111433592 A | 7/2020 |
| CN | 111454349 A | 7/2020 |
| CN | 111542507 A | 8/2020 |
| CN | 111569939 A | 8/2020 |
| CN | 111662879 A | 9/2020 |
| CN | 111763658 A | 10/2020 |
| CN | 111888341 A | 11/2020 |
| CN | 111912826 A | 11/2020 |
| CN | 111944027 A | 11/2020 |
| CN | 112014372 A | 12/2020 |
| CN | 112138644 A | 12/2020 |
| CN | 112279909 A | 1/2021 |
| CN | 112375754 A | 2/2021 |
| CN | 112409933 A | 2/2021 |
| CN | 112458062 A | 3/2021 |
| CN | 112521455 A | 3/2021 |
| CN | 112639456 A | 4/2021 |
| CN | 112725407 A | 4/2021 |
| CN | 112834749 A | 5/2021 |
| CN | 112979784 A | 6/2021 |
| CN | 112979814 A | 6/2021 |
| CN | 112979815 A | 6/2021 |
| CN | 113004392 A | 6/2021 |
| CN | 113045663 A | 6/2021 |
| CN | 113173994 A | 7/2021 |
| CN | 113214358 A | 8/2021 |
| CN | 113214399 A | 8/2021 |
| CN | 113234166 A | 8/2021 |
| CN | 113286884 A | 8/2021 |
| CN | 113354703 A | 9/2021 |
| CN | 113444721 A | 9/2021 |
| CN | 113454460 A | 9/2021 |
| CZ | 299996 B6 | 1/2009 |
| CZ | 29065 U1 | 1/2016 |
| CZ | 2015288 A3 | 11/2016 |
| CZ | 308447 B6 | 8/2020 |
| DE | 10217948 A1 | 11/2003 |
| EA | 006368 B1 | 12/2005 |
| EA | 007413 B1 | 10/2006 |
| EA | 009294 B1 | 12/2007 |
| EA | 017887 B1 | 3/2013 |
| EA | 026112 B1 | 3/2017 |
| EA | 028162 B1 | 10/2017 |
| EA | 032327 B1 | 5/2019 |
| EP | 2326955 A1 | 6/2011 |
| EP | 2707030 A1 | 3/2014 |
| EP | 2831587 A1 | 2/2015 |
| EP | 2972238 A1 | 1/2016 |
| EP | 3134104 A1 | 3/2017 |
| EP | 3380825 A1 | 10/2018 |
| EP | 3611495 A1 | 2/2020 |
| EP | 3709005 A1 | 9/2020 |
| ES | 2331781 A1 | 1/2010 |
| FR | 2964671 A1 | 3/2012 |
| GB | 2467494 A | 8/2010 |
| GB | 2485479 A | 5/2012 |
| JP | 5-76346 A | 3/1993 |
| JP | 2005-306827 A | 11/2005 |
| JP | 3885054 B2 | 2/2007 |
| JP | 2007-302569 A | 11/2007 |
| JP | 2007-530913 A | 11/2007 |
| JP | 2009-517002 A | 4/2009 |
| JP | 4250523 B2 | 4/2009 |
| JP | 2009-263273 A | 11/2009 |
| JP | 4502814 B2 | 7/2010 |
| JP | 4726196 B2 | 7/2011 |
| JP | 4786656 B2 | 10/2011 |
| JP | 4881356 B2 | 2/2012 |
| JP | 5117191 B2 | 1/2013 |
| JP | 2013-537235 A | 9/2013 |
| JP | 2013-541711 A | 11/2013 |
| JP | 2014-516996 A | 7/2014 |
| JP | 2016-512569 A | 4/2016 |
| JP | 2016-156807 A | 9/2016 |
| JP | 2016-531112 A | 10/2016 |
| JP | 6069224 B2 | 2/2017 |
| JP | 2018-502090 A | 1/2018 |
| JP | 2018-507180 A | 3/2018 |
| JP | 2018-063131 A | 4/2018 |
| JP | 2018-070626 A | 5/2018 |
| JP | 6348635 B2 | 6/2018 |
| JP | 6359559 B2 | 7/2018 |
| JP | 2018-138594 A | 9/2018 |
| JP | 2018-143137 A | 9/2018 |
| JP | 6386461 B2 | 9/2018 |
| JP | 2018-531398 A | 10/2018 |
| JP | 6402351 B2 | 10/2018 |
| JP | 2018-172403 A | 11/2018 |
| JP | 2018-532696 A | 11/2018 |
| JP | 2019-501658 A | 1/2019 |
| JP | 2019-038836 A | 3/2019 |
| JP | 2019-511582 A | 4/2019 |
| JP | 6495256 B2 | 4/2019 |
| JP | 2019-513723 A | 5/2019 |
| JP | 6522826 B2 | 5/2019 |
| JP | 6525872 B2 | 6/2019 |
| JP | 2019-108371 A | 7/2019 |
| JP | 2019-522799 A | 8/2019 |
| JP | 2019-163317 A | 9/2019 |
| JP | 6588039 B2 | 10/2019 |
| JP | 2019-208511 A | 12/2019 |
| JP | 2020-500157 A | 1/2020 |
| JP | 6637241 B2 | 1/2020 |
| JP | 2020-514278 A | 5/2020 |
| JP | 2020-521443 A | 7/2020 |
| JP | 6722697 B2 | 7/2020 |
| JP | 2020-523990 A | 8/2020 |
| JP | 2020-172517 A | 10/2020 |
| JP | 2020-180975 A | 11/2020 |
| JP | 2020-532497 A | 11/2020 |
| JP | 2020-532993 A | 11/2020 |
| JP | 2020-533582 A | 11/2020 |
| JP | 2020-536497 A | 12/2020 |
| JP | 2020-536521 A | 12/2020 |
| JP | 2020-537126 A | 12/2020 |
| JP | 6810461 B2 | 1/2021 |
| JP | 2021-048872 A | 4/2021 |
| JP | 6870087 B2 | 5/2021 |
| JP | 6873090 B2 | 5/2021 |
| JP | 2021-092573 A | 6/2021 |
| JP | 6908605 B2 | 7/2021 |
| JP | 2021-518145 A | 8/2021 |
| JP | 2021-521412 A | 8/2021 |
| JP | 6915224 B2 | 8/2021 |
| JP | 2021-524835 A | 9/2021 |
| KR | 100868248 B1 | 11/2008 |
| KR | 101227434 B1 | 1/2013 |
| KR | 101297667 B1 | 8/2013 |
| KR | 101360405 B1 | 2/2014 |

(56) References Cited

FOREIGN PATENT DOCUMENTS

| | | |
|---|---|---|
| KR | 101438047 B1 | 9/2014 |
| KR | 101496671 B1 | 3/2015 |
| KR | 101528440 B1 | 6/2015 |
| KR | 101558160 B1 | 10/2015 |
| KR | 101669954 B1 | 10/2016 |
| KR | 101798295 B1 | 11/2017 |
| KR | 20180043835 A | 4/2018 |
| KR | 101860436 B1 | 5/2018 |
| KR | 10-2018-0059739 A | 6/2018 |
| KR | 20180094877 A | 8/2018 |
| KR | 101907026 B1 | 10/2018 |
| KR | 101919427 B1 | 11/2018 |
| KR | 101927864 B1 | 12/2018 |
| KR | 20190009512 A | 1/2019 |
| KR | 10-2019-0054746 A | 5/2019 |
| KR | 101974733 B1 | 5/2019 |
| KR | 101979000 B1 | 5/2019 |
| KR | 102008608 B1 | 8/2019 |
| KR | 102012123 B1 | 8/2019 |
| KR | 102008609 B1 | 10/2019 |
| KR | 20190125891 A | 11/2019 |
| KR | 10-2020-0070218 A | 6/2020 |
| KR | 102169268 B1 | 10/2020 |
| KR | 102194995 B1 | 12/2020 |
| KR | 102196156 B1 | 12/2020 |
| KR | 102196159 B1 | 12/2020 |
| KR | 102202082 B1 | 1/2021 |
| KR | 102227251 B1 | 3/2021 |
| KR | 102227257 B1 | 3/2021 |
| KR | 102250446 B1 | 5/2021 |
| KR | 102252798 B1 | 5/2021 |
| KR | 20210061075 A | 5/2021 |
| KR | 20210073785 A | 6/2021 |
| RU | 2531754 C2 | 10/2014 |
| RU | 2589695 C2 | 7/2016 |
| RU | 2745511 C1 | 3/2021 |
| SG | 183721 A1 | 9/2012 |
| SG | 1120201127 T | 3/2020 |
| TW | 201249480 A | 12/2012 |
| TW | 1475209 B | 3/2015 |
| TW | 201529604 A | 8/2015 |
| TW | 201741461 A | 12/2017 |
| TW | 201928042 A | 7/2019 |
| TW | 202033949 A | 9/2020 |
| TW | 202043254 A | 12/2020 |
| TW | 202044131 A | 12/2020 |
| TW | I734166 B | 7/2021 |
| TW | 202128743 A | 8/2021 |
| TW | 202128745 A | 8/2021 |
| WO | WO-1997/036540 A1 | 10/1997 |
| WO | WO-2012/037430 A1 | 3/2012 |
| WO | WO-2012/040041 A1 | 3/2012 |
| WO | WO-2014/137291 A1 | 9/2014 |
| WO | WO-2014/170684 A1 | 10/2014 |
| WO | WO-2015/095255 A1 | 6/2015 |
| WO | WO-2015/145149 A1 | 10/2015 |
| WO | WO-2016/004322 A2 | 1/2016 |
| WO | WO-2016/060171 A1 | 4/2016 |
| WO | WO-2016/172350 A1 | 10/2016 |
| WO | WO-2016/196315 A2 | 12/2016 |
| WO | WO-2017/164815 A1 | 9/2017 |
| WO | WO-2018/028634 A1 | 2/2018 |
| WO | WO-2018/031954 A1 | 2/2018 |
| WO | WO-2018/034205 A1 | 2/2018 |
| WO | WO-2018/049372 A1 | 3/2018 |
| WO | WO-2018/058073 A2 | 3/2018 |
| WO | WO-2018/093777 A1 | 5/2018 |
| WO | WO-2018/103038 A1 | 6/2018 |
| WO | WO-2018/111941 A1 | 6/2018 |
| WO | WO-2018/132389 A1 | 7/2018 |
| WO | WO-2018/140041 A1 | 8/2018 |
| WO | WO-2018/156649 A1 | 8/2018 |
| WO | WO-2018/159833 A1 | 9/2018 |
| WO | WO-2018/175346 A1 | 9/2018 |
| WO | WO-2018/183876 A1 | 10/2018 |
| WO | WO-2018/188395 A1 | 10/2018 |
| WO | WO-2018/195134 A1 | 10/2018 |
| WO | WO-2018/195491 A1 | 10/2018 |
| WO | WO-2018/237327 A1 | 12/2018 |
| WO | WO-2019/028285 A2 | 2/2019 |
| WO | WO-2019/030377 A1 | 2/2019 |
| WO | WO-2019/032463 A1 | 2/2019 |
| WO | WO-2019/060685 A1 | 3/2019 |
| WO | WO-2019/062689 A1 | 4/2019 |
| WO | WO-2019/071076 A1 | 4/2019 |
| WO | WO-2019/079165 A1 | 4/2019 |
| WO | WO-2019/084512 A1 | 5/2019 |
| WO | WO-2019/117177 A1 | 6/2019 |
| WO | WO-2019/148140 A2 | 8/2019 |
| WO | WO-2019/157263 A1 | 8/2019 |
| WO | WO-2019/165105 A1 | 8/2019 |
| WO | WO-2019/165134 A1 | 8/2019 |
| WO | WO-2019/185860 A1 | 10/2019 |
| WO | WO-2019/204508 A1 | 10/2019 |
| WO | WO-2019/208594 A1 | 10/2019 |
| WO | WO-2019/211531 A1 | 11/2019 |
| WO | WO-2019/216288 A1 | 11/2019 |
| WO | WO-2019/236447 A1 | 12/2019 |
| WO | WO-2019/246013 A1 | 12/2019 |
| WO | WO-2020/007326 A1 | 1/2020 |
| WO | WO-2020/037117 A1 | 2/2020 |
| WO | WO-2020/038426 A1 | 2/2020 |
| WO | WO-2020/041200 A1 | 2/2020 |
| WO | WO-2020/081598 A1 | 4/2020 |
| WO | WO-2020/082061 A1 | 4/2020 |
| WO | WO-2020/086635 A1 | 4/2020 |
| WO | WO-2020/087040 A1 | 4/2020 |
| WO | WO-2020/090225 A1 | 5/2020 |
| WO | WO-2020/092835 A1 | 5/2020 |
| WO | WO-2020/096965 A1 | 5/2020 |
| WO | WO-2020/106997 A1 | 5/2020 |
| WO | WO-2020/108735 A1 | 6/2020 |
| WO | WO-2020/115196 A1 | 6/2020 |
| WO | WO-2020/115661 A1 | 6/2020 |
| WO | WO-2020/124271 A1 | 6/2020 |
| WO | WO-2020/131192 A2 | 6/2020 |
| WO | WO-2020/132074 A1 | 6/2020 |
| WO | WO-2020/150751 A2 | 7/2020 |
| WO | WO-2020/157752 A1 | 8/2020 |
| WO | WO-2020/160462 A1 | 8/2020 |
| WO | WO-2020/162601 A1 | 8/2020 |
| WO | WO-2020/180003 A1 | 9/2020 |
| WO | WO-2020/180534 A1 | 9/2020 |
| WO | WO-2020/186026 A1 | 9/2020 |
| WO | WO-2020/206055 A1 | 10/2020 |
| WO | WO-2020/210476 A1 | 10/2020 |
| WO | WO-2020/210836 A1 | 10/2020 |
| WO | WO-2020/213993 A1 | 10/2020 |
| WO | WO-2020/217895 A1 | 10/2020 |
| WO | WO-2020/218976 A1 | 10/2020 |
| WO | WO-2020/223125 A1 | 11/2020 |
| WO | WO-2020/226513 A1 | 11/2020 |
| WO | WO-2020/227571 A1 | 11/2020 |
| WO | WO-2020/237221 A1 | 11/2020 |
| WO | WO-2020/237304 A1 | 12/2020 |
| WO | WO-2020/238918 A1 | 12/2020 |
| WO | WO-2020/240024 A1 | 12/2020 |
| WO | WO-2020/247730 A1 | 12/2020 |
| WO | WO-2020/247952 A2 | 12/2020 |
| WO | WO-2020/251802 A1 | 12/2020 |
| WO | WO-2020/252266 A1 | 12/2020 |
| WO | WO-2020/252413 A1 | 12/2020 |
| WO | WO-2020/254176 A1 | 12/2020 |
| WO | WO-2020/260073 A1 | 12/2020 |
| WO | WO-2020/260229 A1 | 12/2020 |
| WO | WO-2020/261245 A1 | 12/2020 |
| WO | WO-2021/007111 A1 | 1/2021 |
| WO | WO-2021/007458 A1 | 1/2021 |
| WO | WO-2021/009422 A1 | 1/2021 |
| WO | WO-2021/011927 A1 | 1/2021 |
| WO | WO-2021/019167 A1 | 2/2021 |
| WO | WO-2021/026172 A1 | 2/2021 |
| WO | WO-2021/030672 A1 | 2/2021 |
| WO | WO-2021/041759 A1 | 3/2021 |

(56) References Cited

FOREIGN PATENT DOCUMENTS

| | | |
|---|---|---|
| WO | WO-2021/058657 A1 | 4/2021 |
| WO | WO-2021/059058 A1 | 4/2021 |
| WO | WO-2021/064219 A1 | 4/2021 |
| WO | WO-2021/080847 A1 | 4/2021 |
| WO | WO-2021/081206 A1 | 4/2021 |
| WO | WO-2021/084538 A1 | 5/2021 |
| WO | WO-2021/097230 A1 | 5/2021 |
| WO | WO-2021/099465 A1 | 5/2021 |
| WO | WO-2021/108809 A1 | 6/2021 |
| WO | WO-2021/112662 A1 | 6/2021 |
| WO | WO-2021/123074 A1 | 6/2021 |
| WO | WO-2021/130390 A1 | 7/2021 |
| WO | WO-2021/133943 A1 | 7/2021 |
| WO | WO-2021/137655 A1 | 7/2021 |
| WO | WO-2021/138676 A1 | 7/2021 |
| WO | WO-2021/142671 A1 | 7/2021 |
| WO | WO-2021/145796 A2 | 7/2021 |
| WO | WO-2021/148488 A2 | 7/2021 |
| WO | WO-2021/151974 A1 | 8/2021 |
| WO | WO-2021/163239 A1 | 8/2021 |
| WO | WO-2021/168083 A1 | 8/2021 |
| WO | WO-2021/177050 A1 | 9/2021 |
| WO | WO-2021/195589 A1 | 9/2021 |
| WO | WO-2022/003359 A1 | 1/2022 |

OTHER PUBLICATIONS

Alberts et al., Molecular Biology of the Cell, Fourth Edition, Newton Press. pp. 69-70, 107-108, 186-187, 616-619, Dec. 20, 2004.

Ashton et al., The challenge of applying Raman spectroscopy to monitor recombinant antibody production. Analyst. Nov. 21, 2013;138(22):6977-85.

Baradez et al., Application of Raman Spectroscopy and Univariate Modelling as a Process Analytical Technology for Cell Therapy Bioprocessing. Front Med (Lausanne). Mar. 5, 2018;5:47, 14 pages.

Berry et al., Quick generation of Raman spectroscopy based in-process glucose control to influence biopharmaceutical protein product quality during mammalian cell culture. Biotechnol Prog. Jan.-Feb. 2016;32(1):224-34.

Betty et al., Frequency Response Plots for Savitzky—Golay Filter Functions. Anal Chem. Feb. 1977;49(2):351-352.

Buckley et al., Applications of Raman Spectroscopy in Biopharmaceutical Manufacturing: A Short Review. Appl Spectrosc. Jun. 2017;71(6):1085-1116.

Carey, Biochemical Applications of Raman and Resonance Raman Spectroscopies. FEBS Letters. Jun. 1983;156(1):191.

Culka et al., Acquisition of Raman spectra of amino acids using portable instruments: outdoor measurements and comparison. Spectrochim Acta A Mol Biomol Spectrosc. Dec. 2010;77(5):978-83.

Encyclopedia of Cell Biology. Asakura Shoten. pp. 366-367, (2005).

Haberger et al., Assessment of chemical modifications of sites in the CDRs of recombinant antibodies: Susceptibility vs. functionality of critical quality attributes. MAbs. Mar.-Apr. 2014;6(2):327-39.

Harada et al., Origin of the doublet at 1360 and 1340 cm in the Raman spectra of tryptophand and related compounds. Spectrochimica Acta. 1986;42A(2/3):307-312.

Hodge, Dehydrated Foods. Chemistry of Browning Reactions in Model Systems. Agricultural and Food Chemistry. Oct. 14, 1953;1(15):928-943.

Lewis et al., Combined dynamic light scattering and Raman spectroscopy approach for characterizing the aggregation of therapeutic proteins. Molecules. Dec. 12, 2014;19(12):20888-905.

Li et al., Cysteine Conformatoin and Sulfhydryl Interactions in Proteins and Viruses. 1. Correlation of the Raman S-H Band with Hydrogen Bonding and Intramolecular Geometry in Model Compounds. J Am Chem Soc. 1991;113:456-462.

Li et al., Cysteine Conformatoin and Sulfhydryl Interactions in Proteins and Viruses. 2. Normal Coordinate Analysis of the Cysteine Side Chain in Moidel Compounds. J Am Chem Soc. 1992;114:7463-7469.

Li et al., Rapid characterization and quality control of complex cell culture media solutions using raman spectroscopy and chemometrics. Biotechnol Bioeng. Oct. 1, 2010;107(2):290-301.

Milligan et al., Semisynthetic model calibration for monitoring glucose in mammalian cell culture with in situ near infrared spectroscopy. Biotechnol Bioeng. May 2014;111(5):896-903.

Miura et al., Trytophan Raman Bands Sensitive to Hydrogen Bonding and Side-Chain Conformation. Journal of Raman Spectroscopy. 1989;20:667-671.

Mungikar et al., Use of In-Line Raman Spectroscopy as a Nondestructive and Rapid Analytical Technique to Monitor Aggregation of a Therapeutic Protein. American Pharmaceutical Review. https://www.americanpharmiceuticalreview.com. 8 pages, Nov. 1, 2010.

Pitters et al., Raman Spectroscopy as a Real-Time In Situ Analyzer for Cell Culture Bioprocesses. J Bioanal Biomed. 2016;8(3 suppl.):51.

Schwartz et al., Diafiltration: A Fast, Efficient Method for Desalting, or Buffer Exchange of Biological Samples. PALL, Life Sciences. www.pall.com, Scientific & Technical Report, PN 33289. 6 pages, (2003).

Stoner et al., Protein-solute interactions affect the outcome of ultrafiltration/diafiltration operations. J Pharm Sci. Sep. 2004;93(9):2332-42.

Sugeta et al., Vibrational Spectra and Molecular Conformations of Dialkyl Disulfides. Bulletin of the Chemical Society of Japan. Nov. 1973;46:3407-3411.

Sugeta, Normal vibrations and molecular conformations of dialkyl disulfides. Spectrochimica Acta. 1975;31A:1729-1737.

Van Wart et al., Agreement with the disulfide stretching frequency-conformation correlation of Sugeta, Go, and Miyazawa. Proc Natl Acad Sci U S A. May 1986;83(10):3064-7.

Van Wart et al., Disulfide bond dihedral angles from Raman spectroscopy. Proc Natl Acad Sci U S A. Sep. 1973;70(9):2619-23.

Wen et al., Application of Raman Spectroscopy in Biopharmaceutical Manufacturing. American Pharmaceutical Review. https://www.americanpharmaceuticalreview.com. 10 pages, May 1, 2010.

Wen et al., Ultraviolet-resonance raman spectroscopy of the filamentous virus Pf3: interactions of Trp 38 specific to the assembled virion subunit. Biochemistry. Jan. 11, 2000;39(1):146-52.

Wen, Raman spectroscopy of protein pharmaceuticals. J Pharm Sci. Nov. 2007;96(11):2861-78.

Whelan et al., In situ Raman spectroscopy for simultaneous monitoring of multiple process parameters in mammalian cell culture bioreactors. Biotechnol Prog. Sep.-Oct. 2012;28(5):1355-62.

Yamamoto et al., Development of Raman Optical Activity Spctrometer and Structural Analysis of Proteins in Solution. Bunseki Kagaku. 2013;62(5):409-422.

Yang et al., Effects of ammonia on CHO cell growth, erythropoietin production, and glycosylation. Biotechnol Bioeng. May 20, 2000;68(4):370-80.

Yuk et al., Controlling glycation of recombinant antibody in fed-batch cell cultures. Biotechnol Bioeng. Nov. 2011;108(11):2600-10.

International Preliminary Report on Patentability for Application No. PCT/US2018/055837, dated Apr. 30, 2020, 7 pages.

International Search Report and Written Opinion for Application No. PCT/US2018/055837, dated Jan. 8, 2019, 9 pages.

International Search Report and Written Opinion for Application No. PCT/US2019/048100, dated Nov. 20, 2019, 11 pages.

Japanese Office Action for Application No. 2020-083562, dated Dec. 1, 2022, 10 pages.

Singapore Office Action for Application No. 11202001127T, dated Dec. 4, 2020, 11 pages.

U.S. Appl. No. 16/160,194, filed Oct. 15, 2018, 2019-0112569, Published.

U.S. Appl. No. 16/550,989, filed Aug. 26, 2019, U.S. Pat. No. 11,358,984, Issued.

\* cited by examiner

USE OF RAMAN SPECTROSCOPY IN DOWNSTREAM PURIFICATION

CROSS-REFERENCE TO RELATED APPLICATIONS

This application is a continuation application of U.S. patent application Ser. No. 16/550,989, filed on Aug. 26, 2019, which claims benefit of and priority to U.S. Provisional Patent Application No. 62/723,188 filed on Aug. 27, 2018, and where permissible are incorporated by reference in their entirety.

TECHNICAL FIELD OF THE INVENTION

The invention is generally directed to systems and methods for monitoring and controlling one or more critical quality attributes (CQAs) or parameters in downstream protein purification processes.

BACKGROUND OF THE INVENTION

The number of monoclonal antibodies (mAbs) that have been approved for therapeutic use has increased significantly over the past decade. This is due in part to improvements in large scale manufacturing processes which facilitate the production of large quantities of mAbs. In addition, initiatives such as The Process Analytical Technology (PAT) framework of the Food and Drug Administration (FDA) have led to innovative solutions to process development, process analysis, and process control to better understand processes and control the quality of products. Efficient recovery and purification of mAbs from cell culture media is a critical part of the production process. The purification process should reliably produce mAbs that are safe for use in humans. This includes monitoring critical quality attributes (CQAs) that include protein attributes and impurities such as host cell proteins, DNA, viruses, endotoxins, aggregates, concentrations, excipients, and other species that have the potential to impact patient safety, efficacy, or potency. Protein concentration is also often a CQA in purified material, and appropriate protein concentration in process intermediates can be a critical process parameter for unit operation performance. These CQAs need to be monitored throughout production as well as throughout the program lifecycle.

To ensure that the final formulations of mAbs do not contain impurities above determined levels, the mAb products are tested at various stages of the downstream processing. Quality control in the manufacturing of bioproducts such as mAbs is generally accomplished by analyzing purification intermediates and formulated drug substance samples with offline methods for each lot production. The samples are removed from the processing equipment, for example a UF/DF skid, and subjected to offline tests to measure product CQAs such as protein concentration (g/L), buffer excipients, and size variants. Real time monitoring and analysis during manufacturing is not available resulting in increases in processing time and a higher risk of batch failure due to not meeting CQAs. Accordingly, there is a need for rapid, in-line methods of real-time quality control monitoring of mAbs.

Therefore, it is an object of the invention to provide systems and methods for real-time monitoring of critical quality attributes during the downstream purification process.

SUMMARY OF THE INVENTION

In situ Raman spectroscopy methods and systems for characterizing or quantifying a protein purification intermediate during production or manufacture are provided. In one embodiment, in situ Raman spectroscopy is used to characterize or quantify critical quality attributes of a protein drug during downstream processing (i.e., after harvest of the protein purification intermediate from cell culture fluid). For example, the disclosed in situ Raman spectroscopy methods and systems can be used to characterize and quantify protein purification intermediate critical quality attributes as the protein purification intermediates are purified, prior to formulation into the final drug product to be sold or administered. Critical quality attributes include but are not limited to protein concentration, excipients, high molecular weight (HMW) species, antibody titer, and drug-antibody ratio.

One embodiment provides a method of producing a concentrated protein purification intermediate by determining concentrations of a protein purification intermediate in-real time using in situ Raman spectroscopy while concentrating/diafiltering the protein purification intermediate and adjusting parameters of the concentrating step in-real time to obtain the pre-determined concentration targets and excipient levels necessary for formulation of drug substance. The protein purification intermediate product can have a concentration of 5 mg/mL to 300 mg/mL, preferably 50 mg/mL to 300 mg/mL for subsequent formulation steps. In one embodiment, the protein purification intermediate is concentrated to a desired concentration target using ultrafiltration during primary or final concentration. Diafiltration is used during processing following primary concentration as a means for buffer exchange to achieve the desired final formulation components. The protein purification intermediate can be harvested from a bioreactor, a fed-batch culture, or a continuous culture. In another embodiment, determining the concentration of the protein purification intermediate can occur continuously or intermittently in real-time. Quantifying of protein concentration can be performed in intervals from approximately 5 seconds to 10 minutes, hourly, or daily. The protein purification intermediate can be an antibody or antigen binding fragment thereof, a fusion protein, or a recombinant protein. Spectral data can be collected at one or more wavenumber ranges selected from the group consisting of 977-1027 $cm^{-1}$, 1408-1485 $cm^{-1}$, 1621-1711 $cm^{-1}$, 2823-3046 $cm^{-1}$, and combinations thereof.

Another embodiment provides a method of producing a protein purification intermediate by independently performing Raman Spectroscopy analysis on a plurality of protein purification intermediates to produce a universal model capable of quantifying any one of the plurality of protein purification intermediates. The concentration of a protein purification intermediate can be determined using in situ Raman spectroscopy with the universal model during concentration of the protein purification intermediate from beginning to end of concentrating the protein purification intermediate. Another embodiment provides a method of producing a protein purification intermediate to produce a protein specific model capable of quantifying protein concentrations that would be used for commercial enabling productions of the protein.

The model can be produced using Partial Least Squares Regression Analysis of raw spectral data and using an orthogonal method for offline protein concentration data. Pre-processing techniques such as Standard Normal Variant (SNV) and/or point-smoothing technique can be $1^{st}$ derivative with 21 $cm^{-1}$ smoothing can be performed on the Raman spectroscopy data to dampen model variability and prediction error. Further model refinement can be performed to isolate spectral regions that correlate to CQA predictions such as protein concentration. In one embodiment, the model has ≤5% error margin, preferably ≤3% error margin.

Still another embodiment provides a method for monitoring and controlling the levels of excipients in harvested cell culture fluid and/or protein purification intermediate during downstream purification by determining concentrations of the excipients in-real time using in situ Raman spectroscopy while purifying the cell culture fluid or protein purification intermediate, and adjusting parameters of the purification step in-real time to obtain or maintain predetermined amounts of the excipients in the harvested cell culture fluid and/or protein purification intermediate. The excipient can be acetate, citrate, histidine, succinate, phosphate, hydroxymethylaminomethane (Tris), proline, arginine, sucrose, or combinations thereof. The excipient can be a surface excipient such as polysorbate 80, polysorbate 20, and poloxamer 188.

BRIEF DESCRIPTION OF THE DRAWINGS

FIG. 8A shows the Raman model error for real-time predictions in various stages of UF/DF processing (primary concentration, diafiltration, and final concentrated pool). FIG. 8B shows the Raman model error for the final DoE model at various stages of UF/DF processing (primary concentration, diafiltration, and final concentrated pool).

DETAILED DESCRIPTION OF THE INVENTION

I. Definitions

Figure 1:
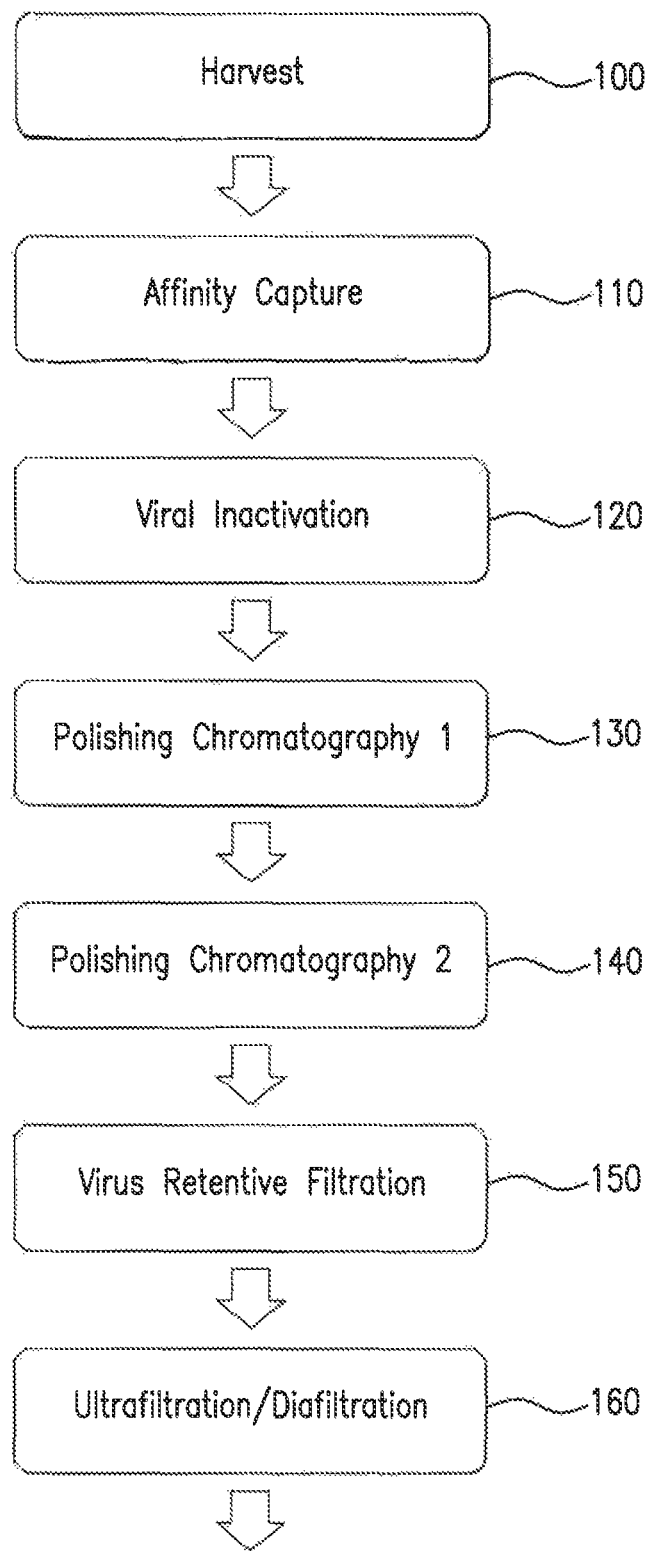
FIG. 1 is a flow chart showing an exemplary protein purification process.

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. ±10%; in other embodiments the values may range in value either above or below the stated value in a range of approx. ±5%; in other embodiments the values may range in value either above or below the stated value in a range of approx. ±2%; in other embodiments the values may range in value either above or below the stated value in a range of approx. ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "protein" refers to a molecule comprising two or more amino acid residues joined to each other by a peptide bond. Protein includes polypeptides and peptides and may also include modifications such as glycosylation, lipid attachment, sulfation, gamma-carboxylation of glutamic acid residues, alkylation, hydroxylation and ADP-ribosylation.

Proteins can be of scientific or commercial interest, including protein-based drugs, and proteins include, among other things, enzymes, ligands, receptors, antibodies and chimeric or fusion proteins. Proteins are produced by various types of recombinant cells using well-known cell culture methods, and are generally introduced into the cell by transfection of genetically engineering nucleotide vectors (e.g., such as a sequence encoding a chimeric protein, or a codon-optimized sequence, an intronless sequence, etc.), where the vectors may reside as an episome or be integrated into the genome of the cell.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in US Patent Application Publication No. 2010/0331527, which is incorporated by reference into this application.

"Secondary structure" refers to local folded structures that form within a polypeptide due to interactions between atoms of the backbone. The most common types of secondary structures are a helix and the β pleated sheet. Both structures are held in shape by hydrogen bonds, which form between the carbonyl O of one amino acid and the amino H of another.

As used herein, "excipient" refers to a pharmacologically inactive substance that is used as a stabilizing agent for long-term storage of the formulated drug substance. Generally, additional excipients are added to the final concentrated pool to produce formulated drug substance. However, during UF/DF processing excipient levels are monitored to ensure the levels will not impact the desired formulation strategy. Excipients provide bulk to the pharmaceutical formulation, facilitate drug absorption or solubility, and provide stability and prevent denaturation. Common pharmaceutical excipients include but are not limited to amino acids, fillers, binders, disintegrants, coatings, sorbents, buffering agents, chelating agents, lubricants, glidants, preservatives, antioxidants, flavoring agents, sweeteners, coloring agents, solvent and co-solvents, and viscosity imparting agents. In one embodiment, the excipient is polyethylene glycol including but not limited to PEG-3550.

"Polyethylene glycol" or "PEG" is a polyether polymer of ethylene oxide commonly used in food, medicine and cosmetics. It is a non-ionic macromolecule that is useful as a molecule that reduces the solubility of a biomolecule. PEG is commercially available in different molecular weights ranging from 300 g/mol to 10,000,000 g/mol. Exemplary types of PEG include but are not limited to PEG 20000, PEG 8000 and PEG 3350. PEG is available in different geometries, including linear, branched (3-10 chains attached to central core), star-shaped (10-100 chains attached to a central core), and combshaped (multiple chains attached to a polymer backbone).

"Raman spectroscopy" is a spectroscopic technique used to measure the wavelength and intensity of in-elastically scattered light from molecules. It is based on the principle that monochromatic incident radiation on materials will be reflected, absorbed, or scattered in a specific manner, which is dependent upon the particular molecule or protein which receives the radiation. The majority of the energy is scattered at the same wavelength, called elastic or Rayleigh scattering. A small amount (<0.001%) is scattered at different wavelengths, called inelastic or Raman scattering. Raman scatter is associated with rotational, vibrational, and electronic level transitions. Raman spectroscopy can reveal the chemical and structural composition of samples.

As used herein, "ultrafiltration" refers to a membrane process that is widely used for protein concentration in the downstream processing of protein therapeutics during the purification of recombinant proteins Ultrafiltration is a size-based separation, where species larger than the membrane pores are retained and smaller species pass through freely. During processing, the protein solution is pumped tangentially across the surface of a semi-permeable parallel flat sheet membrane. The membrane is permeable to buffer and buffer salts but generally impermeable to monoclonal antibodies. The driving force for permeation is applied transmembrane pressure (TMP) induced by flow restriction at the outlet of the membrane flow channel (TMP=$P_{feed}$+$P_{retentate}$)/2-$P_{permeate}$.).

As used herein, "primary concentration" refers to the initial step where transmembrane pressure drives water and salts across the permeable membrane, which reduces the liquid volume and thus increases protein concentration. The extent of concentration in primary concentration may be optimized to balance throughput, protein stability, processing time and buffer consumption.

As used herein, "diafiltration" refers to a technique that uses a semi-permeable membrane to exchange a product of interest from one liquid medium into another. Buffer exchange and de-salting are typically performed using a diafiltration mode in which the small impurities and buffer components are effectively washed away from the product by the continuous addition of a buffer that is intended to condition the protein to a stable pH and excipient concentration that allows high product concentration. This can be performed in a continuous or discontinuous mode based on processing techniques.

Diafiltration is often combined with ultrafiltration to achieve the desired volume reduction while also removing impurities and salts. UF/DF is the final unit operation in downstream purification which conditions the mAb to achieve pH, excipient content, and protein concentration conducive to long term storage and addition of stabilizing excipients to generate Formulated Drug Substance (FDS).

As used herein, "final concentration" refers to the final step where transmembrane pressure drives water and salts across the permeable membrane, which reduces the liquid volume and thus increases protein concentration to the desired target for storage and/or formulation. The resultant pool from the final concentration step is final concentrated pool (FCP). This final concentration step can be performed in a continuous or discontinuous processing mode.

The terms "bioproduct" and "protein purification intermediate" can be used interchangeably and refer to any antibody, antibody fragment, modified antibody, protein, glycoprotein, or fusion protein as well as final drug substances purified from a bioreactor process.

The terms "control" and "controlling" refer to adjusting an amount or concentration level of a critical quality attribute in a harvested cell culture fluid to a predefined set point.

As used herein, the term "upstream processing" refers to the first step in which antibodies or therapeutic proteins are produced, usually by bacterial or mammalian cell lines, in bioreactors. Upstream processing includes media preparation, cell culture, and cell separation and harvest. When the cells have reached the desired density, they are harvested and moved to the downstream section of the bioprocess. The term "downstream processing" refers to the isolation and purification that occurs after the harvest of an antibody or therapeutic protein from a bioreactor. Typically, this means recovery of a product from an aqueous solution via several different modalities. The harvested product is processed to meet purity and critical quality attribute requirements during downstream processing.

As used herein, the term "protein purification intermediate" refers to a protein that has been harvested from a bioreactor and refers to any intermediate during downstream processing.

The term "concentrated protein purification intermediate" refers to a protein purification intermediate with a concentration greater than 5 mg/mL. More preferably the concentration is between 50 mg/mL to 300 mg/mL.

The terms "monitor" and "monitoring" refer to regularly checking an amount or concentration level of a critical quality attribute in a cell culture or a harvested cell culture fluid.

The term "harvested cell culture fluid" refers to fluid that is removed from a bioreactor containing cells that were engineered to secrete proteins of interest. The "harvested cell culture fluid" optimally contains the secreted protein of interest, for example a monoclonal antibody.

As used herein "critical quality attribute (CQA)" refers to a physical, chemical, biological, or microbiological property or characteristic that should be within an appropriate limit, range, or distribution to ensure the desired product quality of a biologic therapeutic drug product. These attributes have the potential to impact safety, efficacy, and/or potency. Critical quality attributes include but are not limited to protein concentration, high molecular weight species, buffer excipients, and pH.

As used herein, "formulated drug substance" refers to an active ingredient that is intended to furnish pharmacological activity, but does not include intermediates used in the synthesis of such ingredient.

As used herein, "universal model" refers to a mathematical correlation of spectral properties of different recombinant proteins used to predict a critical quality attribute.

As used herein, "mAb specific model" refers to a mathematical correlation of spectral properties of one particular protein used to predict a critical quality attribute.

As used herein "titer" refers to the amount of an antibody or protein molecules in a solution.

II. Systems and Methods for Characterization of Downstream Protein Purification Products Systems and methods for monitoring and controlling protein concentration during protein manufacturing are provided. Concentrated protein solutions are difficult to measure accurately due to high correlated solution viscosities (>10 cP). Accurate quantification requires specialty offline equipment and typically solution dilution. In high concentration UF/DF, final excipient levels are a function of protein concentration due to the Gibbs-Donnan effect. Real time monitoring and analysis during manufacturing is not available which increases processing time and potential batch failure due to not meeting CQAs. The systems and methods disclosed herein can be used for in-line monitoring of protein concentration and other critical quality attributes.

In one embodiment, the Raman spectroscopy system is an in-line or in situ Raman spectroscopy system used during production of a final concentrated pool, which could be highly concentrated (≥150 g/L). Typically, the Raman spectroscopy system is employed downstream of production of the protein purification intermediate, for example during processing of the protein purification intermediate after harvest from a bioreactor or fed-batch culture system and subsequent purification. FIG. 1 shows an exemplary protein purification process. Typically, the protein purification intermediate is harvested from cell culture (100) and processed through various purification steps such as affinity capture (110), viral inactivation (120), polishing chromatography (130 and 140), virus retentive filtration (150), and ultrafiltration/diafiltration (160), to produce the final concentrated pool which is then formulated to drug substance. In one embodiment, the monitoring of protein concentration in a harvested cell culture fluid is performed by in situ Raman spectroscopy.

A. Raman Spectroscopy

In one embodiment, monitoring and controlling protein concentration in a harvested cell culture fluid is performed by Raman spectroscopy. Raman spectroscopy is a form of vibrational spectroscopy that provides information about molecular vibrations that can be used for sample identification and critical quality attribute quantitation. In situ Raman analysis is a method of analyzing a sample in its original location without having to extract a portion of the sample for analysis in a Raman spectrometer. In situ Raman analysis is advantageous in that the Raman spectroscopy analyzers are noninvasive and nondestructive which reduces the risk of contamination and loss of protein quality. In-line Raman analysis can be implemented to enable continuous processing while monitoring protein concentration of harvested cell culture fluid, protein purification intermediates, and/or final concentrated pool.

The in situ Raman analysis can provide real-time assessments of protein concentration in protein purification intermediates. For example, the raw spectral data provided by in situ Raman spectroscopy can be used to obtain and monitor the current protein concentration in protein purification intermediates. In this aspect, to ensure that the raw spectral data is continuously up to date, the spectral data from the Raman spectroscopy should be acquired about every 5 seconds to 10 hours. In another embodiment, the spectral data should be acquired about every 15 minutes to 1 hour. In still another embodiment, the spectral data should be acquired about every 20 minutes to 30 minutes.

The monitoring of the protein concentration in the protein purification intermediate can be analyzed by any commercially available Raman spectroscopy analyzer that allows for in situ Raman analysis. The in situ Raman analyzer should be capable of obtaining raw spectral data within the protein purification intermediate. For example, the Raman analyzer should be equipped with a probe that may be inserted inline of the fluid circuit. Suitable Raman analyzers include, but are not limited to, RamanRXN2 and RamanRXN4 analyzers (Kaiser Optical Systems, Inc. Ann Arbor, MI).

The raw spectral data obtained by in situ Raman spectroscopy may be compared to offline protein concentration measurements in order to correlate the peaks within the spectral data to the protein concentration. Offline protein concentration measurements may be used to determine which spectral regions exhibit the protein signal. The offline measurement data may be collected through any appropriate analytical method. In the case of protein concentration, for example, the offline measurement can be collected using SoloVPE (C-technologies). Additionally, any type of multivariate software package, for example, SIMCA 13 (MKS Data Analytic Solutions, Umea, Sweden), may be used to correlate the peaks within the raw spectral data to offline measurements of protein concentration. However, in some embodiments, it may be necessary to pretreat the raw spectral data with spectral filters to remove any varying baselines. For example, the raw spectral data may be pretreated with any type of point smoothing technique or normalization technique. Normalization may be needed to correct for any probe, optic, laser power variation and exposure time by the Raman analyzer. In one embodiment, the raw spectral data may be treated with point smoothing, such as 1st derivative with 21 $cm^{-1}$ point smoothing, and normalization, such as Standard Normal Variate (SNV) normalization. These pre-processing techniques may be combined for certain spectral regions to improve the model predictions.

Chemometric modeling may also be performed on the obtained spectral data. In this aspect, one or more multivariate methods including, but not limited to, Partial Least Squares (PLS), Principal Component Analysis (PCA), Orthogonal Partial least squares (OPLS), Multivariate Regression, Canonical Correlation, Factor Analysis, Cluster Analysis, Graphical Procedures, and the like, can be used on the spectral data. In one embodiment, the obtained spectral data is used to create a PLS regression model. A PLS regression model may be created by projecting predicted variables and observed variables to a new space. In this aspect, a PLS regression model may be created using the measurement values obtained from the Raman analysis and the offline measurement values. The PLS regression model provides predicted process values, for example, predicted protein concentration value. In one embodiment, the model provides predicted protein concentration values with ≤5% error compared to off-line protein concentration values. In a preferred embodiment, the model provides predicted protein concentration values with ≤3% error compared to off-line protein concentration values.

After chemometric modeling, a signal processing technique may be applied to the predicted protein concentration values. In one embodiment, the signal processing technique will dampen model variability and prediction error. In this aspect, one or more of the pre-processing techniques may be applied to the predicted protein concentration values. Any pre-processing techniques known to those skilled in the art may be utilized. For example, the noise reduction technique may include data smoothing and/or signal rejection. Smoothing is achieved through a series of smoothing algorithms and filters while signal rejection uses signal characteristics to identify data that should not be included in the analyzed spectral data. In one embodiment, the predicted protein concentration values are noise mitigated by a noise reduction filter. The noise reduction filter provides final predicted protein concentration values. In this aspect, the noise reduction technique combines raw measurements with a model-based estimate for what the measurement should yield according to the model. In one embodiment, the noise reduction technique combines a current predicted protein concentration value with its uncertainties. Uncertainties can be determined by the repeatability of the predicted protein concentration values and the current protein concentration values. Once the next predicted protein concentration value is observed, the estimate of the predicted protein concentration value is updated using a weighted average where more weight is given to the estimates with higher certainty. Using an iterative approach, the final protein concentration values may be updated based on the previous measurement and the current measurement. In this aspect, the algorithm should be recursive and able to run in real time so as to utilize the current predicted protein concentration value, the previous value, and experimentally determined constants. The noise reduction technique improves the robustness of the measurements received from the Raman analysis and the PLS predictions by reducing noise upon which the automated feedback controller will act.

B. Methods of Use

The disclosed methods can be used to monitor and control protein concentration in harvested cell culture and/or protein purification intermediates fluids during downstream protein purification processes. Common downstream purification processes include but are not limited to centrifugation, direct depth filtration, protein A affinity purification, viral inactivation steps, ion-exchange chromatography, hydrophobic interaction chromatography, size-exclusion chromatography, ultrafiltration/diafiltration, viral retentive filtration, and combinations thereof. These unit operations are used in a defined sequential combination to isolate the protein of interest and ensure impurities and/or critical quality attributes are monitored prior to the production of formulated drug substance. In one embodiment, the disclosed methods include a Raman probe in-line of the fluid circuit. In another embodiment, the disclosed methods can be used to produce a concentrated protein purification intermediate or final concentrated pool.

1. Antibody Titer and Protein Concentration

Both antibody titer and protein concentration are important factors in the purification of bioproducts. Antibody titer measured after the initial harvest of the cell culture fluid is important to determine column loadings and ensure a robust purification process for removal of impurities. Monitoring protein concentration throughout purification steps is important to ensure both the proper concentration of end product, and proper performance of the purification unit operations performed. Improper protein concentration can lead to ineffective drug products or production of formulated drug substance.

In one embodiment, harvested cell culture fluid is subjected to Raman spectral analysis immediately after being harvested, but before any additional purification has begun. Raman spectral data can be used after harvest to quantify antibody titer in the harvested cell culture fluid. Protein concentration can be measured using the disclosed methods at multiple steps during the protein purification process, for example, during affinity capture, during polishing chromatography, during virus retentive filtration, or during ultrafiltration/diafiltration. Inline Raman probes can detect Raman scattering in the harvested cell culture fluid and/or protein purification intermediate within the fluid circuit without removing sample from the system providing analytical characterizations that are normally determined in an offline fashion.

In one embodiment, if the protein concentration is not within the pre-determined concentration during ultrafiltration/diafiltration, the system is notified and the protein purification intermediate is altered accordingly. For example, if the protein concentration in the protein purification intermediate is below the predetermined protein concentration the protein purification intermediate can be further concentrated by performing ultrafiltration/diafiltration.

In one embodiment, the concentration step is performed by Protein A affinity chromatography.

2. Drug-to-Antibody Ratio

In another embodiment, the disclosed methods can be used to monitor and control drug-to-antibody ratio (DAR). DAR is a quality attribute that is monitored during development of antibody-drug conjugates (ADC), antibody-radionuclide conjugates (ARC), and general protein conjugates (potent steroids, non-cytotoxic payloads, etc.) to ensure consistent product quality and to facilitate subsequent labeling with payloads. DAR is the average number of drugs or other therapeutic molecules conjugated to antibodies, and is an important quality attribute in the production of therapeutic conjugates. The DAR value affects the efficacy of the conjugated drug as low drug loading reduces the drug potency while high loading can negatively affect the pharmacokinetics and safety.

In one embodiment, antibody-radionuclide conjugates are subjected to Raman spectral analysis immediately after being conjugated, but before any additional purification occurs. Raman spectral data can be used after conjugation to determine the DAR.

In one embodiment, if the DAR is not within the predetermined concentration during processing, the system is notified and the ADC intermediate is altered accordingly. For example, if the DAR in the ADC intermediate is below the predetermined DAR the conjugation reaction components can be altered, for example reactant concentrations can be optimized, the type of linker can be altered, temperature, or other manufacturing variables can be optimized.

3. Buffer Excipients

The disclosed methods can be used to monitor and control the levels of buffer excipients in harvested cell culture fluid and/or protein purification intermediate during downstream purification. Buffer excipients that are commonly used in monoclonal antibody productions include but are not limited to acetate, citrate, histidine, succinate, phosphate, and hydroxymethylaminomethane (Tris), proline, and arginine. Surfactant excipients include but are not limited to polysorbate 80 (Tween 80), polysorbate 20 (Tween 20), and poloxamer 188. Polyol/disaccharide/polysaccharide excipients include but are not limited to mannitol, sorbitol, sucrose, and dextran 40. Antioxidant excipients include but are not limited to ascorbic acid, methionine, and ethylenediaminetetraacetic acid (EDTA). Two commonly used amino acid excipients are histidine and arginine. In a preferred embodiment, the excipient that is monitored and controlled is histidine and arginine.

Final concentrated pool excipient concentrations differ from the composition of the diafiltration buffer due to the combination of the excluded volume and Donnan effects. The Donnan effect is a phenomenon that arises due to retention of the net positively charged protein by the membrane during UF/DF combined with the requirement for charge neutrality in both the retentate and permeates. To balance the positively charged protein, negatively charged buffer components are enriched in the retentate relative to the diafiltration buffer, while positively charged buffer components are expelled. This effect can lead to FCP pH and buffer excipient concentrations differing substantially from the diafiltration buffer composition (Stoner, et al., *J Pharm Sci*, 93:2332-2342 (2004)).

Volume exclusion describes the behavior of highly concentrated samples in which protein occupies a significant fraction of the solution volume. Buffer is excluded from the volume occupied by the protein, causing the buffer solute concentrations to decrease as protein concentration increases expressed as moles (or mass) of solute per solution volume. Buffer is excluded from the volume occupied by the protein, causing the buffer solute concentrations to decrease as protein concentration increases when expressed as moles (or mass) of solute per solution volume.

Based on both of these principles and buffer excipient levels being critical quality attributes, inline Raman probes will minimize offline analytical characterization and provide further process understanding to ensure excipient levels are sufficient prior to formulation.

4. High Molecular Weight Impurities

In production of monoclonal antibodies, low levels of products-related impurities often exist even after extensive purification steps. High molecular weight (HMW) species (e.g., antibody dimer species) are a product-related impurity that contributes to size heterogeneity of mAb products. The formation of HMW species within a therapeutic mAb drug product as a result of protein aggregation can potentially compromise both drug efficacy and safety. HMW species are considered a CQA that are routinely monitored during drug development and as part of release testing of purified protein drug products during manufacturing.

In one embodiment, the disclosed methods can be used to identify protein drug products that contain HMW species. HMW species can be detected by Raman spectroscopy at various steps during the purification process including but not limited to during affinity capture, during viral inactivation, during polishing chromatography, during virus retentive filtration, during ultrafiltration/diafiltration, or combinations thereof.

In one embodiment, the disclosed methods detect HMW species in the harvested cell culture fluid and the fluid is further processed to remove the HMW species. Methods of removing HMW species for cell culture fluid include additional polishing steps including but not limited to cation exchange chromatography and anion exchange chromatography.

C. UF/DF Systems

Figure 6:
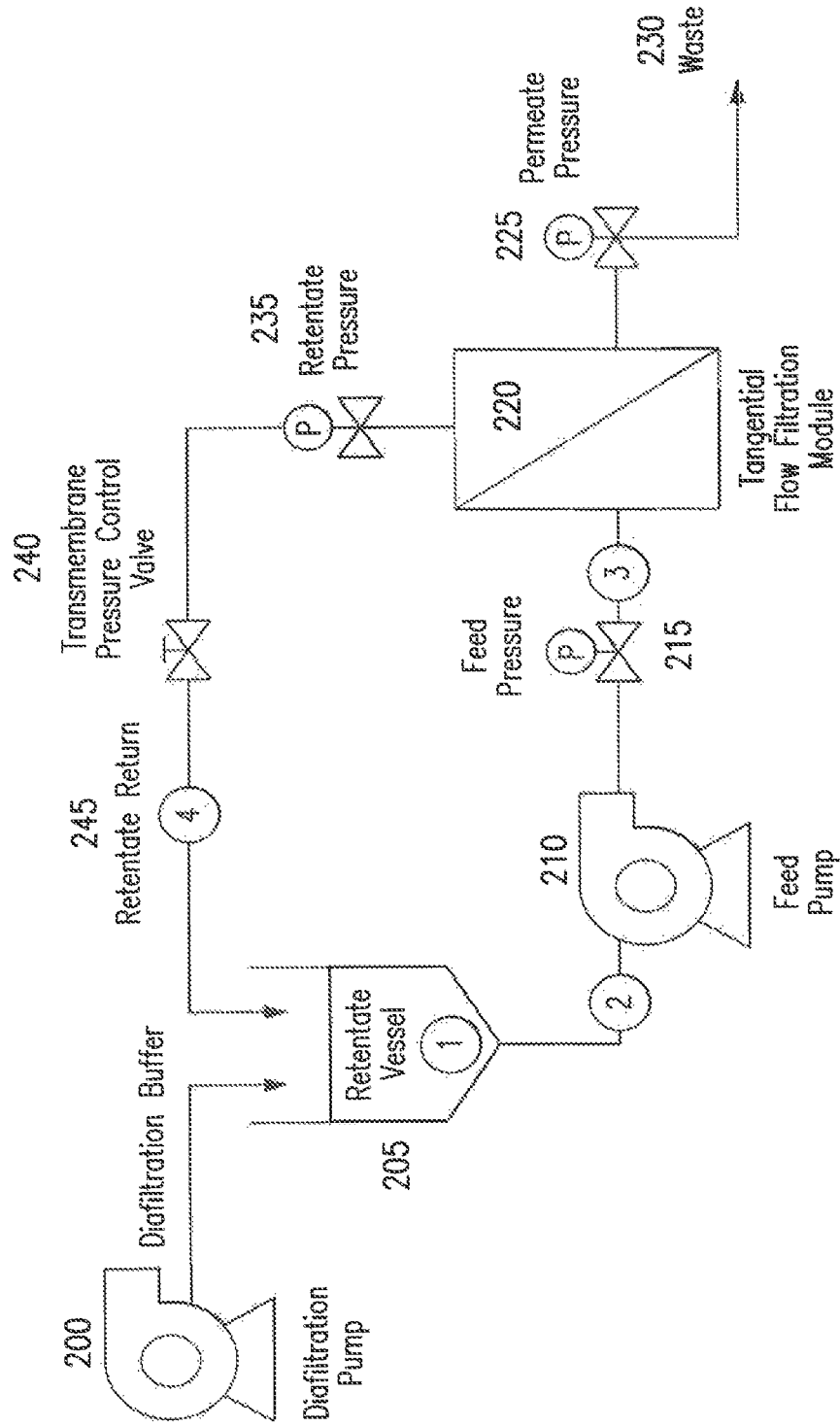
FIG. 6 is a schematic illustration of an ultrafiltration/diafiltration system, including locations for inline Raman probe placement.

FIG. 6 illustrates an ultrafiltration/diafiltration processing system, including various locations for in-line Raman probes (circled numbers 1-4). Protein purification intermediate is pumped into a retentate vessel 205 by a diafiltration pump 200 which may be a peristaltic, rotary lobe, pressure transfer, or diaphragm pump. Fluid from retentate vessel 205 flows to feed pump 210 which may be either a rotary lobe, peristaltic or diaphragm pump, past feed pressure valve 215 and into tangential flow filtration module (TFFM) 220. In TFFM 220 the protein purification intermediate is subjected to ultrafiltration across a membrane. The bioproduct of interest is retained in the fluid (retentate) while water and low molecular weight solutes including buffer excipients pass through the membrane in the permeate (filtrate) which exits the system by passing through permeate pressure valve 225 into waste tank 230. The retentate exits TFFM 220 and passes through retentate pressure valve 235, transmembrane pressure control valve 240, and retentate return channel 245 wherein it flows back into retentate vessel 205. The process can be repeated as necessary to concentrate the bioproduct, remove impurities, and ensure CQAs are within acceptable limits. During diafiltration the same flow path described above is followed where permeable solutes are replaced as new buffer is washed into the product stream. When new buffer is added at the same rate as permeate is removed from the system, the sum of the retentate tank and skid hold-up volume defines the system volume. One turn-over volume (TOV) is defined as an amount of diafiltration buffer added to the UF/DF process equal to the system volume. Typically, replacement of 8-times system volume (8 TOV) assures >99.9% buffer exchange (Schwarts, L., Scientific and Technical Report, PN 33289).

Additionally, during the UF/DF process, it is necessary to mix the protein solution in the retentate vessel 205. Differences in density between the diafiltration buffer, the retentate return, and bulk retentate during diafiltration require that agitation in the tank should be sufficient to ensure adequate buffer exchange, yet sufficiently moderate to avoid sheer, as this has been observed to result in protein aggregation and subvisible particle (SVP) generation in certain products. Additionally, it is important to ensure adequate mixing of retentate return during concentration stages to prevent protein concentration polarization in the retentate tank resulting in higher protein concentrations being delivered to the UF/DF membranes.

In one embodiment the Raman probe is placed at location 1, downstream of diafiltration pump 200 in retentate vessel 205. The Raman probe could alternatively be placed at location 2 downstream of retentate vessel 205 inline before feed pump 210. In another embodiment, the Raman probe is placed inline at location 3 between feed pressure pump 215 and tangential flow filtration module 220. In yet another embodiment, the Raman probe is placed inline in retentate return 245. The location of the Raman probe is critical to ensure accurate inline measurements in a complicated system that has engineering and processing constraints.

D. Cell Culture

The harvested cell culture fluid can be harvested from a bioreactor containing cells engineered to produce monoclonal antibodies. The term "cell" includes any cell that is suitable for expressing a recombinant nucleic acid sequence. Cells include those of prokaryotes and eukaryotes, such as bacterial cells, mammalian cells, human cells, non-human animal cells, avian cells, insect cells, yeast cells, or cell fusions such as, for example, hybridomas or quadromas. In certain embodiments, the cell is a human, monkey, ape, hamster, rat or mouse cell. In other embodiments, the cell is selected from the following cells: Chinese Hamster Ovary (CHO) (e.g. CHO K1, DXB-11 CHO, Veggie-CHO), COS (e.g. COS-7), retinal cell, Vero, CV1, kidney (e.g. HEK293, 293 EBNA, MSR 293, MDCK, HaK, BHK21), HeLa, HepG2, WI38, MRC 5, Colo25, HB 8065, HL-60, lymphocyte, e.g. Jurkat (T lymphocyte) or Daudi (B lymphocyte), A431 (epidermal), U937, 3T3, L cell, C127 cell, SP2/0, NS-0, MMT cell, stem cell, tumor cell, and a cell line derived from an aforementioned cell. In some embodiments, the cell comprises one or more viral genes, e.g. a retinal cell that expresses a viral gene (e.g. a PER.C6® cell). In some embodiments, the cell is a CHO cell. In other embodiments, the cell is a CHO K1 cell.

In protein production, a "fed-batch cell culture" or "fed-batch culture" refers to a batch culture wherein the cells and culture medium are supplied to the culturing vessel initially, and additional culture nutrients are slowly fed, in discrete increments, to the culture during culturing, with or without periodic cell and/or product harvest before termination of culture. Fed-batch culture includes "semi-continuous fed-batch culture" wherein periodically whole culture (which may include cells and medium) is removed and replaced by fresh medium. Fed-batch culture is distinguished from simple "batch culture" whereas all components for cell culturing (including the animal cells and all culture nutrients) are supplied to the culturing vessel at the start of the culturing process in batch culture. Fed-batch culture may be different from "perfusion culture" insofar as the supernatant is not removed from the culturing vessel during a standard fed-batch process, whereas in perfusion culturing, the cells are restrained in the culture by, e.g., filtration, and the culture medium is continuously or intermittently introduced and removed from the culturing vessel. However, removal of samples for testing purposes during fed-batch cell culture is contemplated. The fed-batch process continues until it is determined that maximum working volume and/or protein production is reached, and protein is subsequently harvested.

The phrase "continuous cell culture" relates to a technique used to grow cells continually, usually in a particular growth phase. For example, if a constant supply of cells is required, or the production of a particular protein of interest is required, the cell culture may require maintenance in a particular phase of growth. Thus, the conditions must be continually monitored and adjusted accordingly in order to maintain the cells in that particular phase.

The terms "cell culture medium" and "culture medium" refer to a nutrient solution used for growing mammalian cells that typically provides the necessary nutrients to enhance growth of the cells, such as a carbohydrate energy source, essential (e.g. phenylalanine, valine, threonine, tryptophan, methionine, leucine, isoleucine, lysine, and histidine) and nonessential (e.g. alanine, asparagine, aspartic acid, cysteine, glutamic acid, glutamine, glycine, proline, serine, and tyrosine) amino acids, trace elements, energy sources, lipids, vitamins, etc. Cell culture medium may contain extracts, e.g. serum or peptones (hydrolysates), which supply raw materials that support cell growth. Media may contain yeast-derived or soy extracts, instead of animal-derived extracts. Chemically defined medium refers to a cell culture medium in which all of the chemical components are known (i.e. have a known chemical structure). Chemically defined medium is entirely free of animal-derived components, such as serum- or animal-derived peptones. In one embodiment, the medium is a chemically defined medium.

The solution may also contain components that enhance growth and/or survival above the minimal rate, including hormones and growth factors. The solution may be formulated to a pH and salt concentration optimal for survival and proliferation of the particular cell being cultured.

E. Proteins of Interest

Any protein of interest suitable for expression in prokaryotic or eukaryotic cells can be monitored using the disclosed methods. For example, the protein of interest includes, but is not limited to, an antibody or antigen-binding fragment thereof, a chimeric antibody or antigen-binding fragment thereof, an ScFv or fragment thereof, an Fc-fusion protein or fragment thereof, a growth factor or a fragment thereof, a cytokine or a fragment thereof, or an extracellular domain of a cell surface receptor or a fragment thereof. Proteins of interest may be simple polypeptides consisting of a single subunit, or complex multisubunit proteins comprising two or more subunits. The protein of interest may be a biopharmaceutical product, food additive or preservative, or any protein product subject to purification and quality standards.

In some embodiments, the antibody is selected from the group consisting of an anti-Programmed Cell Death 1 antibody (e.g., an anti-PD1 antibody as described in U.S. Pat. No. 9,987,500), an anti-Programmed Cell Death Ligand-1 (e.g., an anti-PD-L1 antibody as described in in U.S. Pat. No. 9,938,345), an anti-D114 antibody, an anti-Angiopoetin-2 antibody (e.g., an anti-ANG2 antibody as described in U.S. Pat. No. 9,402,898), an anti-Angiopoetin-Like 3 antibody (e.g., an anti-AngPtl3 antibody as described in U.S. Pat. No. 9,018,356), an anti-platelet derived growth factor receptor antibody (e.g., an anti-PDGFR antibody as described in U.S. Pat. No. 9,265,827), an anti-Erb3 antibody, an anti-Prolactin Receptor antibody (e.g., anti-PRLR antibody as described in U.S. Pat. No. 9,302,015), an anti-Complement 5 antibody (e.g., an anti-C5 antibody as described in U.S. Pat. No. 9,795,121), an anti-TNF antibody, an anti-epidermal growth factor receptor antibody (e.g., an anti-EGFR antibody as described in U.S. Pat. No. 9,132,192 or an anti-EGFRvIII antibody as described in U.S. Pat. No. 9,475,875), an anti-Proprotein Convertase Subtilisin Kexin-9 antibody (e.g., an anti-PCSK9 antibody as described in U.S. Pat. No. 8,062,640 or U.S. Pat. No. 9,540,449), an anti-Growth And Differentiation Factor-8 antibody (e.g. an anti-GDF8 antibody, also known as anti-myostatin antibody, as described in U.S. Pat. No. 8,871,209 or 9,260,515), an anti-Glucagon Receptor (e.g., anti-GCGR antibody as described in U.S. Pat. No. 9,587,029 or 9,657,099), an anti-VEGF antibody, an anti-IL1R antibody, an interleukin 4 receptor antibody (e.g., an anti-IL4R antibody as described in U.S. Pat. Appln. Pub. No. US2014/0271681A1 or U.S. Pat. No. 8,735,095 or 8,945,559), an anti-interleukin 6 receptor antibody (e.g., an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g., anti-IL33 antibody as described in U.S. Pat. No. 9,453,072 or 9,637,535), an anti-Respiratory syncytial virus antibody (e.g., anti-RSV antibody as described in U.S. Pat. Appln. Pub. No. 9,447,173), an anti-Cluster of differentiation 3 (e.g., an anti-CD3 antibody, as described in U.S. Pat. Nos. 9,447,173 and 9,447,173, and in U.S. Application No. 62/222,605), an anti-Cluster of differentiation 20 (e.g., an anti-CD20 antibody as described in U.S. Pat. No. 9,657,102 and US20150266966A1, and in U.S. Pat. No. 7,879,984), an anti-CD19 antibody, an anti-CD28 antibody, an anti-Cluster of Differentiation-48 (e.g. anti-CD48 antibody as described in U.S. Pat. No. 9,228,014), an anti-Fel d1 antibody (e.g. as described in U.S. Pat. No. 9,079,948), an anti-Middle East Respiratory Syndrome virus (e.g. an anti-MERS antibody as described in U.S. Pat. No. 9,718,872), an anti-Ebola virus antibody (e.g., as described in U.S. Pat. No. 9,771,414), an anti-Zika virus antibody, an anti-Lymphocyte Activation Gene 3 antibody (e.g., an anti-LAG3 antibody, or an anti-CD223 antibody), an anti-Nerve Growth Factor antibody (e.g., an anti-NGF antibody as described in U.S. Pat. Appln. Pub. No. US2016/0017029 and U.S. Pat. Nos. 8,309,088 and 9,353,176) and an anti-Activin A antibody.

In some embodiments, the bispecific antibody is selected from the group consisting of an anti-CD3×anti-CD20 bispecific antibody (as described in U.S. Pat. No. 9,657,102 and U.S. Pat. Appln. Pub. No. US20150266966A1), an anti-CD3×anti-Mucin 16 bispecific antibody (e.g., an anti-CD3×anti-Muc16 bispecific antibody), and an anti-CD3×anti-Prostate-specific membrane antigen bispecific antibody (e.g., an anti-CD3×anti-PSMA bispecific antibody). In some embodiments, the protein of interest is selected from the group consisting of abciximab, adalimumab, adalimumab-atto, ado-trastuzumab, alemtuzumab, alirocumab, atezolizumab, avelumab, basiliximab, belimumab, benralizumab, bevacizumab, bezlotoxumab, blinatumomab, brentuximab vedotin, brodalumab, canakinumab, capromab pendetide, certolizumab pegol, cemiplimab, cetuximab, denosumab, dinutuximab, dupilumab, durvalumab, eculizumab, elotuzumab, emicizumab-kxwh, emtansinealirocumab, evinacumab, evolocumab, fasinumab, golimumab, guselkumab, ibritumomab tiuxetan, idarucizumab, infliximab, infliximab-abda, infliximab-dyyb, ipilimumab, ixekizumab, mepolizumab, necitumumab, nesvacumab, nivolumab, obiltoxaximab, obinutuzumab, ocrelizumab, ofatumumab, olaratumab, omalizumab, panitumumab, pembrolizumab, pertuzumab, ramucirumab, ranibizumab, raxibacumab, reslizumab, rinucumab, rituximab, sarilumab, secukinumab, siltuximab, tocilizumab, tocilizumab, trastuzumab, trevogrumab, ustekinumab, and vedolizumab.

EXAMPLES

Example 1: Universal In-line Protein Concentration Model for UF/DF Applications

Materials and Methods

The data collection for the model included spectral data from Raman Rxn2 and Rxn 4 analyzers (Kaiser Optical Systems, Inc. Ann Arbor, MI) utilizing MR-Probe-785 and RamanRxn Probehead-758 (Kaiser Optical Systems, Inc. Ann Arbor, MI). Additionally, several different optics were used throughout development based on availability. Raman analyzers operating parameters were set to a 10 second scan time for 6 accumulations, repeated 5 times. SIMCA 13 (MKS Data Analytic Solutions, Umea, Sweden) was used to correlate peaks within the spectral data to offline protein concentration measurements. Inline measurements were made throughout different points of UF/DF unit operation including primary concentration, diafiltration, and final concentration. Offline protein concentrations were determined using SoloVPE (C Technologies, Inc.). SoloVPE measurements were made in triplicate.

Figure 2:
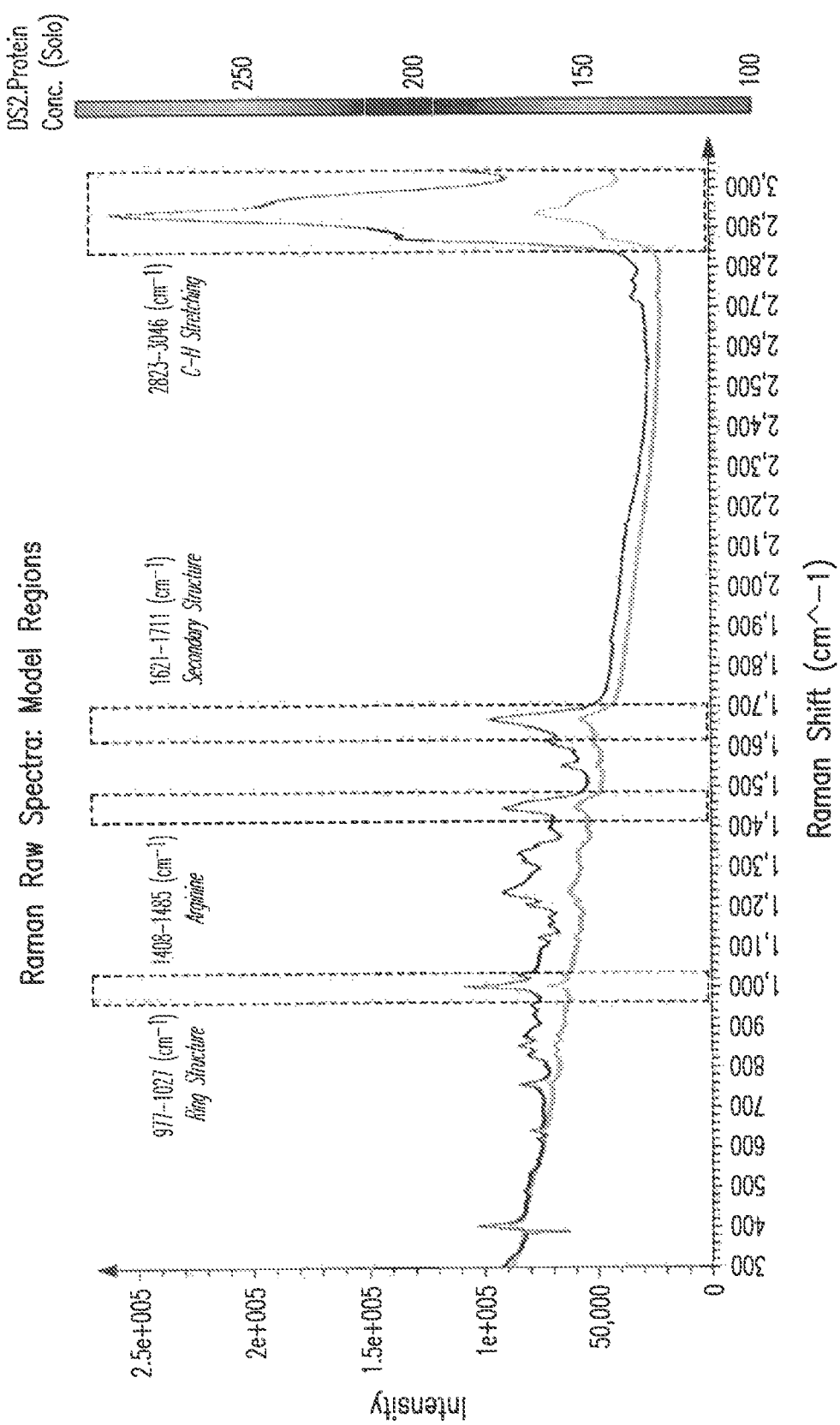
FIG. 2 is a representative spectrograph showing the initial model development for in-line Raman spectroscopy. The X axis represents the Raman shift. The Y axis represents intensity. The legend on the right represents protein concentration. Spectral regions used during the initial model development include, from left to right, 977-1027 $cm^{-1}$ (Ring structure), 1408-1485 $cm^{-1}$ (Arginine), 1621-1711 $cm^{-1}$ (Secondary structure), and 2823-3046 $cm^{-1}$ (C—H stretching).
Figure 3:
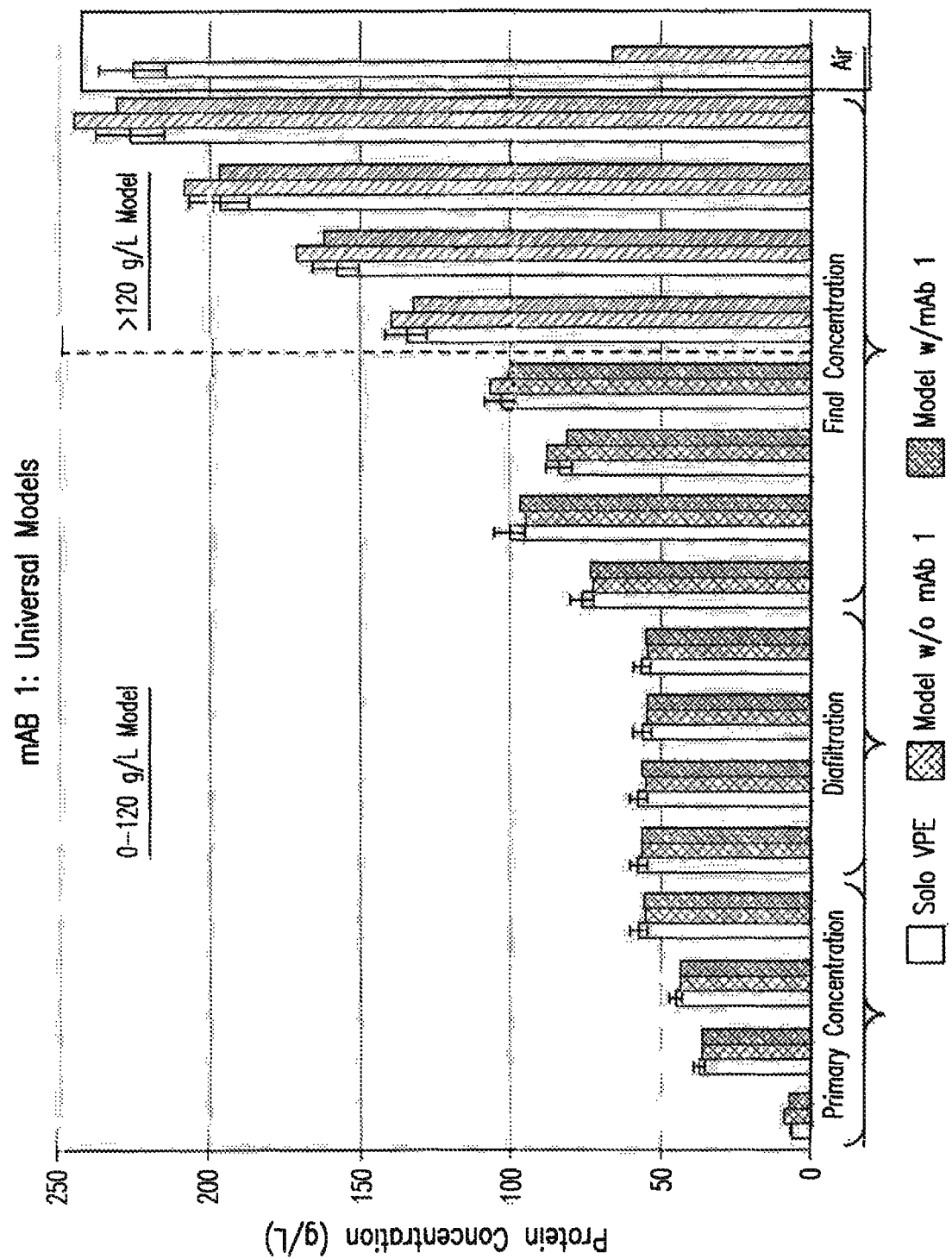
FIG. 3 is a bar graph showing protein concentration (g/L) for mAb1 during a standard ultrafiltration/diafiltration unit operation. The empty bars are concentrations determined using the UV-Vis based offline method with a SoloVPE system (C-technologies) with error bars of ±5% which is the goal for the inline Raman predictions. The bars with wide hatching represent the model herein referred to as the universal model without mAb1 included in the Raman predictions and the bars with narrow hatching represent the universal model with mAb1. The cross-hatched bars correspond to the predictions from the initial universal model with a range of 0-120 g/L. The hatched bars correspond to the predictions from the initial universal model >120 g/L.

FIG. 2 shows the spectral regions that were used for making the chemometric models. The regions included region 1—977-1027 $cm^{-1}$ (Ring structure), region 2—1408-1485 $cm^{-1}$ (Arginine), region 3—1621-1711 $cm^{-1}$ (Secondary structure), and region 4—2823-3046 $cm^{-1}$ (C—H stretching). The following spectral filtering was performed on the raw spectral data: 1st derivative with 21 $cm^{-1}$ point smoothing to remove varying baselines Results To determine the feasibility of a universal inline protein concentration model for ultrafiltration/diafiltration (UF/DF) applications mAb1 was analyzed using Raman spectroscopy. Protein concentration was measured before diafiltration (primary concentration), during diafiltration (diafiltration), and after diafiltration (final concentration). The calculated concentrations from the model were compared to the protein concentration determined by SoloVPE (FIG. 3). The model error for 0-120 g/L (primary concentration and diafiltration) was 3.1% and the model error for >120 g/L (final concentration) was 1.8% when the training set data was included (mAb 1 spectra incorporated into PLS model).

Processing errors can be detected by Raman spectroscopy. FIG. 3 shows that air entrainment in the system during final recirculation through the UF/DF system was detected by the Raman spectral data. The bars bounded by the rectangle show that the predicted concentration of mAb1 by SoloVPE was >200 g/L while the Raman prediction was ~65 g/L.

Figure 4:
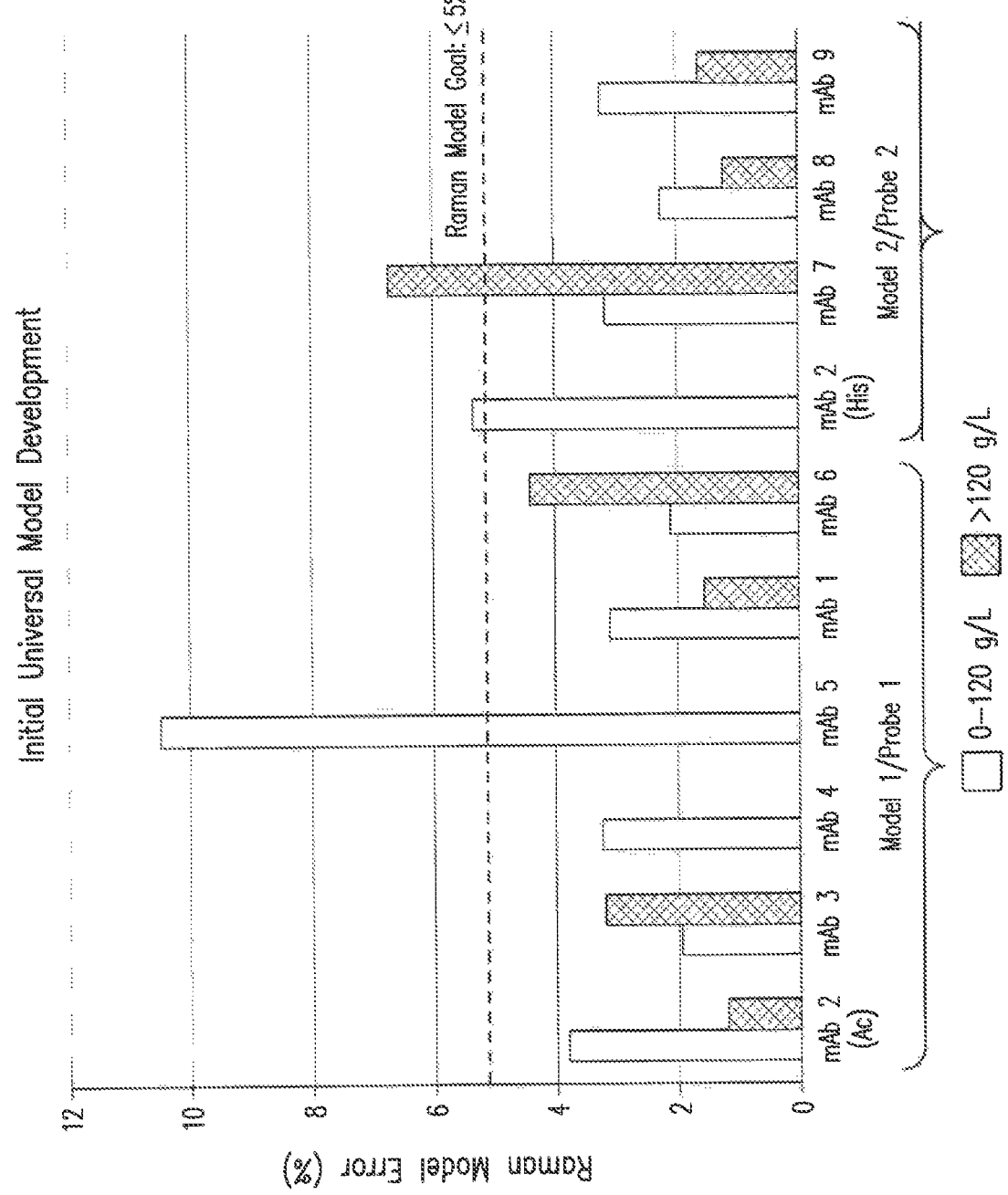
FIG. 4 is a bar graph showing absolute Raman model error for various mAbs from the initial universal model development. The hatched bars represent the initial universal model 0-120 g/L (Primary concentration and Diafiltration) and the empty bars represent from the initial universal model >120 g/L. (Final Concentration). The horizontal line represents the ≤5% error Raman model goal.

FIG. 4 shows absolute Raman model error for ten representative mAbs. This data showed the successful development of models for the mAbs shown which included different mAb isotypes (IgG1 and IgG4) as well as bispecific molecules. 14 out of 17 model predictions met ≤5% error. However, specific models (0-120 g/L and >120 g/L) were created for each probe that was used during development as probe to probe variability inflated the errors predicted by the PLS models.

Figure 5:
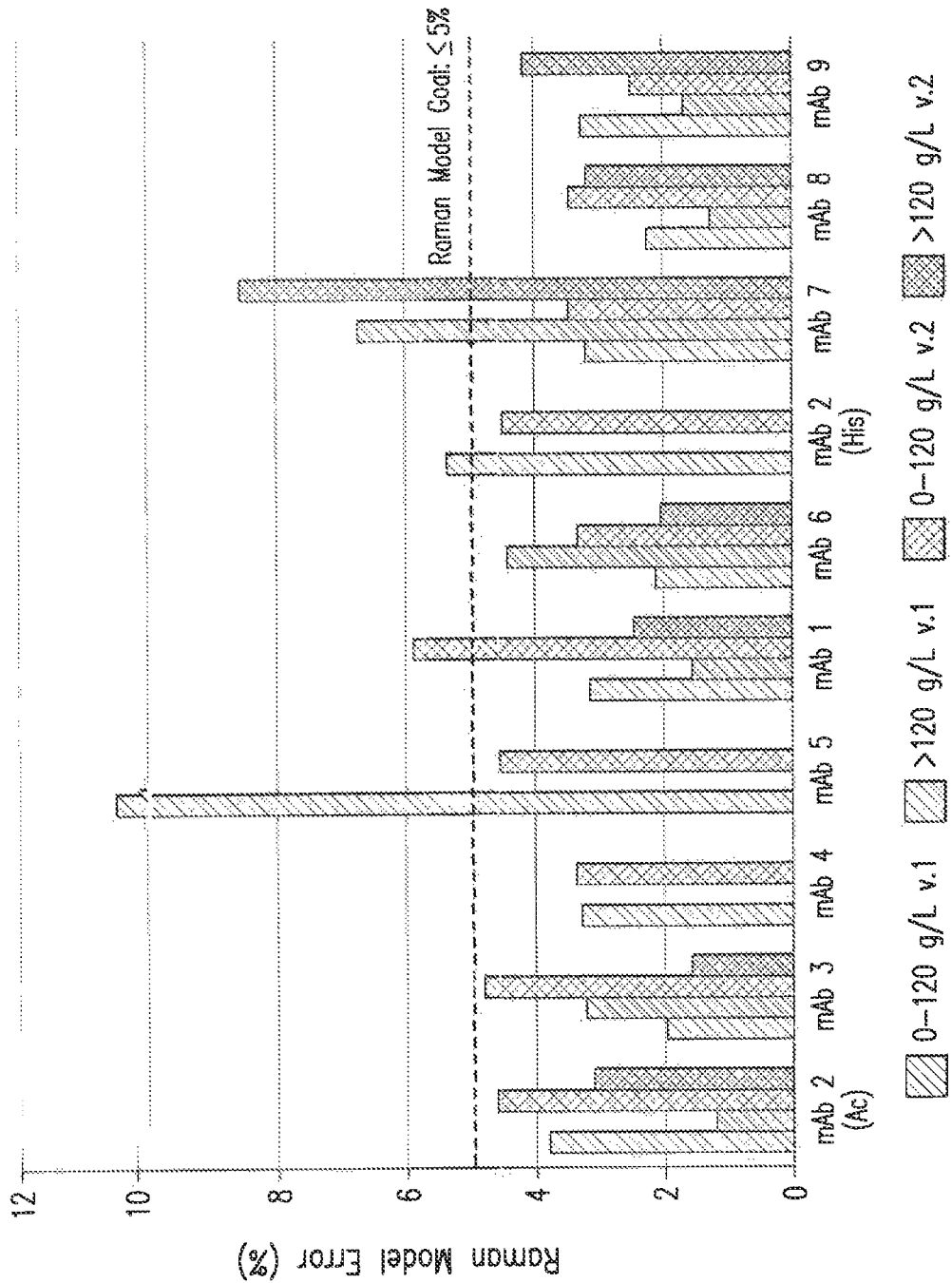
FIG. 5 is a bar graph showing absolute Raman model error for various mAbs. The bars with wide hatching represent 0-120 g/L (Primary concentration and diafiltration) and the bars with narrow hatching represent >120 g/L (final concentration). The horizontal line represents the ≈5% error Raman model goal. Two versions of the universal Raman model are shown. The hatched bars represent the initial universal model and the cross-hatched bars represent the updated universal model.

To optimize the model, different probes and lasers were tested in line with multiple mAbs. Model refinement was performed where only one spectral region was the focus of the updated universal model: 2823-3046 $cm^{-1}$ (C—H stretching) with a spectral filtering of Standard Normal Variant (SNV) to correct for laser power variation and probe variability as a baseline correction. A comparison of the two model components developed is summarized in Table 1. Partial Least Squares (PLS) regression models were created with corresponding offline SoloVPE measurements performed in triplicate. The Partial Least Squares Regression Model details are shown in Table 2. The updated dataset predicted with an optimized laser/probe universal model showed 15 out of 17 model predictions meeting ≤5% error compared to previous 14 out of 17 (FIG. 5).

TABLE 1

Universal Model Components Comparison

| Component Description | Universal Model (v. 1) | Universal Model (v. 2) |
|---|---|---|
| Laser | 1 | 3 |
| Optics | 2 | 6 |
| Preprocessing filter | 1$^{st}$ Derivative with 21 $cm^{-1}$ point smoothing | Standard Normal Variant (SNV) |
| Spectral Regions | 977-1027 $cm^{-1}$ 1408-1485 $cm^{-1}$ 1621-1711 $cm^{-1}$ 2823-3046 $cm^{-1}$ | 2823-3046 $cm^{-1}$ |

TABLE 2

Protein Concentration Partial Least Squares Regression Universal Model (v. 2) Details

| Final Models | 0-120 g/L | >120 g/L |
|---|---|---|
| Sample Size | 1412 | 879 |
| $R^2X$ | 0.993 | 0.987 |
| $Q^2$ | 0.984 | 0.958 |
| RMSECV | 3.34 | 7.77 |

$R^2X$-Percent of variation explained by the model, Target: $R^2 > 0.9$
$Q^2$-Percent of variation predicted by the model during cross-validation, Target: $Q^2 > 0.8$
RMSECV: Root mean square error of cross-validation Example 2: Scale-up Performance of Protein Concentration Models Materials and Methods The optimized Universal models (v. 2) (see Table 1) were tested with a scale-up ½" Single Use Tangential Flow Filtration System (Pall Corporation) experiment with mAb10. The mAb10 load material was formulated drug substance, rather than typical processing load material. The FDS material was diluted to representative UF/DF load source including protein concentration and buffer excipients. However, due to the presence of additional excipients in load source that had not been tested during the universal model development, mAb 10 specific models were created. Refer to example 1 for methods for Raman data collection and scan length information. The mAb specific model for >120 g/L used the same spectral regions and pre-processing techniques as the Universal model (v. 2). However, the 0-120 g/L mAb specific model used the four spectral regions as shown in FIG. 2 with Standard Normal Variant pre-processing. The differences in the 0-120 g/L model can be attributed to the additional excipients in the load source.

Results

Figure 7:
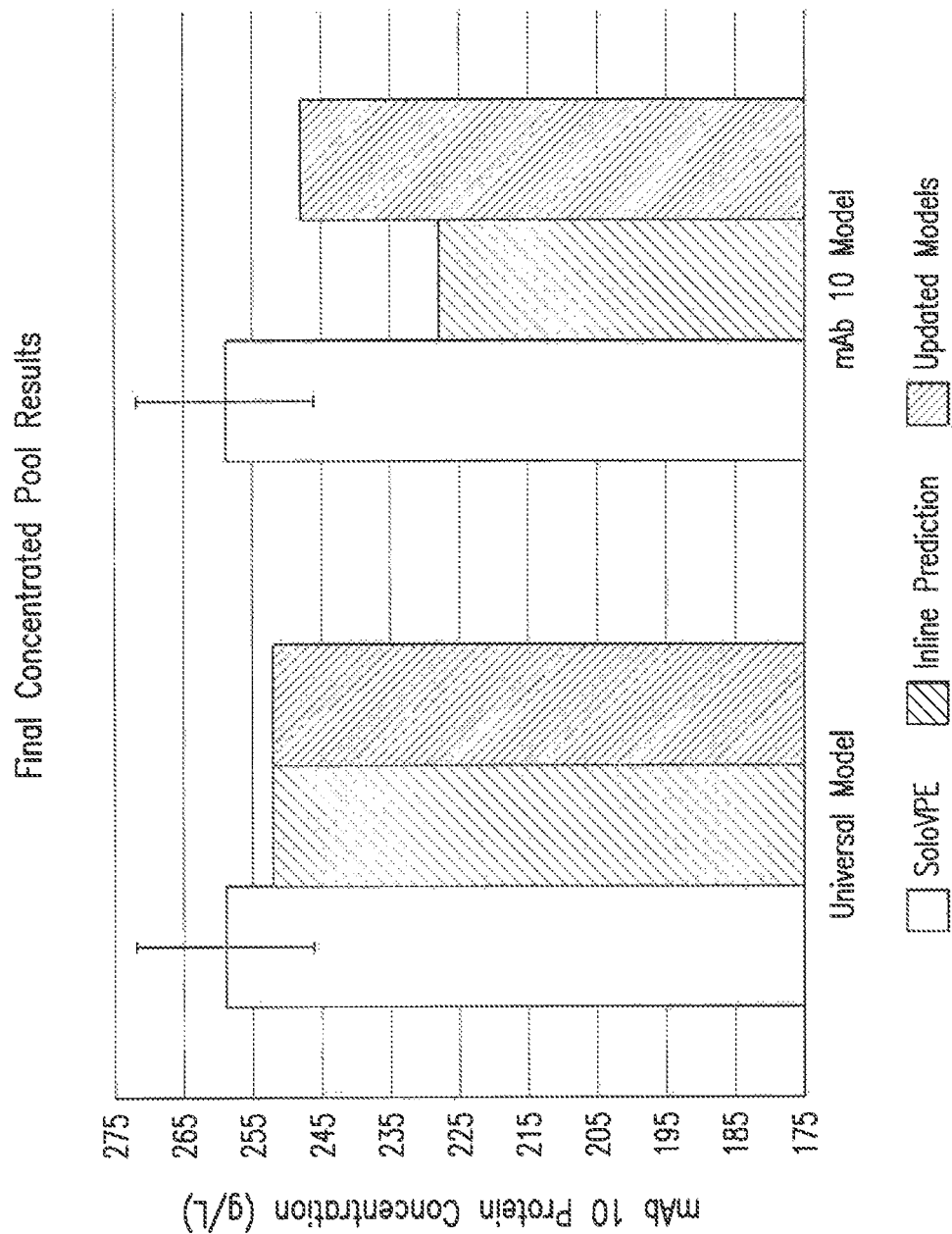
FIG. 7 is a bar graph showing protein concentration for mAb10 using the universal model or the mAb10 specific model for final concentrated pool (FCP) measurements. Protein concentrations are shown for inline real-time Raman predictions (bars with wide hatching), updated models (bars with narrow hatching), and SoloVPE (empty bar). The X axis represents experimental group and the Y axis represents protein concentration.

The model goal of ≤5% error was met for ¾ updated models when the training set was included in the model predictions as shown in Table 3. Based on the notable differences such as the load source, laser and scale (bench scale vs. scale-up) during the preliminary experimentation at TOPS a second run was performed. Prior to the second experiment, a change was made to the 0-120 g/L mAb 10 specific model. All four regions were included using SNV pre-processing but the three regions; 977-1027 cm$^{-1}$, 1408-1485 cm$^{-1}$, and 1621-1711 cm$^{-1}$ additionally used 1$^{st}$ derivative with 21 cm$^{-1}$ point smoothing. A summary of the compiled experimental results is summarized in Table 3. During the second experiment, the model goal of ≤5% error was met for ¾ updated models when the training set was included in the model predictions as shown in Table 3. An additional observation made during data analysis was the load source being the main contributing factor to increased error. If the load sample is removed, the universal model error is reduced from 8.6% to 5.7%. In FIG. 7, the results for the inline predictions (real-time, bars with wide hatching) and updated models (bars with narrow hatching) for the final concentrated pool are shown comparing the protein concentration to the offline measurement of the SoloVPE (empty bars). The universal model inline and updated model had an error of 2.7% whereas the mAb 10 model inline and updated model was 12.0% and 4.2%, respectively for final concentrated pool. The increased error observed in the mAb 10 model can be attributed to limited data in the ~250 g/L range whereas the universal model has a larger data set. An additional contributing factor to the increased error is the inability of models to extrapolate outside the characterized range (i.e. >250 g/L in the mAb 10 model).

TABLE 3

Average Model Error for Protein Concentration Predictions in Scale Up

|  | IOPS Experiment # 1 | | IOPS Experiment # 2 | |
| --- | --- | --- | --- | --- |
|  | Inline | Updated | Inline | Updated[1] |
| Universal 0-120 g/L | 13.8% | 8.9% | 9.9% | 8.6% |
| Universal >120 g/L | 8.8% | 2.8% | 5.1% | 5.0% |
| mAb 11 0-120 g/L | 6.0% | 5.5% | 4.1% | 3.5% |
| mAb 11 >120 g/L | 12.0% | 1.5% | 8.8% | 3.6% |

[1]Removal of load sample reduces error; Universal (0-120 g/L): 8.6% to 5.7% and mAb11 (0-120 g/L): 3.5% to 2.7%

Example 3: Protein Concentration Model Scale-Up to Pilot Processing Equipment

Materials and Methods

During process development of commercially enabled processes, the UF/DF is characterized as unit operation following Quality by Design principles to understand critical process parameters as well as critical quality attributes. Raman and model development was included during mAb 11 development to enhance process understanding and propose a streamlined approach to model development. Refer to example 1 for method information for Raman data collection with the exception of scan time length which was adjusted from 10 seconds to 5 seconds. The developed mAb 11 model used SNV pre-processing for all four spectral regions but the three regions; 977-1027 cm$^{-1}$, 1408-1485 cm$^{-1}$, and 1621-1711 cm$^{-1}$. additionally used 1$^{st}$ derivative with 21 cm$^{-1}$ point smoothing.

Figures 8A, 8B:
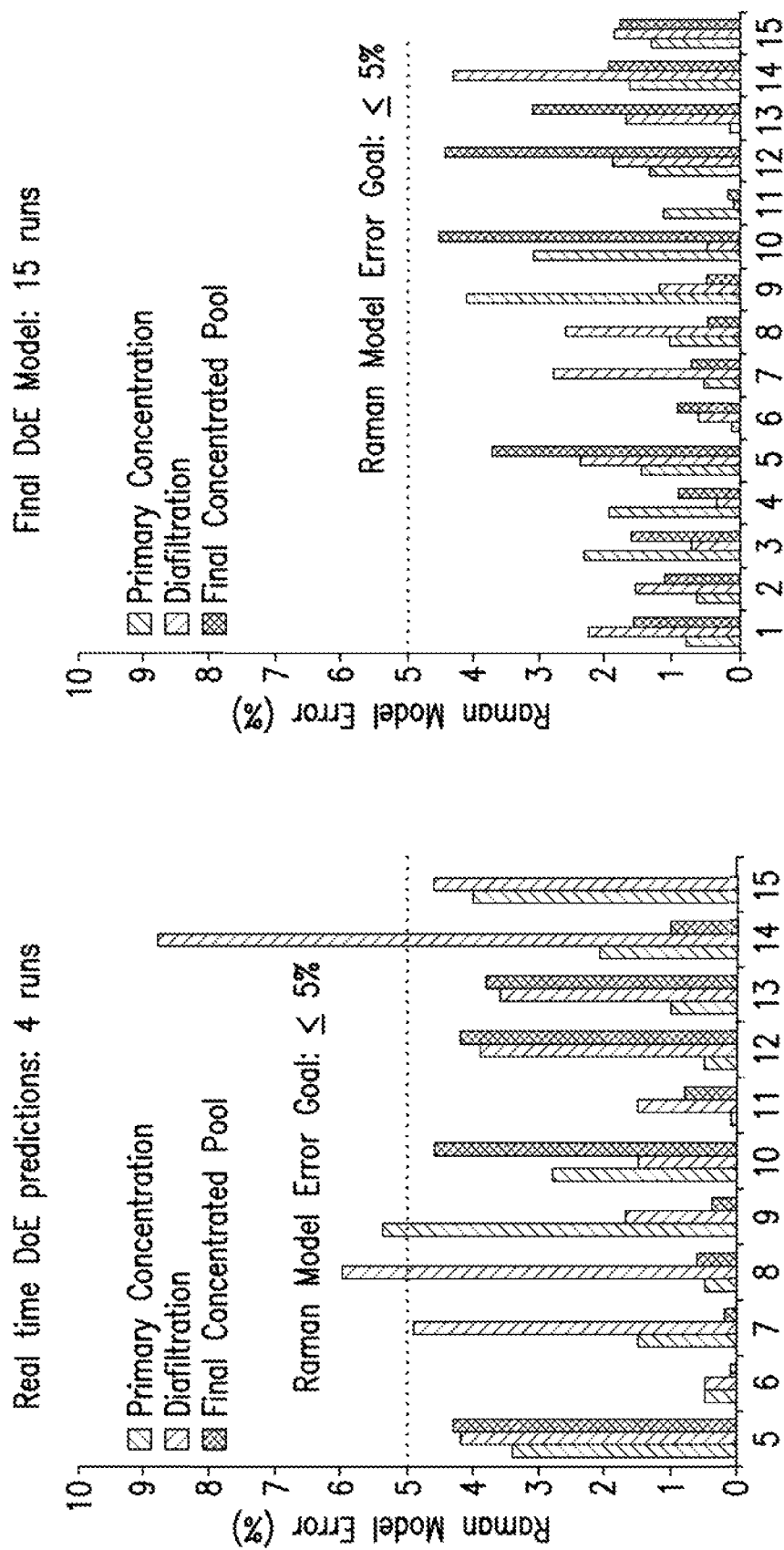
FIGS. 8A-8B are bar graphs showing Raman model error for bench scale DoE modeling for protein concentration.

Results:

The bench-scale model was generated using four DoE experiments and 4 spectral regions. FIG. 8A shows the Raman model error for real time predictions from four DoE experiments. FIG. 8B shows the Raman model error for 15 additional experiments using the bench scale model. mAb specific protein concentration models were generated for 0-120 g/L and >120 g/L with ≤5% error.

Figure 9A:
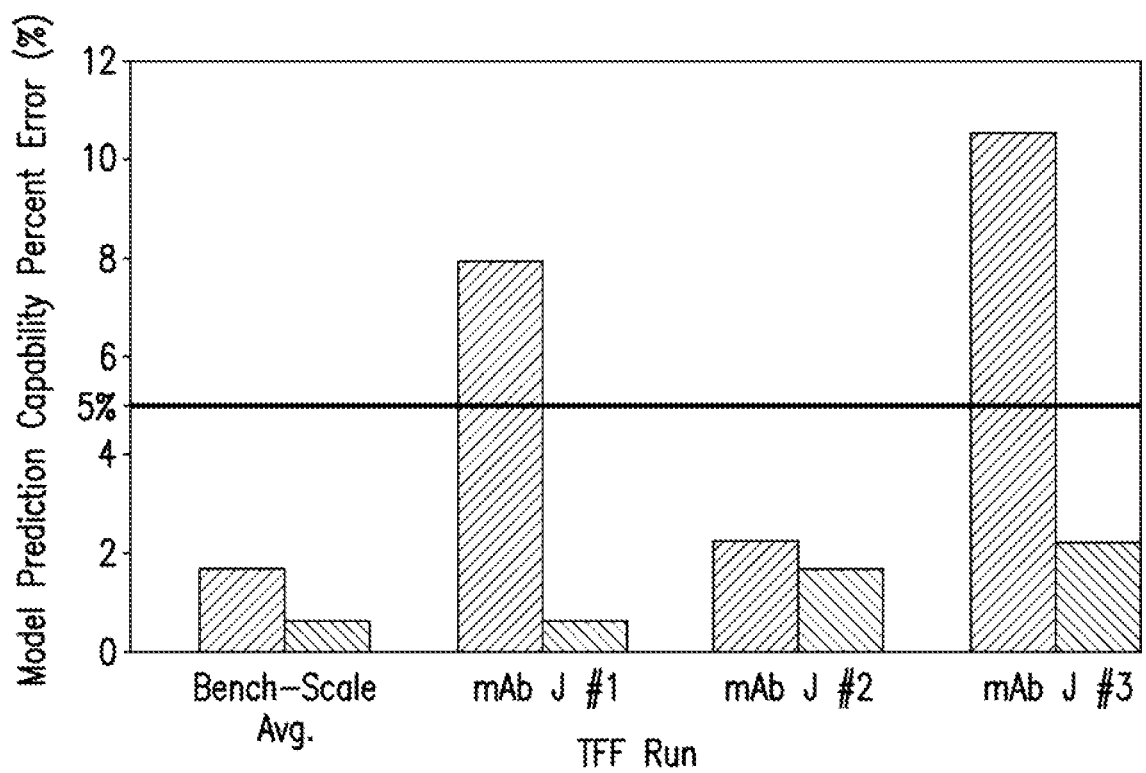
FIG. 9A is a bar graph showing model prediction capability percent error for model scale-up to pilot processing equipment for mAb11. Bench-scale model data is compared to bench-scale model date incorporating the pilot-scale data. The X-axis represents experimental groups and the Y-axis represents model prediction capability percent error (%).

Using bench-scale model (n=15), pilot-scale runs (n=3) have a prediction error of 0.6%-10.6% for mAb11 (FIG. 9A). Pilot-scale prediction error decreased to 0.6-2.2% when pilot-scale data was incorporated into the bench-scale model (n=18). Increased bench-scale model error is likely a result of temperature impact on Raman spectral shifts due to heat dissipation associated with scale-up equipment. Temperature will be a factor considered during future Raman development and model verification claims.

Figure 9B:
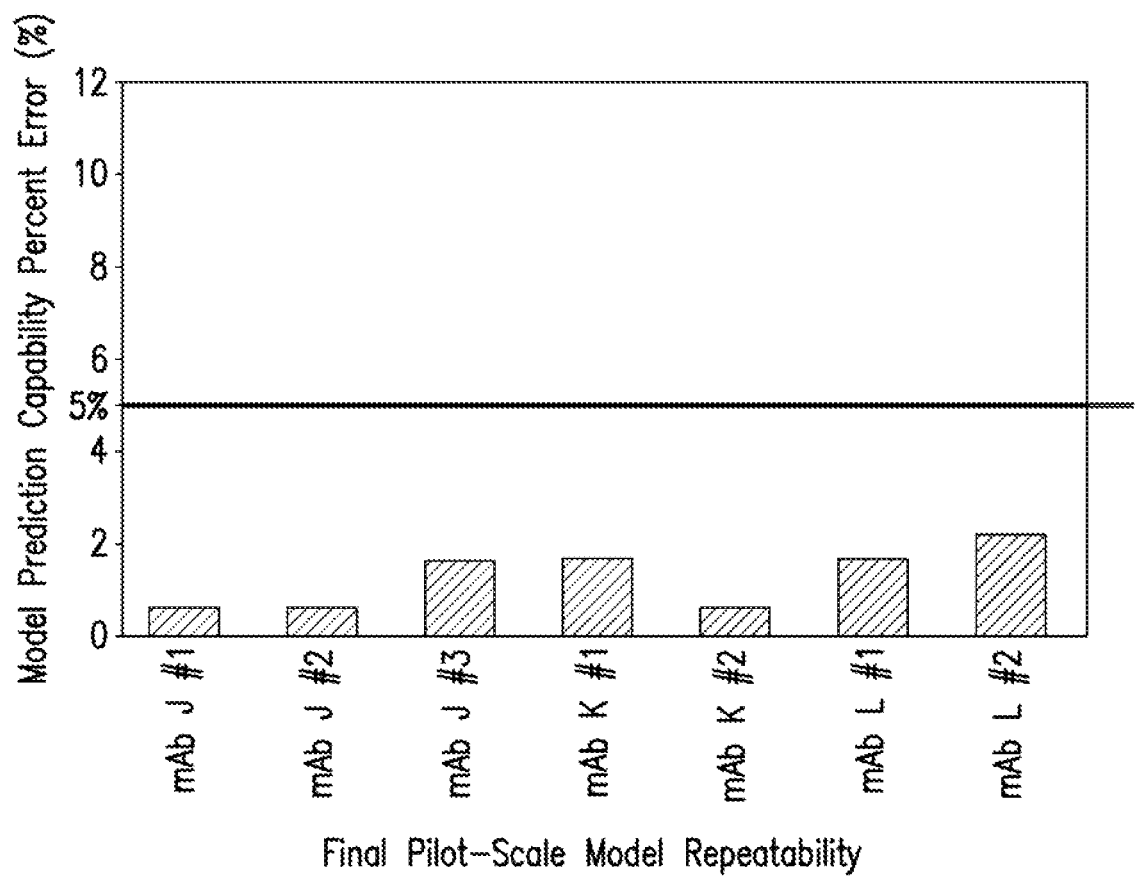
FIG. 9B is a bar graph showing model prediction capability for pilot-scale processing for various monoclonal antibodies. The X-axis represents experimental groups and the Y-axis represents model prediction capability percent error (%).

In seven pilot scale experiments with three different monoclonal antibodies (mAb J, mAb K, and mAb L) final model prediction error was 0.6-2.2%; well within the 5% goal (FIG. 9B).

Example 4: Use of Raman Models for Real-time Concentration Determination Allowing Processing Decisions Materials and Methods Refer to example 3 for further information as the same protocol for Raman spectral collection and modeling was used for Raman automations. An automated control strategy was developed to use Raman spectral data to achieve final protein concentration targets. Using the generated predictive models, data was filtered, and was used to provide input to instrumentation on the UF/DF to terminate the unit operation upon achieving the protein concentration target. SoloVPE measurements were made in triplicate.

Figure 10A:
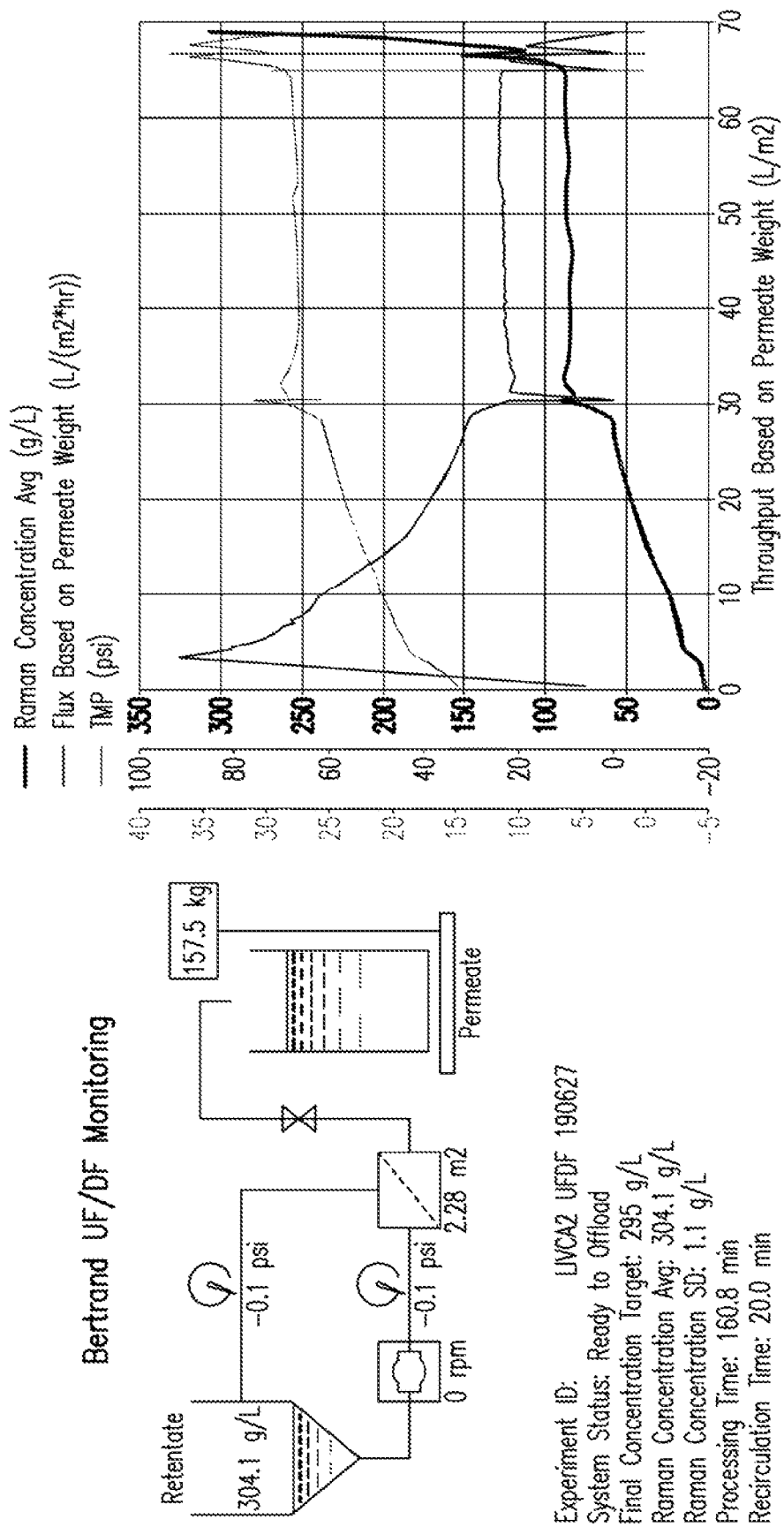
FIG. 10A is a schematic of an exemplary automated batch UF/DF with Raman feedback.
Figure 10B:
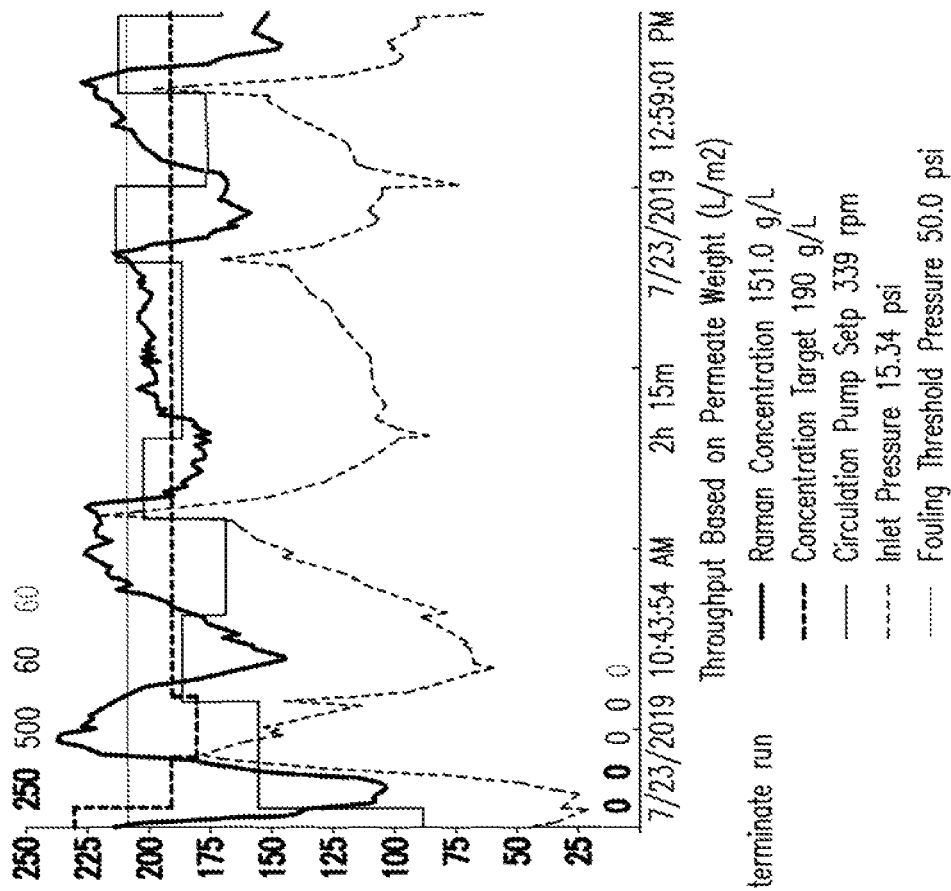
FIG. 10B is a schematic of an exemplary automated single pass TFF with Raman feedback.
Figure 10B:
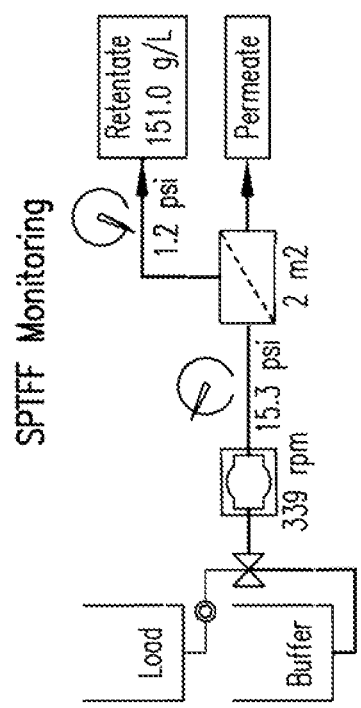
Figure 11:
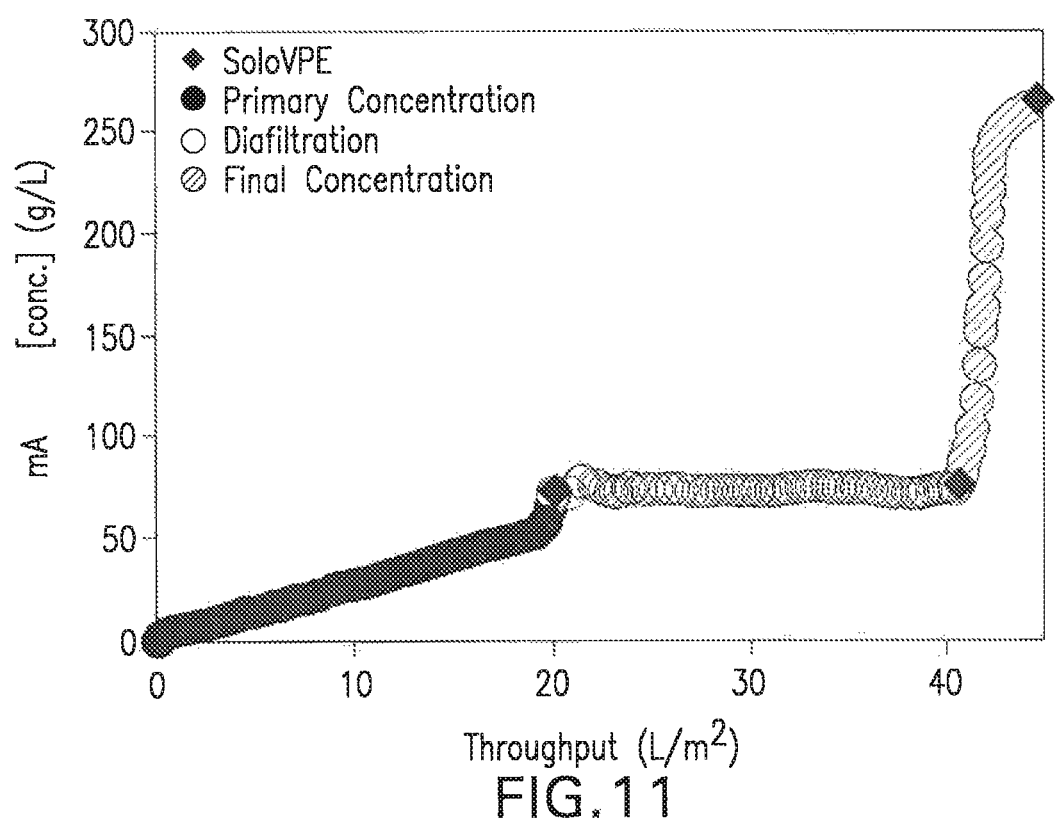
FIG. 11 is a graph showing mAb14 concentration over the course of UF/DF processing. The X-axis represents throughput ($L/m^2$) and the Y-axis represents mAb 14 concentration (g/L).

Results:

FIGS. 10A and 10B show exemplary screen setup for automated monitoring of batch UF/DF and single-pass TFF protein concentration. FIG. 11 shows that predictive modeling can be used to monitor real-time concentration of mAb14 throughout various processing steps and trigger the concentration unit operation to stop when a desired concentration target has been met. The final concentrated pool was predicted by Raman to be 260 g/L compared to the offline SoloVPE measurement of 262 g/L resulting in a 0.8% error meeting the ≤5% error goal. Raman is a suitable application to be used to make automated processing decisions verifying the desired protein concentration target is met.

Example 5: Proof of Concept for High Molecular Weight (HMW) Species Modeling in UF/DF Materials and Methods The data collection for the HMW species model included spectral data from Raman Rxn2 analyzers (Kaiser Optical Systems, Inc. Ann Arbor, MI) RamanRxn Probehead-758 (Kaiser Optical Systems, Inc. Ann Arbor, MI). Additionally, several different optics were used throughout development based on availability. Raman analyzers operating parameters were set to a 72 second scan time for 1 accumulation, repeated 25 times. Inline measurements were made throughout different points of UF/DF unit operation including primary concentration, diafiltration, and final concentration. The spectral range was 110-3415 cm$^{-1}$. The raw spectral data was pre-processed using SNV and additionally filtered using 1$^{st}$ derivative with 21 cm$^{-1}$ smoothing. Offline HMW species measurements were determined using size-exclusion ultra performance liquid chromatography.

Figure 12A:
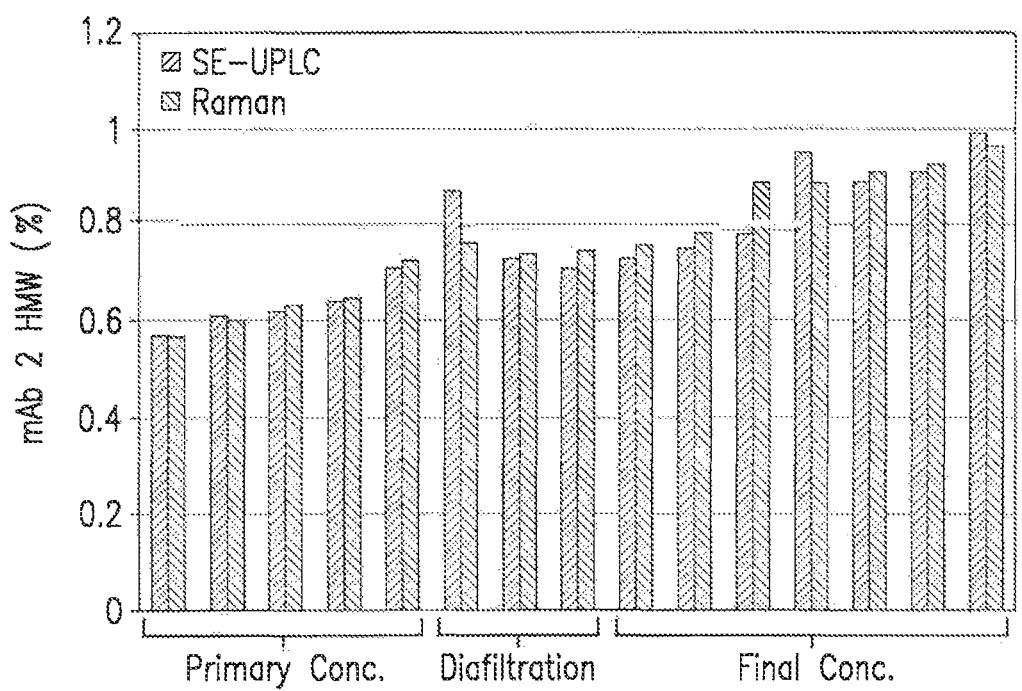
FIG. 12A is a bar graph showing the percent of high molecular weight (HMW) species in mAb2 during various steps of processing (primary concentration, diafiltration, final concentration) determined by either SE-UPLC or Raman modeling. The X-axis represents experimental group and the Y-axis represents mAb2 HMW percent (%).

Results:

HMW species are another attribute that are deemed a preliminary critical quality attribute in protein purification. Current technologies cannot monitor HMW species in real-time during processing. FIG. 12A shows that the disclosed Raman modeling method can be used to monitor HMW species during protein purification. HMW species predictions by Raman modeling were compared to measurements collected using SE-UPLC throughout purification (primary concentration, diafiltration, and final concentration). Raman modeling effectively predicted the percent of high molecular species in real-time during protein processing. The model was generated with an average error of 3.4%.

Example 6. Proof of Concept for High Molecular Weight (HMW) Species Modeling in Polishing Chromatography Materials and Methods The data collection for the HMW species model included spectral data from Raman Rxn2 analyzers (Kaiser Optical Systems, Inc. Ann Arbor, MI) utilizing MR-Probe-785. Raman analyzer operating parameters were set to either 10, 30, or 60 second scan times for 1 accumulations with 5 repetitive measurements. Offline measurements were made with anion exchange chromatography (AEX) pools with 6.2%-76.2% total HMW. The spectral ranges used for modeling and pre-processing techniques used are described in Table 4. Offline HMW species measurements were determined using size-exclusion ultra-performance liquid chromatography.

Figure 12B:
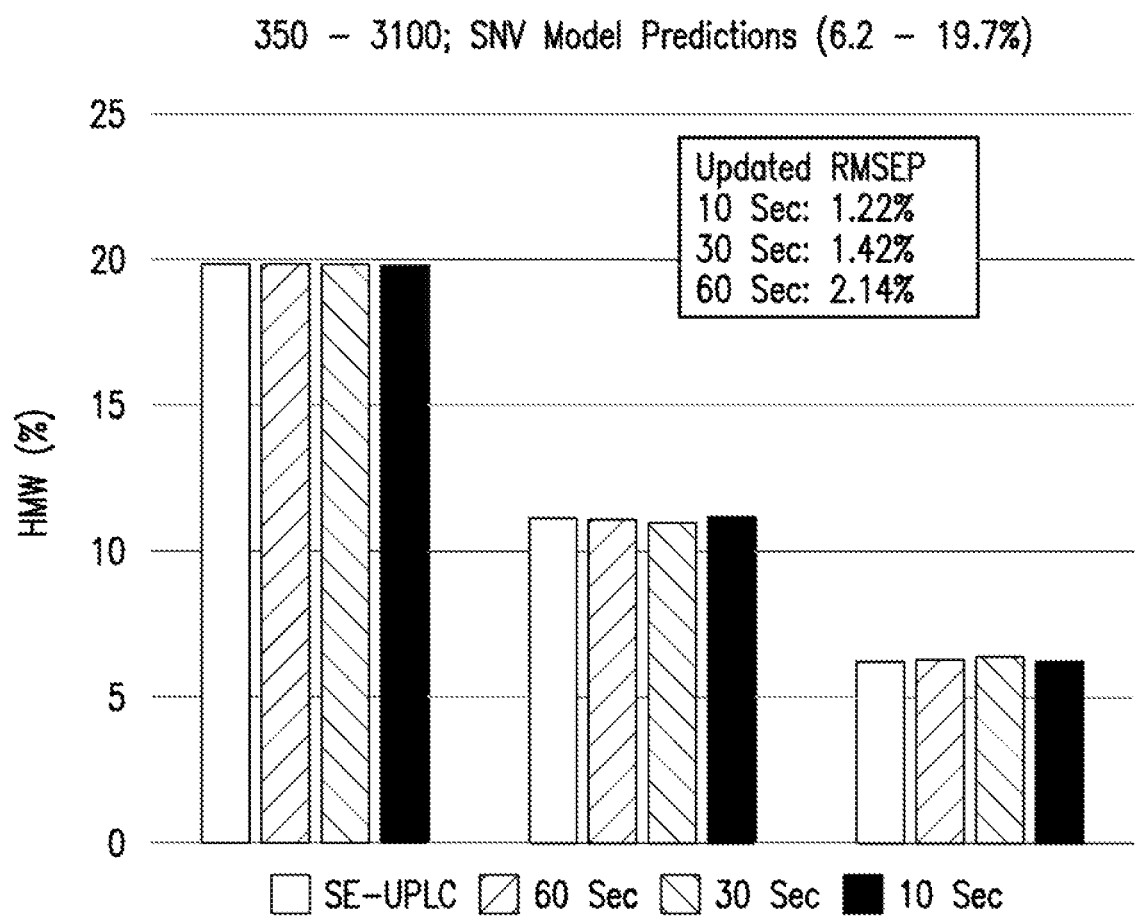
FIG. 12B is a bar graph showing the percent of high molecular weight (HMW) species predicted using various scan times (10 sec, 20 sec, 30 sec) for mAb 15. The X-axis represents experimental group and the Y-axis represents HMW percent (%).

Results:

The disclosed Raman modeling method can be used to monitor HMW species during polishing chromatography protein purification. HMW species predictions by Raman modeling were compared to measurements collected using SE-UPLC from the generated AEX pools. As summarized in Table 4, the RMSEP of the evaluated methods ranged from 3.2-7.6%. In FIG. 12B, a condensed data set of 6.2%-19.7% HMW was used to evaluate a model generated with a spectral region of 350-3100 cm$^{-1}$ and SNV pre-processing techniques. By reducing the HMW range, the RMSEP was reduced to 1.2%, 1.4%, and 2.1% for 10, 30, and 60 seconds respectively. Based on these results HMW content can be determined with Raman in AEX pools.

TABLE 4

HMW Model Predicted Error (RMSEP) for HMW content of 6.2%-76.2%.

|  | 10 Sec. | 30 Sec. | 60 Sec. |
| --- | --- | --- | --- |
| 1550-1725 cm$^{-1}$ 1$^{st}$ Der. | 7.62% | 5.31% | 3.21% |
| 350-3100 cm$^{-1}$ SNV | 3.48% | 3.37% | 4.63% |
| 990-1020, 1550-1725 cm$^{-1}$ 1$^{st}$ Der. | 7.12% | 7.48% | 4.98% |

Example 7. Proof of Concept for Titer Modeling

Materials and Methods

The training set model was 35 protein A flow through samples spiked with FCP (265 g/L) to achieve titers ranging from 0.36-9.8 g/L. The model was evaluated on diluted depth filtrate samples with titers ranging from 1.3-8.8 g/L. The data collection for the titer model included spectral data from Raman Rxn2 (Kaiser Optical Systems, Inc. Ann Arbor, MI) utilizing MR-Probe-785. An immersion probe was used in an offline fashion to generate spectral data with operating parameters set to a 20 second scan time for 1 accumulation, repeated 5 times. The spectral ranges were 977-1027, 1408-1485, 1621-1711, and 2823-3046 cm$^{-1}$. The raw spectral data was pre-processed using SNV and additionally filtered using 1$^{st}$ derivative with 21 cm$^{-1}$ smoothing. Model characteristics are described in Table 5.

TABLE 5

Antibody Titer Model Characteristics.

| Spectral Regions (cm$^{-1}$) | 3046-2823, 1711-1621, 1485-1408, 1027-977 |
| --- | --- |
| Preprocessing techniques | 1$^{st}$ derivative and SNV |
| Accumulations and Length | 5 × 20 seconds |
| Average Model Error | 25.7% |

Figure 13:
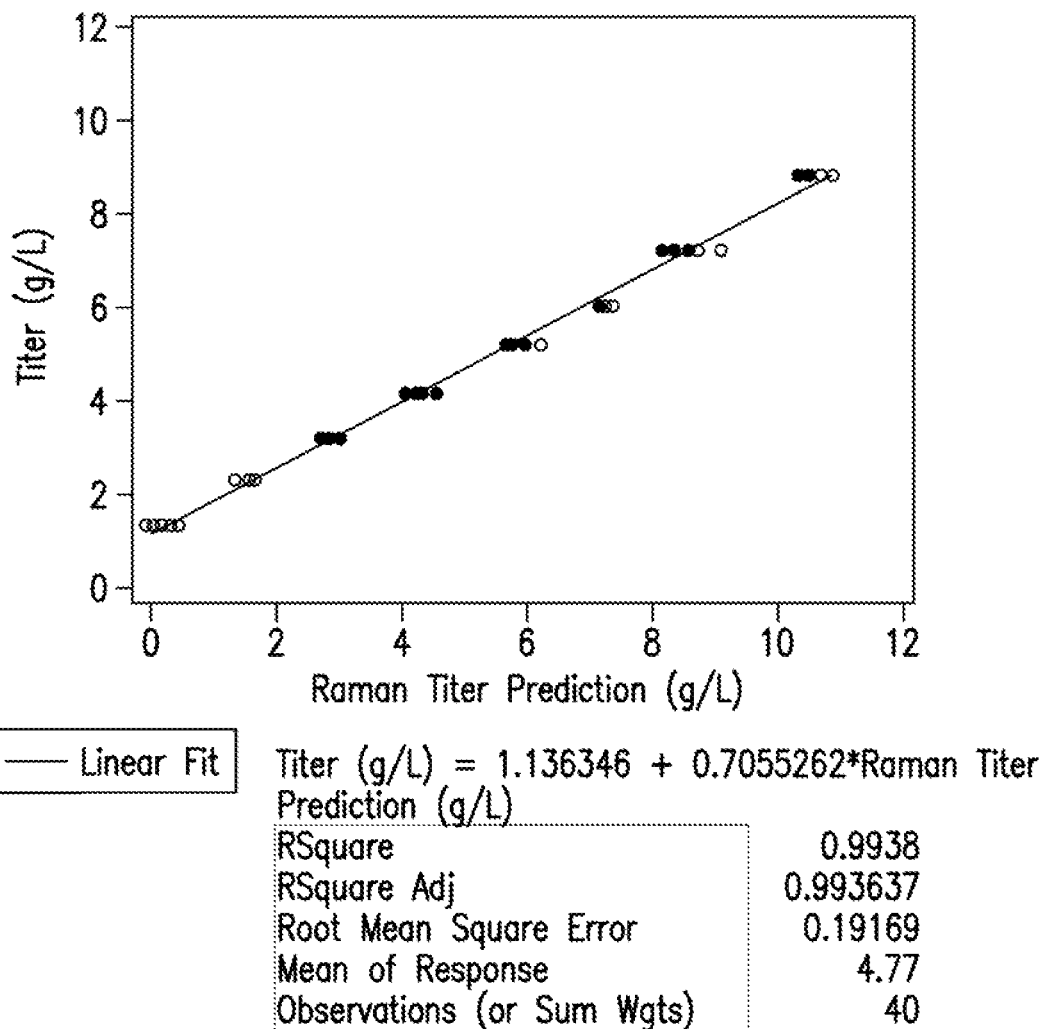
FIG. 13 is a dot plot showing actual titer (g/L) versus Raman predicted titer for monoclonal antibody samples from mAb 14. The X-axis represents Raman predicted titer and the Y-axis represents actual titer (g/L).

Results:

Antibody titer is a process attribute in protein purification that is needed to inform subsequent downstream purification unit operations including affinity column loading, production consistency, as well as in-process intermediate volume constraints. Inaccurate column loading can impact subsequent preliminary critical quality attributes hence the desire for a monitoring technique such as Raman spectroscopy. FIG. 13 shows actual antibody titer versus Raman predicted antibody titer for a monoclonal antibody. In this experiment, the model error was 26% which is higher than a desired goal of ≤5%. Increasing scan lengths as well as developing a model using diluted and non-diluted depth filtrate will reduce the model error.

Example 8: Raman Models for Buffer Excipient Measurements that Meet Current Orthogonal Assay Error of about 10%

Materials and Methods

Data was collected from previous concentration model development runs for various antibodies. Refer to example 1 for method information for Raman data collection. Table 6 shows the model components for detecting histidine and arginine in the samples. The spectral regions were based on known histidine/arginine peaks (Zhu, et al., *Spectrochim Acta A Mol Biomol Spectrosc*, 78(3):1187-1195 (2011)). Following initial model development of histidine and arginine, further model characterization was performed with mAb 14. Using a non-contact optic probe, Raman analyzer operating parameters were set to a 20 second scan time for 5 accumulations. The spectral range for histidine was 1200-1480 cm$^{-1}$ and for arginine 860-1470 cm$^{-1}$ were used. For both buffer excipients the raw spectral data was pre-processed using SNV and additionally filtered using 1$^{st}$ derivative with 21 cm$^{-1}$ smoothing. Offline histidine and arginine species measurements were determined using an ultra-performance liquid chromatography (UPLC) amino acid quantification-based method.

Figure 14A:
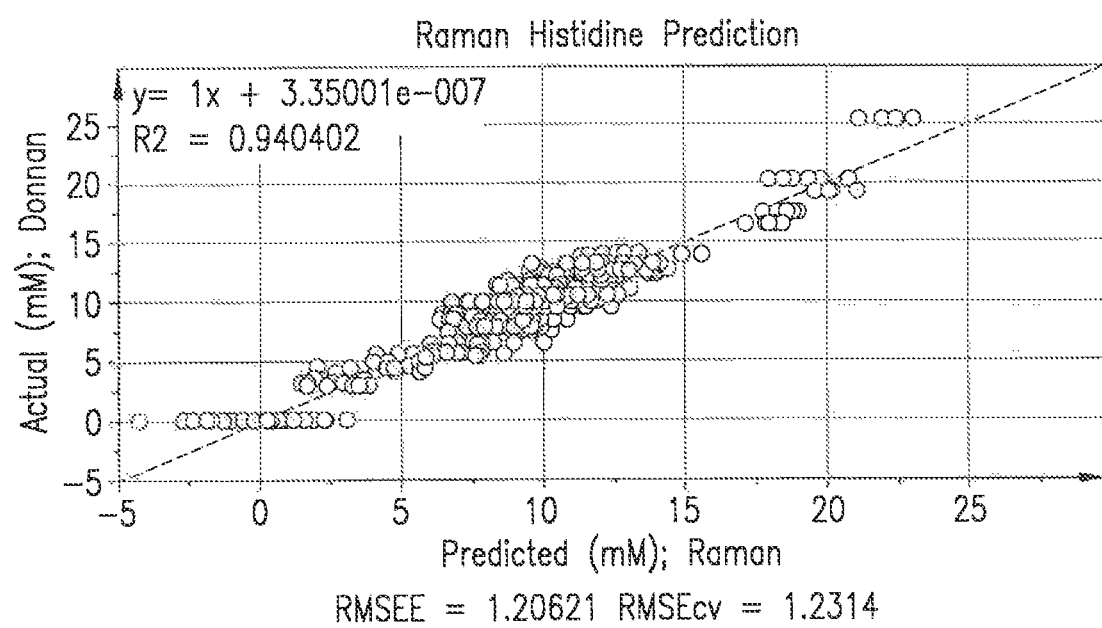
FIG. 14A is a scatter plot showing Raman histidine prediction in various monoclonal antibodies. The X-axis represents histidine concentration predicted by Raman modeling and the Y-axis represents actual histidine concentration determined by amino acid analysis.
Figure 14B:
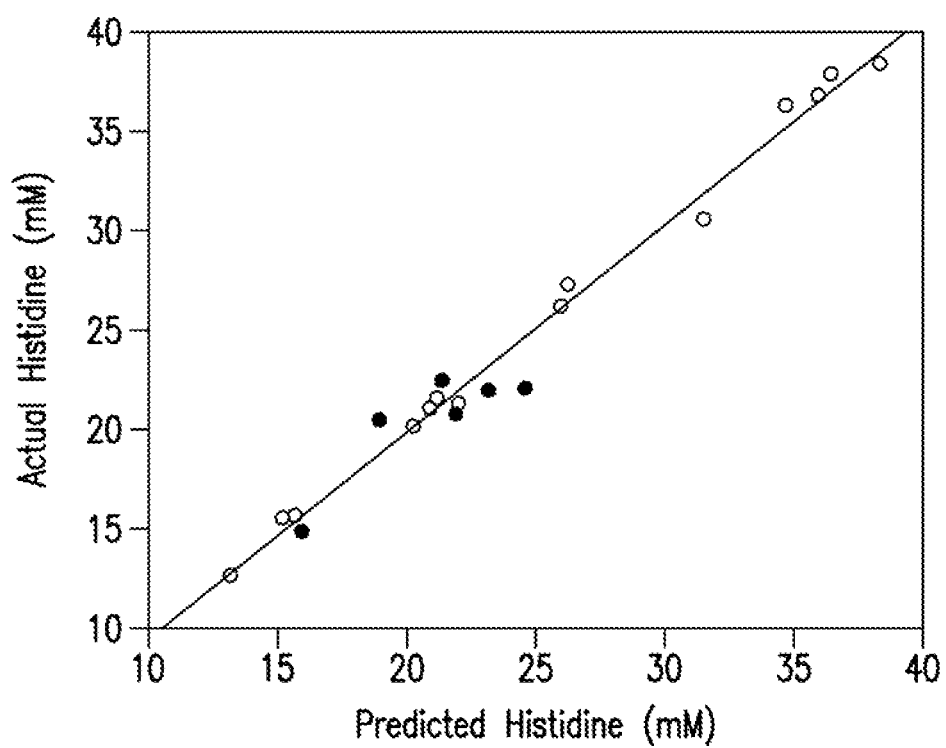
FIG. 14B is a dot plot showing actual histidine concentration versus Raman predicted histidine concentration for monoclonal antibody sample.
Figure 14C:
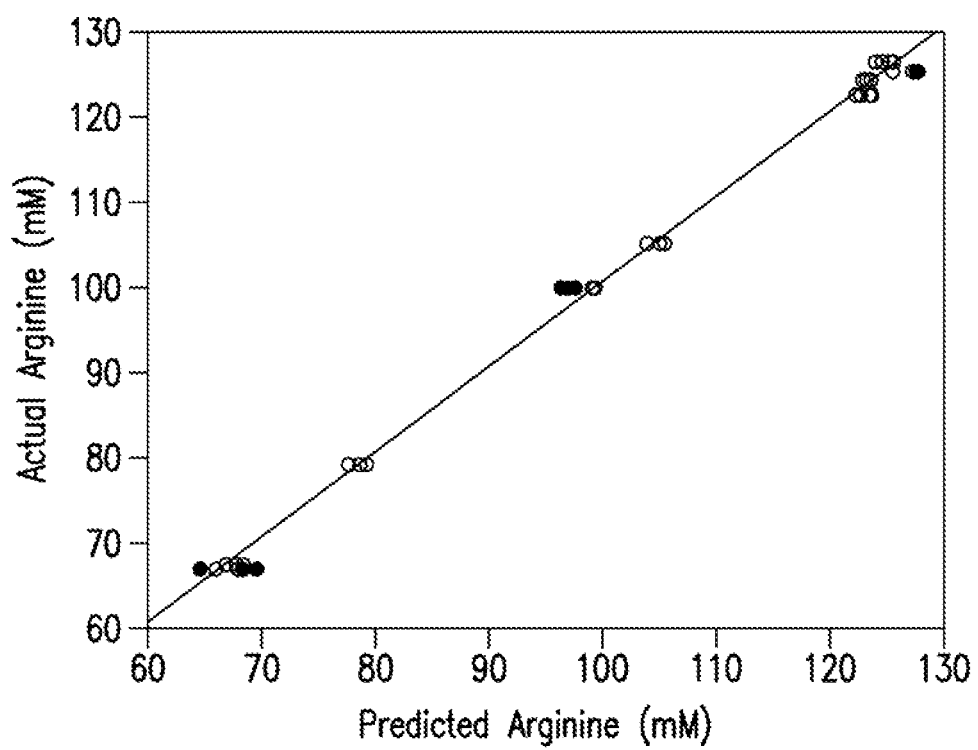
FIG. 14C is a dot plot showing actual arginine concentration versus Raman predicted arginine concentration for monoclonal antibody sample.

Results:

To determine if the disclosed Raman modeling method and system could be used to measure buffer excipients in a processed antibody sample, data collected from previous concentration model development runs were analyzed for histidine and arginine. Predicted values using Raman modeling were compared to values calculated based on the UPLC based amino acid method as can be seen in FIG. 14A. The predicted values and average model error for the preliminary histidine/arginine Raman modeling are presented in Table 6. In FIG. 14B a dot plot for predicted histidine versus actual histidine model is shown for mAb 14 with an average model error of 8.2% meeting the ≤10% goal for buffer excipients. The ≤10% goal is based on the current UPLC orthogonal method assay variability. In FIG. 14C a dot plot for predicted arginine versus actual arginine model is shown for mAb 14 with an average model error of 2.9% meeting the ≤10% goal.

This data shows that Raman modeling can be used to predict the levels of buffer excipients from in-process UF/DF and FCP material. Successful quantification of these excipients ensures that UF/DF provides a final concentrated pool that will enable subsequent formulation.

TABLE 6

Model components and data collected for histidine/arginine from universal concentration model (example 1) processing.

| | Histidine | Arginine |
|---|---|---|
| Spectral Region (cm$^{-1}$) | 1200-1480 | 970-1100, 1300-1500 |
| Preprocessing technique | 1$^{st}$ derivative and SNV | 1$^{st}$ derivative and SNV |
| R$^2$Y | 0.940 | 0.964 |
| Q$^2$ | 0.938 | 0.963 |
| RMSEP | 1.20 mM | 6.19 mM |
| Average Model Error | 10.4% | 7.39% |

Histidine Range: 0-25 mM; Arginine Range: 0-81 mM
SNV-Standard Normal Variate-mean centered and normalized
R$^2$-Percent of variation in the training set explained by the model, R$^2$ > 0.9
Q$^2$-Percent of variation in the training set predicted by the model during cross-validation, Q$^2$ > 0.8
(RMSEP) Root Mean Square Error Prediction

Example 9: Raman Models for Drug-to-antibody Ratio Measurements

Materials and Methods

DAR is a quality attribute that is monitored during development of antibody-drug conjugates (ADC), antibody-radionuclide conjugates (ARC), and general protein conjugates (potent steroids, non-cytotoxic payloads, etc.) to ensure consistent product quality and to facilitate subsequent labeling with payloads. Raman was evaluated as technology to monitor DAR levels which could then be used a control strategy for the reaction. Two different mAbs that were under development (mAb 1 and mAb 3) were assessed for DAR determination feasibility using Raman. Using a non-contact optic probe, Raman analyzer operating parameters were set to a 10 second scan time for 10 accumulations. The raw spectral range of 350-3100 cm$^{-1}$ was used with the raw spectral data pre-processed using SNV and additionally filtered using 2$^{nd}$ derivative with 21 cm$^{-1}$ smoothing. Table 7 shows the model components for determining DAR in the samples. Offline DAR measurements were determined using a UV spectroscopy-based method.

TABLE 7

Model components for drug-antibody ratio measurements.

| Model Name | REGN2810 UV-DAR | REGN910 UV-DAR |
|---|---|---|
| Y Range | 0.81-4.39 | 0.79-3.57 |
| Best Model | 2$^{nd}$ Derivative | 2$^{nd}$ Derivative |
| | R2Y = 0.788 | R2Y = 0.994 |
| | Q2 = 0.548 | Q2 = 0.776 |
| | RMSECV = 0.64 | RMSECV = 0.58 |

Figure 15A:
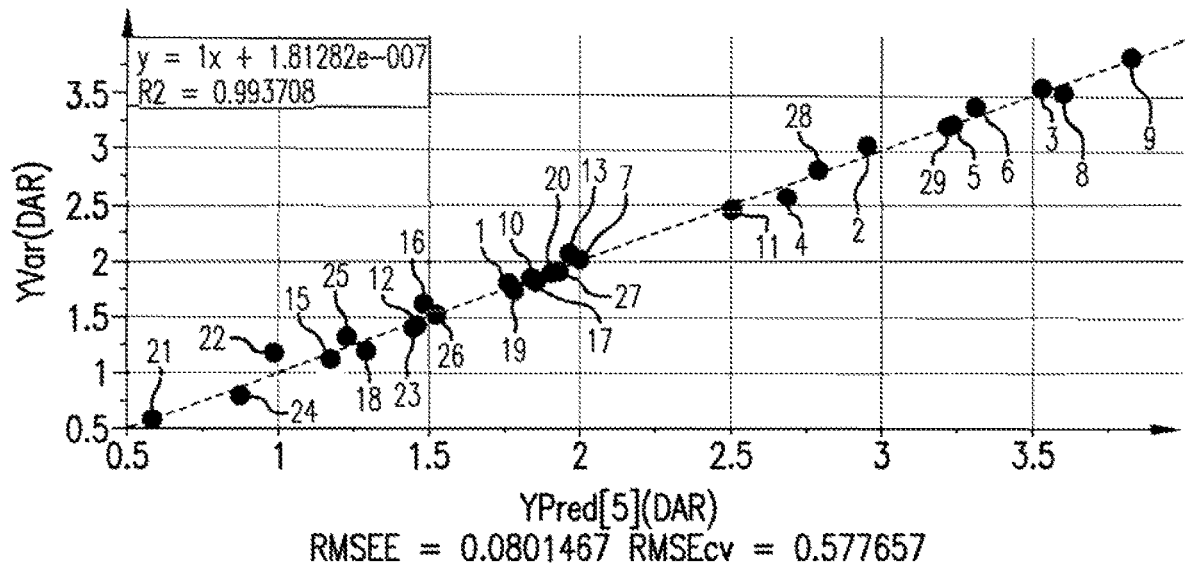
FIG. 15A is a scatter plot showing actual drug-antibody ratio (DAR) versus Raman predicted DAR for monoclonal antibody samples from mAb 3. The X-axis represents Raman predicted DAR and the Y-axis represents actual DAR determined by UV-spectroscopy.
Figure 15B:
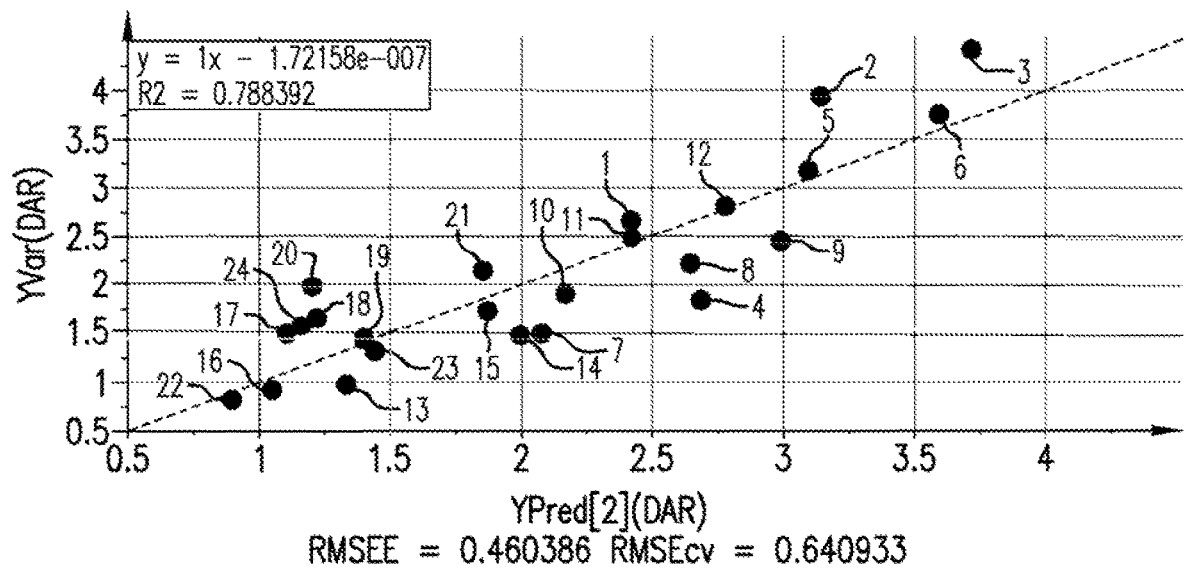
FIG. 15B is a scatter plot showing actual drug-antibody ratio (DAR) versus Raman predicted DAR for monoclonal antibody samples from mAb 1. The X-axis represents Raman predicted DAR and the Y-axis represents actual DAR.

Results:

FIGS. 15A-15B show that Raman modeling can be used to measure drug-to-antibody ratio for an iPET drug conjugates for mAb 1 and mAb 3. For both models the root mean square error of cross validation was 0.6 DAR. The current orthogonal UV based assay has variability associated with 0.3 DAR (one standard deviation). The initial Raman predication is within two standard deviations and suggests with further model refinement DAR can be successfully predicted with Raman.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of producing a protein purification intermediate, comprising:
   providing a universal model produced using a plurality of protein purification intermediates;
   quantifying one or more impurities in the protein purification intermediate using in situ Raman spectroscopy; and
   adjusting parameters of the process to obtain or maintain the protein purification intermediate at a predetermined purity.

2. The method of claim 1, wherein the parameters of the process are adjusted in-real time.

3. The method of claim 1, wherein the process is a downstream process.

4. The method of claim 1, further comprising removing the one or more impurities from the protein purification intermediate, wherein the one or more impurities impact the protein purification intermediate's safety, efficacy, potency, pharmacokinetics, or pharmacological activity, or a combination thereof.

5. The method of claim 1, wherein the one or more impurities is selected from the group consisting of a product-related impurity, a high molecular weight (HMW) species, a host cell protein, a DNA, a virus, an endotoxin, an aggregate, a concentration, an excipient, and combinations thereof.

6. The method of claim 1, further comprising quantifying one or more critical quality attributes in the protein purification intermediate using in situ Raman spectroscopy; and
adjusting parameters of the process to obtain or maintain the protein purification intermediate at a predetermined critical quality attribute level,
wherein the critical quality attributes is selected from the group consisting of antibody titer, protein concentration, high molecular weight species, drug-antibody ratio, excipients, pH, salts, and combinations thereof.

7. The method of claim 3, wherein the downstream process comprises at least one selected from the group consisting of cell harvest, centrifugation, direct depth filtration, affinity capture, protein A affinity purification, viral inactivation, polishing chromatography, ion-exchange chromatography, cation exchange chromatography, anion exchange chromatography, hydrophobic interaction chromatography, size-exclusion chromatography, virus retentive filtration, ultrafiltration/diafiltration, and combinations thereof.

8. The method of claim 1, further comprising determining the concentration of the protein purification intermediate in-real time using in situ Raman spectroscopy with the universal model while processing the protein purification intermediate.

9. The method of claim 8, wherein determining the concentration of the protein purification intermediate occurs continuously or intermittently in real-time.

10. The method of claim 1, further comprising providing a protein specific model produced using the protein purification intermediate.

11. The method of claim 10, further comprising determining the concentration of the protein purification intermediate in-real time using in situ Raman spectroscopy with the protein specific model while processing the protein purification intermediate.

12. The method of claim 1, further comprising producing the protein purification intermediate when the concentration reaches a predetermined concentration.

13. The method of claim 1, wherein the concentration of the protein purification intermediate is at least 150 mg/mL.

14. The method of claim 1, wherein the concentration of the protein purification intermediate is between about 150 mg/mL to about 300 mg/mL.

15. The method of claim 1, wherein the protein purification intermediate is concentrated using ultrafiltration, buffer exchange, or both.

16. The method of claim 1, wherein the protein purification intermediate is harvested from a bioreactor, a fed-batch culture, or a continuous culture.

17. The method of claim 1, wherein the protein purification intermediate is selected from the group consisting of an antibody, an antigen binding fragment, a fusion protein, and a recombinant protein.

18. The method of claim 1, further comprising performing a normalization technique or point-smoothing on the Raman spectroscopy data.

19. The method of claim 1, wherein the model provides predicted protein concentration values for a plurality of protein purification intermediates with ≤5% error compared to off-line protein concentration values.

20. The method of claim 1, wherein the protein purification intermediate is further concentrated using at least one selected from the group consisting of ultrafiltration and diafiltration.

21. The method of claim 6, wherein the excipient comprises a buffer excipient, wherein the buffer excipient comprises at least one selected from the group consisting of acetate, citrate, histidine, succinate, phosphate, tris(hydroxymethyl)aminomethane (Tris), proline, arginine, sucrose, and combinations thereof.

22. The method of claim 6, wherein the excipient comprises a surfactant excipient, wherein the surfactant excipient comprises at least one selected from the group consisting of polysorbate 80, polysorbate 20, poloxamer 188, and combinations thereof.

23. The method of claim 6, wherein the excipient comprises at least one selected from the group consisting of polyethylene glycol, sucrose, and combinations thereof.

24. The method of claim 1, wherein spectral data is collected at one or more wavenumber ranges.

25. The method of claim 24, wherein spectral data is collected at one or more wavenumber ranges selected from the group consisting of 977-1027 $cm^{-1}$, 1408-1485 $cm^{-1}$, 1621-1711 $cm^{-1}$, 2823-3046 $cm^{-1}$, and combinations thereof.

26. The method of claim 1, wherein the protein purification intermediate comprises at least one selected from the group consisting of an extracellular domain of a cell surface receptor, a fragment thereof, and combinations thereof.

27. The method of claim 1, wherein the protein purification intermediate comprises at least one selected from the group consisting of a Fc-fusion protein, a fragment thereof, and combinations thereof.

28. The method of claim 1, wherein the protein purification intermediate comprises at least one selected from the group consisting of an antibody, an antigen binding fragment thereof, and combinations thereof.

29. The method of claim 1, further comprising at least one selected from the group consisting of determining and adjusting chromatography column loadings.

* * * * *